US010918616B2

(12) United States Patent
Dyakonov et al.

(10) Patent No.: US 10,918,616 B2
(45) Date of Patent: *Feb. 16, 2021

(54) FUMARATE ESTER PHARMACEUTICAL COMPOSITIONS

(71) Applicant: BANNER LIFE SCIENCES LLC, High Point, NC (US)

(72) Inventors: Tatyana Dyakonov, Greensboro, NC (US); Sunil Agnihotri, Scarborough, ME (US); Aqeel A. Fatmi, High Point, NC (US)

(73) Assignee: BANNER LIFE SCIENCES LLC, High Point, NC (US)

( * ) Notice: Subject to any disclaimer, the term of this patent is extended or adjusted under 35 U.S.C. 154(b) by 96 days.

This patent is subject to a terminal disclaimer.

(21) Appl. No.: 16/129,904

(22) Filed: Sep. 13, 2018

(65) Prior Publication Data
US 2019/0008818 A1    Jan. 10, 2019

Related U.S. Application Data

(60) Continuation of application No. 15/730,832, filed on Oct. 12, 2017, now Pat. No. 10,105,336, which is a division of application No. 15/358,349, filed on Nov. 22, 2016, now Pat. No. 9,820,960, which is a division of application No. 15/073,720, filed on Mar. 18, 2016, now Pat. No. 9,517,209, which is a division of application No. 14/840,072, filed on Aug. 31, 2015, now Pat. No. 9,326,947, which is a continuation-in-part of application No. 14/633,164, filed on Feb. 27, 2015, now Pat. No. 9,326,965, which is a continuation-in-part of application No. PCT/US2015/017893, filed on Feb. 27, 2015.

(60) Provisional application No. 62/061,185, filed on Oct. 8, 2014, provisional application No. 62/011,604, filed on Jun. 13, 2014, provisional application No. 61/950,648, filed on Mar. 10, 2014, provisional application No. 61/946,233, filed on Feb. 28, 2014.

(51) Int. Cl.
| | | |
|---|---|---|
| A61K 31/225 | (2006.01) |
| A61P 25/00 | (2006.01) |
| A61K 9/10 | (2006.01) |
| A61K 9/00 | (2006.01) |
| A61K 47/46 | (2006.01) |
| A61K 47/12 | (2006.01) |
| A61K 47/44 | (2017.01) |
| A61K 47/32 | (2006.01) |
| A61K 47/14 | (2017.01) |
| A61K 9/48 | (2006.01) |
| A61K 45/06 | (2006.01) |
| A61K 31/22 | (2006.01) |
| A61K 9/14 | (2006.01) |

(52) U.S. Cl.
CPC .......... *A61K 31/225* (2013.01); *A61K 9/0053* (2013.01); *A61K 9/14* (2013.01); *A61K 9/48* (2013.01); *A61K 9/4808* (2013.01); *A61K 9/4825* (2013.01); *A61K 9/4833* (2013.01); *A61K 9/4858* (2013.01); *A61K 9/4866* (2013.01); *A61K 9/4875* (2013.01); *A61K 9/4891* (2013.01); *A61K 31/22* (2013.01); *A61K 45/06* (2013.01); *A61K 47/12* (2013.01); *A61K 47/14* (2013.01); *A61K 47/32* (2013.01); *A61K 47/44* (2013.01); *A61K 47/46* (2013.01)

(58) Field of Classification Search
None
See application file for complete search history.

(56) References Cited

U.S. PATENT DOCUMENTS

| | | |
|---|---|---|
| 5,146,730 A | 9/1992 | Dietel |
| 5,424,332 A | 6/1995 | Speiser |
| 5,459,983 A | 10/1995 | Dietel |
| 6,355,676 B1 | 3/2002 | Joshi |
| 6,436,992 B1 | 8/2002 | Joshi |
| 6,482,516 B1 | 11/2002 | Dietel |
| 6,509,376 B1 | 1/2003 | Joshi |
| 7,157,423 B2 | 1/2007 | Joshi |
| 7,320,999 B2 | 1/2008 | Joshi |
| 7,432,240 B2 | 10/2008 | Joshi |
| 7,612,110 B2 | 11/2009 | Joshi |
| 7,619,001 B2 | 11/2009 | Joshi |
| 7,803,840 B2 | 9/2010 | Joshi |
| 7,915,310 B2 | 3/2011 | Joshi |
| 8,293,270 B2 | 10/2012 | Sukuru |

(Continued)

FOREIGN PATENT DOCUMENTS

| | | |
|---|---|---|
| EP | 0312697 A2 | 4/1989 |
| WO | 2000030622 | 6/2000 |

(Continued)

OTHER PUBLICATIONS

Gold et al., "Safety of a novel oral single-agent fumarate, BG00012, in patients with relapsing-remitting multiple sclerosis: results of a phase 2 study," Journal of Neurology 253(Suppl. 2): II144-II145 (2006).

(Continued)

*Primary Examiner* — Abigail Vanhorn
(74) *Attorney, Agent, or Firm* — Michael Best & Friedrich LLP

(57) ABSTRACT

Described herein are pharmaceutical compositions comprising fumarate esters, methods for making the same, and methods for treating subjects in need thereof. In particular, oral pharmaceutical compositions comprising fumarate esters are described.

16 Claims, 15 Drawing Sheets

(56) References Cited

U.S. PATENT DOCUMENTS

| | | | |
|---|---|---|---|
| 8,333,989 | B2 | 12/2012 | Sukuru |
| 8,399,514 | B2 | 3/2013 | O Neill |
| 8,524,773 | B2 | 9/2013 | Joshi |
| 8,669,281 | B1 | 3/2014 | Sanrame |
| 8,669,282 | B2 | 3/2014 | Zicker |
| 8,685,445 | B2 | 4/2014 | Hassan |
| 8,759,393 | B2 | 6/2014 | Joshi |
| 9,090,558 | B2 | 7/2015 | Sanrame |
| 9,302,977 | B2 | 4/2016 | Raillard |
| 9,326,947 | B1 | 5/2016 | Fatmi |
| 9,326,965 | B2 | 5/2016 | Fatmi |
| 9,511,043 | B2 | 12/2016 | Fatmi |
| 9,517,209 | B2 | 12/2016 | Fatmi |
| 9,526,965 | B2 | 12/2016 | Gatherer |
| 9,566,259 | B1 | 2/2017 | Hughey |
| 9,636,318 | B2 | 5/2017 | Hughey |
| 9,636,319 | B1 | 5/2017 | Hughey |
| 9,814,691 | B2 * | 11/2017 | Dyakonov ............ A61K 31/225 |
| 9,814,692 | B2 * | 11/2017 | Vaughn ................ A61K 31/225 |
| 9,820,960 | B2 * | 11/2017 | Dyakonov ............ A61K 9/4875 |
| 9,820,961 | B2 * | 11/2017 | Vaughn ................ A61K 31/225 |
| 10,098,863 | B2 * | 10/2018 | Vaughn ................ A61K 9/4808 |
| 10,105,335 | B2 * | 10/2018 | Vaughn ................ A61K 31/225 |
| 10,105,336 | B2 * | 10/2018 | Dyakonov ............ A61K 9/4875 |
| 10,105,337 | B2 * | 10/2018 | Dyakonov ............ A61K 31/225 |
| 2003/0018072 | A1 | 1/2003 | Joshi |
| 2004/0054001 | A1 | 3/2004 | Petzelbauer |
| 2006/0051345 | A1 | 3/2006 | Frohna |
| 2006/0115527 | A1 | 6/2006 | Hassan |
| 2006/0165778 | A1 | 7/2006 | Hassan |
| 2007/0104778 | A1 | 5/2007 | Ketsela |
| 2007/0269507 | A1 | 11/2007 | Sanchetto et al. |
| 2008/0003282 | A1 | 1/2008 | Soll |
| 2008/0004344 | A1 | 1/2008 | Nilsson |
| 2008/0233185 | A1 | 9/2008 | Joshi |
| 2008/0299196 | A1 | 12/2008 | Muller |
| 2008/0300217 | A1 | 12/2008 | Nilsson |
| 2009/0304790 | A1 | 12/2009 | Nilsson |
| 2010/0034274 | A1 | 2/2010 | Li |
| 2010/0130607 | A1 | 5/2010 | Gold |
| 2010/0259906 | A1 | 10/2010 | Chang |
| 2010/0278879 | A1 | 11/2010 | Manku |
| 2010/0324327 | A1 | 12/2010 | Lee |
| 2011/0112196 | A1 | 5/2011 | Lukashev |
| 2012/0034274 | A1 | 2/2012 | Rupp |
| 2012/0165404 | A1 | 6/2012 | Lukashev |
| 2012/0259012 | A1 | 10/2012 | Lukashev |
| 2013/0115281 | A1 | 5/2013 | Draper et al. |
| 2013/0216615 | A1 | 8/2013 | Goldman |
| 2013/0259906 | A1 | 10/2013 | Rupp |
| 2013/0295169 | A1 | 11/2013 | Goldman |
| 2013/0302410 | A1 | 11/2013 | Gold |
| 2013/0303613 | A1 | 11/2013 | Lukashev |
| 2013/0315993 | A1 | 11/2013 | Nilsson |
| 2013/0316003 | A1 | 11/2013 | Nilsson |
| 2013/0317103 | A1 | 11/2013 | Lukashev |
| 2013/0324539 | A1 | 12/2013 | Annamalai |
| 2014/0037720 | A1 | 2/2014 | Nilsson |
| 2014/0037740 | A1 | 2/2014 | Nilsson |
| 2014/0056973 | A1 | 2/2014 | Virsik |
| 2014/0056978 | A1 | 2/2014 | Karaborni |
| 2014/0057917 | A1 | 2/2014 | Virsik |
| 2014/0057918 | A1 | 2/2014 | Shreeniwas |
| 2014/0065211 | A1 | 3/2014 | Karaborni |
| 2014/0066505 | A1 | 3/2014 | Joshi |
| 2014/0099364 | A2 | 4/2014 | Nilsson |
| 2014/0163100 | A1 | 6/2014 | Dawson |
| 2014/0179779 | A1 | 6/2014 | Chao |
| 2014/0193495 | A1 | 7/2014 | Nilsson |
| 2014/0199386 | A1 | 7/2014 | Nilsson |
| 2014/0199387 | A1 | 7/2014 | Nilsson |
| 2014/0199388 | A1 | 7/2014 | Nilsson |
| 2014/0199390 | A1 | 7/2014 | Nilsson |
| 2014/0199392 | A1 | 7/2014 | Nilsson |
| 2014/0199393 | A1 | 7/2014 | Nilsson |
| 2014/0200272 | A1 | 7/2014 | Nilsson |
| 2014/0200273 | A1 | 7/2014 | Nilsson |
| 2014/0200363 | A1 | 7/2014 | Irdam |
| 2014/0205659 | A1 | 7/2014 | Nilsson |
| 2014/0275048 | A1 | 9/2014 | Sanrame |
| 2014/0275205 | A1 | 9/2014 | Sanrame |
| 2014/0275250 | A1 | 9/2014 | Cundy |
| 2014/0323570 | A1 | 10/2014 | Gold |
| 2014/0348914 | A9 | 11/2014 | Karaborni |
| 2014/0348915 | A9 | 11/2014 | Karaborni |
| 2014/0350018 | A9 | 11/2014 | Virsik |
| 2014/0378542 | A1 | 12/2014 | Karaborni |
| 2015/0024049 | A1 | 1/2015 | Nilsson |
| 2015/0079180 | A1 | 3/2015 | Karaborni |
| 2015/0132747 | A1 | 5/2015 | Lukashev |
| 2015/0190360 | A1 | 7/2015 | Cundy |
| 2015/0209318 | A1 | 7/2015 | Goldman |
| 2015/0246016 | A1 | 9/2015 | Fatmi |
| 2015/0252013 | A1 | 9/2015 | Annamalai |
| 2015/0307914 | A9 | 10/2015 | Virsik |
| 2015/0366803 | A1 | 12/2015 | O Neill |
| 2016/0101059 | A1 | 4/2016 | Fatmi |
| 2016/0199335 | A1 | 7/2016 | Fatmi |
| 2016/0199336 | A1 | 7/2016 | Fatmi |
| 2017/0056359 | A1 | 3/2017 | Hughey |
| 2017/0056360 | A1 | 3/2017 | Hughey |
| 2017/0071891 | A1 | 3/2017 | Fatmi |
| 2017/0100360 | A1 | 4/2017 | Fatmi |
| 2017/0100361 | A1 | 4/2017 | Hughey |
| 2017/0100362 | A1 | 4/2017 | Hughey |
| 2017/0231942 | A1 | 8/2017 | Vaughn et al. |
| 2019/0015372 | A1 * | 1/2019 | Vaughn ................ A61K 9/4875 |
| 2019/0015373 | A1 * | 1/2019 | Vaughn ................ A61K 31/225 |
| 2019/0015374 | A1 * | 1/2019 | Dyakonov ............ A61K 9/4866 |

FOREIGN PATENT DOCUMENTS

| | | |
|---|---|---|
| WO | 2000030622 A2 | 6/2000 |
| WO | 2002055063 A2 | 7/2002 |
| WO | 2002055066 A1 | 7/2002 |
| WO | 2002055067 A2 | 7/2002 |
| WO | 2004030658 A1 | 4/2004 |
| WO | 2005009409 A2 | 2/2005 |
| WO | 2005023241 A1 | 3/2005 |
| WO | 2006023629 A2 | 3/2006 |
| WO | 2006023649 A2 | 3/2006 |
| WO | 2006023651 A2 | 3/2006 |
| WO | 2006036371 A2 | 4/2006 |
| WO | 2006037342 A2 | 4/2006 |
| WO | 2007042034 A1 | 4/2007 |
| WO | 2007042035 A2 | 4/2007 |
| WO | 2008096271 A2 | 8/2008 |
| WO | 2010022177 A2 | 2/2010 |
| WO | 2010079222 A1 | 7/2010 |
| WO | 2010126605 A1 | 11/2010 |
| WO | 2012013331 A2 | 2/2012 |
| WO | 2012162669 A1 | 11/2012 |
| WO | 2012170923 A1 | 12/2012 |
| WO | 2013076216 A1 | 5/2013 |
| WO | 2013090799 A1 | 6/2013 |
| WO | 2013092269 A1 | 6/2013 |
| WO | 2013112859 A1 | 8/2013 |
| WO | 2013119677 A1 | 8/2013 |
| WO | 2013148690 A1 | 10/2013 |
| WO | 2013158969 A1 | 10/2013 |
| WO | 2014028299 A1 | 2/2014 |
| WO | 2014031844 A1 | 2/2014 |
| WO | 2014031892 A1 | 2/2014 |
| WO | 2014031894 A1 | 2/2014 |
| WO | 2014031897 A1 | 2/2014 |
| WO | 2014031901 A1 | 2/2014 |
| WO | 2014143146 A1 | 9/2014 |
| WO | 2014190056 A2 | 11/2014 |
| WO | 2014197860 A1 | 12/2014 |
| WO | 2015017762 A1 | 2/2015 |
| WO | 2015028472 A1 | 3/2015 |
| WO | 2015028473 A1 | 3/2015 |
| WO | 2015042294 A1 | 3/2015 |
| WO | 2015044853 A2 | 4/2015 |

(56) References Cited

FOREIGN PATENT DOCUMENTS

| WO | 2015086467 A1 | 6/2015 |
| WO | 2015089420 A1 | 6/2015 |
| WO | 2015105757 A1 | 7/2015 |
| WO | 2015128492 A1 | 9/2015 |
| WO | 2015130998 A1 | 9/2015 |
| WO | 2016057133 A1 | 4/2016 |
| WO | 2017040272 A1 | 3/2017 |

OTHER PUBLICATIONS

Gullapalli, Journal of Pharmaceutical Science 99(10) 4107-4148 (2010).

Kappos et al., "BG00012, a novel oral fumarate, is effective in patients with relapsing-remitting multiple sclerosis", Multiple Sclerosis 2(Suppl. 1):S85 (2006).

Schilling et al., "Fumaric acid esters are effective in chronic experimental autoimmune encephalomyelitis and suppress macrophage infiltration," Clinical and Experimental Immunology 145(1):101-107 (2006).

Schimrigk et al., "Oral fumaric acid esters for the treatment of active multiple sclerosis: an open-label, baseline-controlled pilot study," European J. Neurology 13(6): 604-610 (2006).

Sheikh et al., "Tolerability and pharmacokinetics of delayed-release dimethyl fumarate administered with and without aspirin in healthy volunteers," Clinical Therapeutics 35(10): 1582-1594 (2013).

TECFIDERA® Prescribing Information Mar. 2013 (BIOGEN IDEC).

Verma, R.K., et al., "Formulation Aspects in the Development of Osmotically Controlled Oral Drug Delivery Systems," Journal of Controlled Release, 79: 7-27 (2002).

Yeh et al., "Effect of Medium-Chain Glycerides on Physiological Properties of Rabbit Intestinal Epitheliun1 in Vitro," Pharma. Res. 11(8): 1148-1154 (1994).

Canadian Patent Office Action for Application No. 2,962,916 dated Jul. 16, 2020 (4 pages).

* cited by examiner

FUMARATE ESTER PHARMACEUTICAL COMPOSITIONS

CROSS REFERENCE TO RELATED APPLICATIONS

This application is a continuation of U.S. patent application Ser. No. 15/730,832, filed on Oct. 12, 2017, which is a divisional of U.S. patent application Ser. No. 15/358,349, filed Nov. 22, 2016, which is a divisional of U.S. patent application Ser. No. 15/073,720, filed on Mar. 18, 2016, which is a divisional of U.S. patent application Ser. No. 14/840,072, filed on Aug. 31, 2015, which is a continuation-in-part of U.S. patent application Ser. No. 14/633,164, and International Patent Application No. PCT/US2015/017893, both filed on Feb. 27, 2015, each of which claim priority to U.S. Provisional Patent Application Nos. 62/061,185, filed on Oct. 8, 2014, 62/011,604, filed on Jun. 13, 2014, 61/950,648, filed on Mar. 10, 2014; and 61/946,233, filed on Feb. 28, 2014; and each of which is incorporated herein in its entirety by express reference thereto.

TECHNICAL FIELD

Described herein are pharmaceutical compositions comprising fumarate esters, methods for making the same, and methods for treating subjects in need thereof. In particular, oral pharmaceutical compositions comprising fumarate esters are described.

BACKGROUND

Fumaric acid esters (FAE; fumarate esters, e.g., alkyl or dialkyl fumarate esters such as dimethyl fumarate or monomethyl fumarate) are pharmacologically active substances used for treating hyperproliferative, inflammatory, or autoimmune disorders. They were first used to treat psoriasis and were licensed for this indication in Germany in 1995 as Fumaderm® (Biogen Idec, Inc., Cambridge, Mass., USA). Fumaderm® produces various undesirable side effects, including flushing, headaches, dizziness, eructation, nausea, vomiting, abdominal and intestinal cramps, and diarrhea. High concentrations of the drug released in the stomach are believed to be responsible for such side effects.

After oral intake, the main component of Fumaderm®, dimethyl fumarate (DMF), is hydrolysed by esterases to monomethyl fumarate (MMF), the bioactive metabolite. After absorption in the small intestine, MMF is believed to interact with immunocytes in the bloodstream. The primary plasma metabolites of DMF are monomethyl fumarate, fumaric acid, citric acid, and glucose. Monomethyl fumarate is further metabolized in the tricarboxylic acid cycle to carbon dioxide and water.

An improved oral formulation of DMF was developed and approved for the treatment of multiple sclerosis. This formulation, TECFIDERA® (Biogen Idec, Inc.), is available as hard gelatin delayed-release capsules containing 120 mg or 240 mg of granulated dimethyl fumarate enterically coated minitablets. See International Patent Application Publication No. WO 2013/119677 and U.S. Pat. No. 6,509,376. TECFIDERA® was intended to reduce the undesirable side effects by preventing release of DMF in the stomach.

The enterically coated DMF granules in TECFIDERA®, however, lack uniformity in shape and size, and the enteric coating may not be evenly distributed over the minitablets. This lack of homogeneity can diminish the enteric properties and affect the acid-resistance, dissolution, and release rates. In addition, the integrity of the acid-resistant coating fails when the coating cracks or flakes off. This leads to DMF release in the stomach and can cause flushing and the negative gastrointestinal side effects.

A subject's stomach content also affects delivery of DMF from TECFIDERA®. A meal was shown to decrease $C_{max}$ by 40% and delay $T_{max}$ from 2.0 hours to 5.5 hours; the AUC was unaffected. See WO 2006/037342. A reduction in the incidence of flushing by approximately 25% in the postprandial state was also observed. See TECFIDERA® Prescribing Information 03/2013 (Biogen Idec Inc.).

In addition, DMF sublimes at relatively low temperatures. About 15-20% of the DMF active ingredient is lost owing to sublimation during the wet-granulation processing used to manufacture TECFIDERA®. See WO 2013/076216. Sublimation also causes loss of DMF during storage and unused TECFIDERA® capsules must be discarded 90 days after a bottle of the capsules is opened.

Accordingly, it is desirable to develop oral controlled release formulations of fumarate esters that: (1) prevent flushing and the undesirable GI side effects associated with oral administration of fumarate esters; (2) reduce or eliminate fumarate ester sublimation during manufacturing and storage; (3) increase the long-term stability of the pharmaceutical composition; and (4) provide a variety of different release profiles, dosage forms, and dosing regimens.

SUMMARY

Described herein are controlled release pharmaceutical compositions comprising one or more fumarate esters suspended in a lipid or lipophilic matrix. The pharmaceutical composition is encapsulated in an enteric soft capsule. The oral enteric soft capsules comprising controlled release matrix compositions prevent release of the fumarate ester active ingredient in the gastric environment, but release the active ingredient in the intestine in a controlled manner. The compositions can be tailored to provide one or more release profiles, including immediate release, controlled release, delayed release, or extended release pharmacokinetics by the composition of the matrix fill. The formulations described herein comprise solid micronized particles of fumarate esters suspended in a matrix. The controlled release enteric capsule comprising a matrix of fumarate esters reduce, ameliorate, or eliminate the undesirable gastrointestinal side effects observed with prior fumarate ester pharmaceuticals. Further, the formulations preclude or reduce sublimation of the fumarate ester during manufacturing and storage.

One embodiment described herein is an oral pharmaceutical composition comprising a controlled release composition of one or more fumarate esters, including, but not limited to, dialkyl fumarates, alkyl fumarates, dimethyl fumarate (DMF), monomethyl fumarate (MMF), or combinations thereof. In one embodiment, the pharmaceutical composition comprises a controlled release enteric soft capsule shell encapsulating a matrix comprising one or more fumarate esters. In one aspect, the matrix comprises a lipid or lipophilic vehicle, a neutralizing agent, and solid particles of fumarate esters. In another aspect, the matrix comprises a lipid or lipophilic vehicle, a neutralizing agent, excipients, and solid particles of a fumarate ester. In another aspect, the matrix comprises a lipid or lipophilic vehicle, a neutralizing agent, surfactants, and solid particles of a fumarate ester. In one aspect, the lipid or lipophilic vehicle comprises polyvinylpyrrolidones, mono- and di-glycerides, and oils. In another aspect, the surfactant can comprise polysorbate 80 or polyoxyl 40 hydrogenated castor oil. In another aspect, the solid particles of fumarate ester comprise milled or micronized particles. In another aspect, the milled or micronized particles of one or more fumarate esters comprise mean particle distribution sizes of about 20 µm to about 300 µm, including all integers within the specified range. In another aspect, the solid particles of fumarate esters comprise mean particle distribution sizes of about 65 µm to about 260 µm, including all integers within the specified range. In another aspect, the solid microparticles of fumarate esters have mean particle distribution sizes of less than 260 µm. In another aspect, the solid particles of fumarate esters have mean particle distribution sizes of about 100 µm. In another aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, or esters or salts thereof, or combinations thereof. In another aspect, the matrix comprises one or more fumarate esters, a mixture of mono- and di-glycerides, polyvinylpyrrolidone, polyoxyl 40 hydrogenated castor oil, and lactic acid.

In another embodiment, the pharmaceutical composition comprises a matrix fill comprising about 10% to about 64% by weight of one or more fumarate esters (FAE; PSD d90≤100 µm); about 18% to about 70% by weight of a mixture of mono- and di-glycerides; at least about 1% to about 10% by weight polyvinylpyrrolidone; at least about 1% to about 10% by weight polyoxyl 40 hydrogenated castor oil, and at least about 1% to about 5% by weight lactic acid.

In another embodiment, the pharmaceutical composition comprises a matrix fill comprising about 29% by weight of one or more fumarate esters (FAE; PSD d90≤100 µm); about 54% by weight of a mixture of mono- and di-glycerides; about 3% by weight polyvinylpyrrolidone; about 10% by weight polyoxyl 40 hydrogenated castor oil, and about 5% by weight lactic acid. In one aspect, the composition has controlled release, delayed release, or extended release properties. In one aspect, the composition comprises one or more FAEs in an amount of about 80 mg to about 480 mg. In one aspect, the one or more FAEs comprise about 90 mg to about 120 mg. In one aspect, the composition comprises one or more FAEs in an amount of about 180 mg to about 240 mg. In one aspect, the one or more FAEs in an amount of about 360 mg to about 480 mg. In one aspect, the composition comprises one or more FAEs in an amount of about 80 mg FAE, about 85 mg FAE, about 90 mg FAE, about 95 mg FAE, about 100 mg FAE, about 105 mg FAE, about 110 mg FAE, about 115 mg FAE, about 120 mg FAE, about 125 mg FAE, about 130 mg FAE, about 135 mg FAE, about 140 mg FAE, about 145 mg FAE, about 150 mg FAE, about 155 mg FAE, about 160 mg FAE, about 165 mg FAE, about 170 mg FAE, about 175 mg FAE, about 180 mg FAE, about 185 mg FAE, about 190 mg FAE, about 195 mg FAE, about 200 mg FAE, about 205 mg FAE, about 210 mg FAE, about 215 mg FAE, about 220 mg FAE, about 225 mg FAE, about 230 mg FAE, about 235 mg FAE, about 240 mg FAE, about 245 mg FAE, about 250 mg FAE, about 255 mg FAE, about 260 mg FAE, about 265 mg FAE, about 270 mg FAE, about 275 mg FAE, about 280 mg FAE, about 285 mg FAE, about 290 mg FAE, about 295 mg FAE, about 300 mg FAE, about 305 mg FAE, about 310 mg FAE, about 315 mg FAE, about 320 mg FAE, about 325 mg FAE, about 330 mg FAE, about 335 mg FAE, about 340 mg FAE, about 345 mg FAE, about 350 mg FAE, about 355 mg FAE, about 360 mg FAE, about 365 mg FAE, about 370 mg FAE, about 375 mg FAE, about 380 mg FAE, about 385 mg FAE, about 390 mg FAE, about 395 mg FAE, about 400 mg FAE, about 405 mg FAE, about 410 mg FAE, about 415 mg FAE, about 420 mg FAE, about 425 mg FAE, about 430 mg FAE, about 435 mg FAE, about 440 mg FAE, about 445 mg FAE, about 450 mg FAE, about 455 mg FAE, about 460 mg FAE, about 465 mg FAE, about 470 mg FAE, about 475 mg FAE, or about 480 mg FAE. In one aspect, the composition comprises one or more FAEs in an amount of about 0.5 mmol to about 4.0 mmol FAE. In another aspect, the composition comprises one or more FAEs in an amount of about 0.7 mmol to about 3.7 mmol FAE. In another aspect, the composition comprises DMF, MMF, or a combination thereof. In another aspect, the composition comprises DMF. In another aspect, the composition further comprises one or more non-steroidal anti-inflammatory drugs (NSAIDS). In one aspect, the composition prevents sublimation of the fumarate ester during manufacturing. In another aspect, the composition prophylactically reduces the onset or ameliorates the symptoms of any flushing side effects. In another aspect, the composition reduces the onset or ameliorates the severity of any gastrointestinal side effects. In another aspect, the composition is stable for at least 1 year at conditions comprising 25° C. and 60% relative humidity. In another aspect, the composition is stable for at least 2 years at conditions comprising 25° C. and 60% relative humidity.

In one embodiment, the enteric soft capsule shell comprises one or more enteric, acid-insoluble polymers, and in a preferred embodiment additionally includes a film-forming polymer, a plasticizer, an alkali-neutralizing agent, a solvent, and optionally, a coloring agent, a flavoring, or a pharmaceutical excipient.

In another embodiment, the enteric soft capsule shell comprises about 20% to about 36% by weight of at least one film-forming polymer; about 8% to about 20% by weight of at least one enteric, acid-insoluble polymer; about 15% to about 20% by weight of at least one plasticizer; about 1% to about 5% by weight of at least one alkali-neutralizing agent; about 20% to about 40% by weight of a solvent; optionally, about 1% to about 5% by weight of an opacifying agent; and optionally, about 0.05% to about 1% by weight of at least one coloring agent.

In another embodiment, the enteric soft capsule shell comprises about 30% of at least one film-forming polymer; about 10% by weight of at least one enteric, acid-insoluble polymer; about 20% by weight of at least one plasticizer; about 1% by weight of at least one alkali-neutralizing agent; about 37% by weight of a solvent; and optionally, about 1.5% by weight of an opacifying agent; and optionally, at least one coloring agent. In one aspect, the enteric soft capsule shell comprises gelatin, acrylic methacrylate copolymers, glycerol, triethyl citrate, ammonia, water, and titanium dioxide.

Another embodiment described herein is a method for manufacturing an oral enteric soft capsule shell encapsulating a matrix comprising a fumarate ester, the method comprising: (i) providing a matrix fill composition comprising any of the composition described herein; (ii) providing an enteric soft capsule shell composition comprising any of the composition described herein; (iii) casting the enteric soft capsule shell into films using heat-controlled drums or surfaces; and (iv) forming an enteric soft capsule shell encapsulating the matrix fill composition using rotary die encapsulation technology. In one aspect, the enteric soft capsule matrix comprises one or more fumarate esters produced by said method.

Another embodiment described herein is a method for manufacturing an oral enteric soft capsule shell encapsulating a matrix comprising a fumarate ester, the method comprising: (i) providing a matrix fill composition comprising: about 10% to about 64% by weight of one or more fumarate esters (FAE; PSD d90≤100 µm); about 18% to about 70% by weight of a mixture of mono- and di-glycerides; about 1% to about 10% by weight polyvinylpyrrolidone; about 2% to about 12% by weight polyoxyl 40 hydrogenated castor oil, and about 1% to about 5% by weight lactic acid; (ii) providing an enteric soft capsule shell composition comprising: about 20% to about 36% by weight of at least one film-forming polymer; about 8% to about 20% by weight of at least one enteric, acid-insoluble polymer; about 15% to about 20% by weight of at least one plasticizer; about 1% to about 5% by weight of at least one alkali-neutralizing agent; about 20% to about 40% by weight of a solvent; optionally, about 1% to about 5% by weight of an opacifying agent; and optionally, about 0.05% to about 1% by weight of at least one coloring agent; (iii) casting the enteric soft capsule shell into films using heat-controlled drums or surfaces; and (iv) forming an enteric soft capsule shell encapsulating the matrix fill composition using rotary die encapsulation technology.

Another embodiment described herein is an enteric soft capsule comprising a shell encapsulating a fumarate ester matrix, wherein the matrix comprises: about 10% to about 64% by weight of one or more fumarate esters (FAE; PSD: <100 µm); about 18% to about 70% by weight of mono- and di-glycerides; at least about 1% to about 7% by weight of polyvinylpyrrolidone; at least about 2% to about 10% by weight of polyoxyl 40 hydrogenated castor oil, and at least about 1% to about 5% by weight of lactic acid; and wherein the enteric soft capsule shell comprises: about 20% to about 36% by weight of at least one film-forming polymer; about 8% to about 20% by weight of at least one enteric, acid-insoluble polymer; about 15% to about 20% by weight of at least one plasticizer; about 1% to about 5% by weight of at least one alkali-neutralizing agent; about 20% to about 40% by weight of a solvent; optionally, about 1% to about 5% by weight of an opacifying agent; and optionally, about 0.05% to about 1% by weight of at least one coloring agent.

Another embodiment described herein is an enteric soft capsule comprising a shell encapsulating a fumarate ester matrix, wherein the matrix comprises: about 29% by weight of one or more fumarate esters (FAE; PSD d90≤100 µm); about 54% by weight of a mixture of mono- and di-glycerides; about 3% by weight polyvinylpyrrolidone; about 10% by weight polyoxyl 40 hydrogenated castor oil, and about 5% by weight lactic acid; and wherein the enteric soft capsule shell comprises: about 30% by weight of at least one film-forming polymer; about 10% by weight of at least one enteric, acid-insoluble polymer; about 20% by weight of at least one plasticizer; about 1% by weight of at least one alkali-neutralizing agent; about 37% by weight of a solvent; optionally, about 1.5% by weight of an opacifying agent; and optionally, at least one coloring agent. In another aspect, the composition comprises DMF, MMF, or a combination thereof. In another aspect, the composition comprises DMF. In one aspect, the enteric soft capsule comprising a fumarate ester is resistant to dissolution at about pH 1.2 for at least about 2 hours. In another aspect, the enteric soft capsule comprising a fumarate ester begins dissolution at pH of about 6.8 within about 10 minutes. In one aspect, the enteric soft capsule has immediate release, controlled release, delayed release, or extended release properties. In another aspect, the enteric soft capsule comprising a fumarate ester reduces the onset or ameliorates the severity of any flushing or gastrointestinal side effects.

Another embodiment described herein is a method for treating, retarding the progression of, delaying the onset of, prophylaxis of, amelioration of, or reducing the symptoms of multiple sclerosis or psoriasis, comprising administering to a subject in need thereof an oral pharmaceutical composition comprising a controlled release enteric soft capsule shell and matrix comprising a fumarate ester. In one aspect, the pharmaceutical composition comprises a controlled release enteric soft capsule comprising a formulation of fumarate ester. In another aspect, the composition comprises DMF, MMF, or a combination thereof. In another aspect, the composition comprises DMF.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising administering to a subject in need thereof an oral pharmaceutical composition comprising a controlled release formulation of a fumarate ester, wherein the subject achieves a reduction of annualized relapse rate relative to baseline without substantially experiencing one or more of flushing, abdominal pain, diarrhea, and nausea. In one aspect, the pharmaceutical composition comprises any of the compositions described herein. In another aspect, the composition comprises DMF, MMF, or a combination thereof. In another aspect, the composition comprises DMF.

Another embodiment described herein is an oral pharmaceutical composition as described herein that is useful for treating neurodegenerative disorders. In one aspect, the pharmaceutical composition is useful for treating multiple sclerosis or psoriasis. In one embodiment described herein, subjects that are administered the oral pharmaceutical composition as described herein exhibit a mean plasma monomethyl fumarate $T_{max}$ of from about 1.5 hours to about 3.5 hours.

Another embodiment described herein is an oral pharmaceutical composition useful for treating, retarding the progression of, delaying the onset of, prophylaxis of, amelioration of, or reducing the symptoms of general autoimmune or neurodegenerative disorders. In another aspect, the composition comprises DMF, MMF, or a combination thereof. In another aspect, the composition comprises DMF.

Another embodiment described herein is a method for treating, retarding the progression of, delaying the onset of, prophylaxis of, amelioration of, or reducing the symptoms of general autoimmune or neurodegenerative disorders. In another aspect, the composition comprises DMF, MMF, or a combination thereof. In another aspect, the composition comprises DMF.

Another embodiment described herein is an oral pharmaceutical composition comprising a controlled release composition comprising a formulation of a fumarate ester useful for treating, retarding the progression of, delaying the onset of, prophylaxis of, amelioration of, or reducing the symptoms of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behcet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome. In another aspect, the composition comprises DMF, MMF, or a combination thereof. In another aspect, the composition comprises DMF.

Another embodiment described herein is a method for treating, retarding the progression of, delaying the onset of, prophylaxis of, amelioration of, or reducing the symptoms of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behcet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome comprising administering to a subject in need thereof an oral controlled release pharmaceutical composition comprising a fumarate ester. In one embodiment described herein, the oral pharmaceutical composition comprises an enteric soft capsule shell and matrix comprising a fumarate ester. In one aspect, the pharmaceutical composition comprises a controlled release enteric soft capsule comprising a formulation of a fumarate ester. In another aspect, the pharmaceutical composition is an immediate release, delayed release, controlled release, or extended release formulation of a fumarate ester. In another aspect, the composition comprises DMF, MMF, or a combination thereof. In another aspect, the composition comprises DMF.

Another embodiment described herein is an oral pharmaceutical composition comprising a controlled release formulation of a fumarate ester. In one aspect, the composition is provided in a dosage form containing about 80 mg to about 120 mg of one or more fumarate esters, wherein subjects administered the dosage form four times daily exhibit one or more pharmacokinetic parameters comprising: (a) a mean plasma monomethyl fumarate $C_{max}$ ranging from about 0.4 mg/L to about 2.41 mg/L; or (b) a mean plasma monomethyl fumarate $AUC_{overall}$ ranging from about 3.2 h·mg/L to about 11.2 h·mg/L. In another aspect, the composition is provided in a dosage form containing about 120 mg to about 180 mg of one or more fumarate esters, wherein subjects administered the dosage form exhibit one or more pharmacokinetic parameters comprising: (a) a mean plasma monomethyl fumarate $C_{max}$ ranging from about 0.4 mg/L to about 2.41 mg/L; (b) a mean plasma monomethyl fumarate $AUC_{0 \to 12h}$ ranging from about 0.5 h·mg/L to about 2.5 h·mg/L; or (c) a mean $AUC_{0 \to \infty}$ ranging from about 0.5 h·mg/L to about 2.6 h·mg/L. In another aspect, the composition is provided in a dosage form containing a total amount of about 180 mg to about 240 mg of one or more fumarate esters, wherein subjects administered the dosage form twice-daily exhibit one or more pharmacokinetic parameters comprising: (a) a mean plasma monomethyl fumarate $C_{max}$ ranging from about 1.0 mg/L to about 3.4 mg/L; (b) a mean plasma monomethyl fumarate $AUC_{overall}$ ranging from about 4.81 h·mg/L to about 11.2 h·mg/L. In another aspect, the composition is provided in a dosage form containing about 180 mg to about 240 mg of one or more fumarate esters, wherein subjects administered the dosage form exhibit one or more pharmacokinetic parameters comprising: (a) a mean plasma monomethyl fumarate $C_{max}$ ranging from about 1.0 mg/L to about 3.4 mg/L; (b) a mean plasma monomethyl fumarate $AUC_{0 \to 42h}$ ranging from about 1.0 h·mg/L to about 5.5 h·mg/L; or (c) a mean $AUC_{0 \to \infty}$ ranging from about 1.0 h·mg/L to about 5.6 h·mg/L. In another aspect, the fumarate ester formulation is encapsulated in an enteric soft capsule. In another aspect, the composition comprises DMF, MMF, or a combination thereof. In another aspect, the composition comprises DMF.

Another embodiment described herein is an oral pharmaceutical composition comprising total amount of about 80 mg to about 120 mg of one or more fumarate esters, wherein subjects administered the capsule exhibit one or more pharmacokinetic parameters comprising: (a) a mean plasma monomethyl fumarate $T_{max}$ of from about 1.5 hours to about 3.5 hours; (b) a mean plasma monomethyl fumarate $C_{max}$ ranging from about 0.4 mg/L to about 2.41 mg/L; (c) a mean plasma monomethyl fumarate $AUC_{0\to12h}$ ranging from about 0.5 h·mg/L to about 2.5 h·mg/L; or (d) a mean $AUC_{0\to\infty}$ ranging from about 0.5 h·mg/L to about 2.6 h·mg/L. In another aspect, the composition comprises about 180 mg to about 240 mg of one or more fumarate esters, wherein subjects administered the capsule exhibit one or more pharmacokinetic parameters comprising: (a) a mean plasma monomethyl fumarate $T_{max}$ of from about 1.5 hours to about 3.5 hours; (b) a mean plasma monomethyl fumarate $C_{max}$ ranging from about 1.0 mg/L to about 3.4 mg/L; (c) a mean plasma monomethyl fumarate $AUC_{0\to12h}$ ranging from about 1.0 h·mg/L to about 5.5 h·mg/L; or (d) a mean $AUC_{0\to\infty}$ ranging from about 1.0 h·mg/L to about 5.6 h·mg/L. In one aspect, the composition comprises DMF, MMF, or a combination thereof. In another aspect, the composition comprises DMF.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of one or more fumarate esters comprising any of the compositions described herein and a therapeutically amount of one or more non-steroidal anti-inflammatory drugs effective to reduce flushing. In one aspect, the one or more non-steroidal anti-inflammatory drug is aspirin, ibuprofen, naproxene, diclofenac, ketoprofen, celecoxib, or a combination thereof.

Another embodiment described herein is a once or twice daily oral pharmaceutical composition comprising a delayed release, controlled release, or extended release formulation of a fumarate ester. In one aspect, the composition is provided in one or more dosage forms containing about 80 mg to about 480 mg of one or more fumarate esters, wherein subjects administered the dosage form once daily exhibit one or more pharmacokinetic parameters comprising: (a) a mean plasma monomethyl fumarate $C_{max}$ ranging from about 0.4 mg/L to about 5.2 mg/L; or (b) a mean plasma monomethyl fumarate $AUC_{0\to\infty}$ ranging from about 0.5 h·mg/L to about 15.5 h·mg/L. In another aspect, the composition is provided in one or more dosage forms containing about 80 mg to about 480 mg of one or more fumarate esters, wherein subjects administered the dosage form once daily exhibit one or more pharmacokinetic parameters comprising: (a) a mean plasma monomethyl fumarate $C_{max}$ ranging from about 0.4 mg/L to about 5.2 mg/L, (b) a mean plasma monomethyl fumarate $AUC_{0\to12h}$ ranging from about 0.5 h·mg/L to about 13.5 h·mg/L, or (c) a mean $AUC_{0\to\infty}$ ranging from about 0.5 h·mg/L to about 15.5 h·mg/L. In another aspect, the capsule contains a total amount of about 80 mg to about 480 mg of one or more fumarate esters, wherein subjects administered the one or more capsules exhibit one or more pharmacokinetic parameters comprising: (a) a mean plasma monomethyl fumarate $T_{max}$ of from about 1.5 hours to about 10.5 hours; (b) a mean plasma monomethyl fumarate $C_{max}$ ranging from about 0.4 mg/L to about 5.2 mg/L; (c) a mean plasma monomethyl fumarate $AUC_{0\to42h}$ ranging from about 0.5 h·mg/L to about 13.5 h·mg/L; or (d) a mean $AUC_{0\to\infty}$ ranging from about 0.5 h·mg/L to about 15.5 h·mg/L.

Another embodiment described herein is a pharmaceutical composition as described herein, for oral administration to a subject having multiple sclerosis containing one or more fumarate ester compounds, or pharmaceutically acceptable salts thereof that metabolize to monomethyl fumarate, wherein said administering the composition provides one or more of the following pharmacokinetic parameters: (a) a mean plasma monomethyl fumarate $T_{max}$ of from about 1.5 hours to about 3.5 hours; (b) a mean plasma monomethyl fumarate $C_{max}$ ranging from about 0.4 mg/L to about 3.4 mg/L; (c) a mean plasma monomethyl fumarate $AUC_{overall}$ ranging from about 3.2 h·mg/L to about 11.2 h·mg/L; (d) a mean plasma monomethyl fumarate $AUC_{0\to12h}$ ranging from about 0.5 h·mg/L to about 5.5 h·mg/L; or (e) a mean $AUC_{0\to\infty}$ ranging from about 0.5 h·mg/L to about 5.6 h·mg/L.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising administering to a subject in need thereof any one of the compositions of described herein, containing one or more fumarate ester compounds, or pharmaceutically acceptable salts thereof that metabolize to monomethyl fumarate, wherein said administering the composition provides one or more of the following pharmacokinetic parameters: (a) a mean plasma monomethyl fumarate $T_{max}$ of from about 1.5 hours to about 3.5 hours; (b) a mean plasma monomethyl fumarate $C_{max}$ ranging from about 0.4 mg/L to about 3.4 mg/L; (c) a mean plasma monomethyl fumarate $AUC_{overall}$ ranging from about 3.2 h·mg/L to about 11.2 h·mg/L; (d) a mean plasma monomethyl fumarate $AUC_{0\to12h}$ ranging from about 0.5 h·mg/L to about 5.5 h·mg/L; or (e) a mean $AUC_{0\to\infty}$ ranging from about 0.5 h·mg/L to about 5.6 h·mg/L.

Another embodiment described herein is a pharmaceutical composition as described herein, for oral administration to a subject having multiple sclerosis containing one or more fumarate ester compounds, or pharmaceutically acceptable salts thereof that metabolize to monomethyl fumarate, wherein said administering the composition provides one or more of the following pharmacokinetic parameters: (a) a mean plasma monomethyl fumarate $T_{max}$ of from about 1.5 hours to about 10.5 hours; (b) a mean plasma monomethyl fumarate $C_{max}$ ranging from about 0.4 mg/L to about 5.2 mg/L; (c) a mean plasma monomethyl fumarate $AUC_{0\to42h}$ ranging from about 0.5 h·mg/L to about 13.5 h·mg/L; or (d) a mean $AUC_{0\to\infty}$ ranging from about 0.5 h·mg/L to about 15.5 h·mg/L.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof any one of the compositions described herein comprising one or more fumarate ester compounds, or pharmaceutically acceptable salts thereof that metabolize to monomethyl fumarate, wherein said administering the composition provides one or more of the following pharmacokinetic parameters: (a) a mean plasma monomethyl fumarate $T_{max}$ of from about 1.5 hours to about 10.5 hours; (b) a mean plasma monomethyl fumarate $C_{max}$ ranging from about 0.4 mg/L to about 5.2 mg/L; (c) a mean plasma monomethyl fumarate $AUC_{overall}$ ranging from about 0.5 h·mg/L to about 15.2 h·mg/L; (d) a mean plasma monomethyl fumarate $AUC_{0\to12h}$ ranging from about 0.5 h·mg/L to about 13.5 h·mg/L; or (e) a mean $AUC_{0\to\infty}$ ranging from about 0.5 h·mg/L to about 15.5 h·mg/L. In one aspect, the composition comprises DMF, MMF, or a combination thereof. In another aspect, the composition comprises DMF.

Another embodiment described herein is a pharmaceutical composition comprising any one of the pharmaceutical compositions described herein for oral administration to a subject having multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject. In one aspect, the subject experiences one or more of flushing, abdominal pain, diarrhea, and nausea at a rate of less than about 10%. In another aspect, the subject is a child. In one aspect, the child is over 9 years of age.

Another embodiment described herein is a method for treating, retarding the progression of, delaying the onset of, prophylaxis of, amelioration of, or reducing the symptoms of multiple sclerosis, the method comprising the oral administration of a therapeutically effective amount of one or more fumarate esters comprising any one of the pharmaceutical compositions described herein, to a subject with multiple sclerosis, wherein the administration is sufficient to achieve a reduction of about 0.224 annualized relapse rate relative to baseline in the subject without substantially inducing one or more of flushing, abdominal pain, diarrhea, and nausea in the subject. In one aspect, the subject experiences one or more of flushing, abdominal pain, diarrhea, and nausea at a rate of less than about 10%. In another aspect, the subject is a child. In one aspect, the child is over 9 years of age.

Another embodiment described herein is a pharmaceutical composition comprising any one of the pharmaceutical compositions described herein for oral administration to a subject having multiple sclerosis, comprising a therapeutically effective amount of one or more fumarate esters, wherein the administration is sufficient to achieve a reduction of annualized relapse rate relative to baseline in the subject without substantially inducing one or more of flushing, abdominal pain, diarrhea, and nausea in the subject. In one aspect, the subject experiences one or more of flushing, abdominal pain, diarrhea, and nausea at a rate of less than about 10%. In another aspect, the subject is a child. In one aspect, the child is over 9 years of age.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, the method comprising the oral administration of a therapeutically effective amount of one or more fumarate esters comprising any one of the pharmaceutical compositions described herein to a subject in need thereof, wherein the subject achieves a reduction annualized relapse rate relative to baseline without substantially experiencing one or more of flushing, abdominal pain, diarrhea, and nausea. In one aspect, the subject experiences one or more of flushing, abdominal pain, diarrhea, and nausea at an incidence rate of less than about 10%. In another aspect, the subject is a child. In one aspect, the child is over 9 years of age.

Another embodiment described herein is a pharmaceutical composition comprising any one of the pharmaceutical compositions described herein, for oral administration to a subject having a general autoimmune or neurodegenerative disorder, including but not limited to multiple sclerosis, comprising a therapeutically effective amount of one or more fumarate esters, wherein the administration is sufficient to achieve a reduction of annualized relapse rate relative to baseline in the subject without substantially inducing one or more of flushing, abdominal pain, diarrhea, and nausea in the subject; and wherein the administration does not require titration of the pharmaceutical composition. In one aspect, the subject experiences one or more of flushing, abdominal pain, diarrhea, and nausea at an incidence rate of less than about 10%. In another aspect, the subject is a child. In one aspect, the child is over 9 years of age.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis, the method comprising the oral administration of a therapeutically effective amount of one or more fumarate esters comprising any one of the pharmaceutical compositions described herein, to a subject in need thereof, wherein the administration is sufficient to achieve a reduction of annualized relapse rate relative to baseline in the subject without substantially inducing one or more of flushing, abdominal pain, diarrhea, and nausea in the subject; and wherein the administration does not require titration of the pharmaceutical composition.

Another embodiment described herein is a pharmaceutical composition comprising any of the pharmaceutical compositions described herein for oral administration to a subject having a general autoimmune or neurodegenerative disorder, including but not limited to multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject and wherein the administration does not require titration of the pharmaceutical composition. In one aspect, the subject experiences one or more of flushing, abdominal pain, diarrhea, and nausea at a rate of less than about 10%. In another aspect, the subject is a child. In one aspect, the child is over 9 years of age.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis, the method comprising the oral administration of a therapeutically effective amount of one or more fumarate esters comprising any of the pharmaceutical compositions described herein to a subject in need thereof, wherein the administration is sufficient to achieve a reduction of about 0.224 annualized relapse rate relative to baseline in the subject without substantially inducing one or more of flushing, abdominal pain, diarrhea, and nausea in the subject and wherein the administration does not require titration of the pharmaceutical composition. In one aspect, the subject experiences one or more of flushing, abdominal pain, diarrhea, and nausea at an incidence rate of less than about 10%. In another aspect, the subject is a child. In one aspect, the child is over 9 years of age.

Another embodiment described herein is a pharmaceutical composition comprising any one of the pharmaceutical compositions described herein, for oral administration to a subject having a general autoimmune or neurodegenerative disorder, including but not limited to multiple sclerosis or psoriasis, comprising a therapeutically effective amount of one or more fumarate esters, wherein the subject achieves a reduction of annualized relapse rate relative to baseline without substantially experiencing one or more of flushing, abdominal pain, diarrhea, and nausea in the subject and wherein the administration does not require titration of the pharmaceutical composition.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, the method comprising the oral administration of a therapeutically effective amount of one or more fumarate esters comprising any one of the pharmaceutical compositions described herein, to a subject in need thereof, wherein the subject achieves a reduction of annualized relapse rate relative to baseline without substantially experiencing one or more of flushing, abdominal pain, diarrhea, and nausea in the subject and wherein the administration does not require titration of the pharmaceutical composition.

Another embodiment described herein is an oral pharmaceutical composition comprising any of the compositions described herein for administration to a subject having a general autoimmune or neurodegenerative disorder, including but not limited to multiple sclerosis or psoriasis, comprising a therapeutically effective amount of one or more fumarate esters, wherein the pharmaceutical composition is stable at 25° C. and 60% RH for at least 1 year.

Another embodiment described herein is an oral pharmaceutical composition comprising any of the compositions described herein comprising a therapeutically effective amount of one or more fumarate esters for administration to a subject diagnosed with multiple sclerosis or psoriasis.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of one or more fumarate esters comprising any of the pharmaceutical compositions described herein.

Another embodiment described herein is a pharmaceutical composition comprising any one of the compositions described herein, for oral administration to a subject of less than 17 years of age having a general autoimmune or neurodegenerative disorder, including but not limited to multiple sclerosis or psoriasis, comprising a therapeutically effective amount of one or more fumarate esters.

Another embodiment described herein is a method for treating, retarding the progression of, delaying the onset of, prophylaxis of, amelioration of, or reducing the symptoms of a subject of less than 17 years of age having a general autoimmune or neurodegenerative disorder, including but not limited to multiple sclerosis or psoriasis, comprising orally administering to a subject in need thereof having an age less than 17 a therapeutically effective amount of one or more fumarate esters comprising any one of the pharmaceutical compositions described herein.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the pharmaceutical compositions described herein and a therapeutically effective amount of a leukotriene receptor antagonist. In one aspect, the leukotriene receptor antagonist comprises montelukast or zafirlukast.

Another embodiment described herein is a pharmaceutical composition comprising a matrix fill comprising any of the compositions described herein in Tables 1, 2, 5-24, and 26-28.

Another embodiment described herein is a pharmaceutical composition for treating, retarding the progression of, delaying the onset of, prophylaxis of, amelioration of, or reducing the symptoms of a general autoimmune or neurodegenerative disorder, including but not limited to multiple sclerosis or psoriasis, comprising a fumarate ester, wherein the pharmaceutical composition exhibits an in vitro dissolution rate (% dissolution per minute) at pH 6.8, as shown in any of Drawings 2-14 described herein.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of one or more fumarate esters comprising any of the pharmaceutical compositions described herein, wherein the composition exhibits an in vitro dissolution rate (% dissolution per minute) at pH 6.8, as shown in any of Drawings 2-14 described herein.

Another embodiment described herein is an oral pharmaceutical composition for treating, retarding the progression of, delaying the onset of, prophylaxis of, amelioration of, or reducing the symptoms of general autoimmune or neurodegenerative disorders, including but not limited to multiple sclerosis or psoriasis, comprising one or more fumarate esters, wherein the pharmaceutical composition exhibits a plasma monomethyl fumarate $C_{max}$ of about 1321.3±618.9 ng/mL.

Another embodiment described herein is a method for treating, retarding the progression of, delaying the onset of, prophylaxis of, amelioration of, or reducing the symptoms of general autoimmune or neurodegenerative disorders, including but not limited to multiple sclerosis or psoriasis, comprising orally administering to a subject in need thereof a therapeutically effective amount of one or more fumarate esters comprising any of the pharmaceutical compositions described herein, wherein the pharmaceutical composition exhibits a plasma monomethyl fumarate $C_{max}$ of about 1321.3±618.9 ng/mL.

Another embodiment described herein is an oral pharmaceutical composition for treating, retarding the progression of, delaying the onset of, prophylaxis of, amelioration of, or reducing the symptoms of general autoimmune or neurodegenerative disorders, including but not limited to multiple sclerosis or psoriasis, comprising one or more fumarate esters, wherein the pharmaceutical composition exhibits a plasma monomethyl fumarate $C_{max}$ as shown herein in Drawing 15.

Another embodiment described herein is a method for treating, retarding the progression of, delaying the onset of, prophylaxis of, amelioration of, or reducing the symptoms of general autoimmune or neurodegenerative disorders, including but not limited to multiple sclerosis or psoriasis, comprising orally administering to a subject in need thereof a therapeutically effective amount of one or more fumarate esters comprising any of the pharmaceutical compositions described herein, wherein the pharmaceutical composition exhibits a plasma monomethyl fumarate $C_{max}$ as shown herein in Drawing 15.

Another embodiment described herein is an oral pharmaceutical composition for treating, retarding the progression of, delaying the onset of, prophylaxis of, amelioration of, or reducing the symptoms of a general autoimmune or neurodegenerative disorder, including but not limited to multiple sclerosis or psoriasis, comprising one or more fumarate esters, wherein the pharmaceutical composition exhibits an in vitro dissolution rate at pH 6.8 comprising about 10% to about 80% dissolution after about 10 minutes to about 480 minutes.

Another embodiment described herein is a method for treating, retarding the progression of, delaying the onset of, prophylaxis of, amelioration of, or reducing the symptoms of general autoimmune or neurodegenerative disorders, including but not limited to multiple sclerosis or psoriasis, comprising orally administering to a subject in need thereof a therapeutically effective amount of one or more fumarate esters comprising any of the pharmaceutical compositions described herein, wherein the pharmaceutical composition is administered without titration of the pharmaceutical composition and without substantially inducing one or more of flushing, abdominal pain, diarrhea, and nausea in the subject.

Another embodiment described herein is an oral pharmaceutical composition for treating, retarding the progression of, delaying the onset of, prophylaxis of, amelioration of, or reducing the symptoms of general autoimmune or neurodegenerative disorders, comprising one or more fumarate esters, wherein the pharmaceutical composition is administered without titration of the pharmaceutical composition and without substantially inducing one or more of flushing, abdominal pain, diarrhea, and nausea in the subject.

Another embodiment described herein is an oral pharmaceutical composition comprising a controlled release enteric soft capsule shell encapsulating a matrix comprising: about 10% to about 64% by weight of one or more fumarate esters (FAE; PSD d90≤100 µm); about 18% to about 70% by weight of a mixture of mono- and di-glycerides; about 3% by weight of polyvinylpyrrolidone; about 10% by weight of polyoxyl 40 hydrogenated castor oil, and about 5% by weight of lactic acid. In one aspect, the matrix comprises about 13% to about 16%; about 27% to about 32%; or about 53% to about 64%, each by weight of one or more FAEs. In another aspect, the mixture of mono- and di-glycerides is present in an amount of about 66% to about 69%; about 50% to about 55%; or about 18% to about 29%, each by weight. In another aspect, the one or more FAEs comprise about 80 mg to about 480 mg FAE. In another aspect, the matrix comprises about 80 mg to about 105 mg FAE, about 90 mg to about 110 mg FAE, about 95 mg to about 115 mg FAE, about 100 mg to about 120 mg FAE; about 180 mg to about 230 mg FAE; about 200 mg to about 240 mg FAE; about 270 mg to about 360 mg FAE; about 360 mg to about 480 mg FAE; or about 400 to about 480 mg FAE. In another aspect, the matrix comprises about 90 mg to about 120 mg FAE. In another aspect, the matrix comprises about 180 mg to about 230 mg FAE. In another aspect, the matrix comprises about 200 mg to about 220 mg FAE. In another aspect, the matrix comprises about 215 mg FAE. In another aspect, the matrix comprises about 0.5 to about 3.5 mmol FAE. In another aspect, the matrix comprises about 0.6 to about 1.7 mmol FAE. In another aspect, the matrix comprises DMF, MMF, or a combination thereof. In another aspect, the matrix comprises DMF.

Another embodiment described herein is a method of treating multiple sclerosis in a subject in need thereof comprising orally administering to the subject one or more doses of a composition comprising one or more fumarate esters in an amount of about 90 mg to about 120 mg FAE or about 180 mg to about 240 mg FAE, wherein the one or more doses comprise a controlled release pharmaceutical composition that releases the contents at a physiological pH of about pH 6.8.

Another embodiment described herein is a method of treating multiple sclerosis in a subject in need thereof comprising orally administering to the subject one or more doses of one or more fumarate esters comprising about 90 mg to about 120 mg FAE or about 180 mg to about 240 mg FAE wherein the FAE comprises a prodrug of methyl hydrogen fumarate or methyl hydrogen fumarate.

Another embodiment described herein is a method of treating multiple sclerosis in a subject in need thereof comprising orally administering to the subject one or more doses of one or more fumarate esters wherein methyl hydrogen fumarate activates a nuclear erythroid 2-related factor 2 (nuclear factor erythroid-derived 2-like 2; Nrf2) transcriptional pathway. In one aspect, the dose comprises an oral controlled release composition comprising: about 10% to about 64% by weight of one or more fumarate esters (FAE; PSD d90≤100 µm); about 18% to about 70% by weight of a mixture of mono- and di-glycerides; about 3% by weight of polyvinylpyrrolidone; about 10% by weight of polyoxyl 40 hydrogenated castor oil, and about 5% by weight of lactic acid. In another aspect, the dose comprises one or more FAEs in an amount of about 80 mg to about 480 mg. In another aspect, the dose comprises one or more FAEs in an amount of about 80 mg to about 120 mg. In another aspect, the dose comprises one or more FAEs in an amount of about 180 mg to about 240 mg. In another aspect, a daily total dose comprises one or more FAEs in an amount of about 360 mg to about 480 mg. In another aspect, the fumarate ester comprises MMF, DMF, or a combination thereof. In another aspect, the fumarate ester comprises DMF.

Another embodiment described herein is an oral controlled release pharmaceutical composition comprising a soft capsule shell and a matrix, the matrix comprising about 10% to about 64% by weight of one or more fumarate esters (FAE; PSD d90≤100 µm); about 18% to about 70% by weight of a mixture of mono- and di-glycerides; about 1% to about 10% by weight polyvinylpyrrolidone; about 2% to about 10% by weight polyoxyl 40 hydrogenated castor oil, and about 1% to about 5% by weight lactic acid. In one aspect, the soft capsule shell is an enteric soft capsule comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is a method of treating multiple sclerosis in a subject in need thereof comprising orally administering to the subject one or more doses of an oral controlled release pharmaceutical composition comprising a soft capsule shell and a matrix, the matrix comprising about 10% to about 64% by weight of one or more fumarate esters (FAE; PSD d90≤100 µm); about 18% to about 70% by weight of a mixture of mono- and di-glycerides; about 1% to about 10% by weight polyvinylpyrrolidone; about 2% to about 10% by weight polyoxyl 40 hydrogenated castor oil, and about 1% to about 5% by weight lactic acid.

Another embodiment described herein is an oral controlled release pharmaceutical composition comprising a soft capsule shell and a matrix, the matrix comprising about 28% by weight of FAE; about 53% by weight of a mixture of mono- and di-glycerides; about 10% by weight of polyvinylpyrrolidone; about 3% by weight of polyoxyl 40 hydrogenated castor oil, and about 5% by weight of lactic acid. In one aspect, the soft capsule shell is an enteric soft capsule shell comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is method of treating multiple sclerosis in a subject in need thereof comprising orally administering to the subject one or more doses of an oral controlled release pharmaceutical composition comprising a soft capsule shell and a matrix, the matrix comprising about 28% by weight of FAE; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is a method of treating multiple sclerosis in a subject in need thereof comprising orally administering to the subject one or more doses of an oral controlled release pharmaceutical composition comprising a soft capsule shell and a matrix, the matrix comprising about 28% by weight of DMF; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is an oral controlled release pharmaceutical composition comprising a soft capsule shell and a matrix, the matrix comprising about 75 mg, about 80 mg, about 85 mg, about 90 mg, about 95 mg, about 100 mg, about 105 mg, about 108 mg, about 110 mg, about 115 mg, about 120 mg, about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg of FAE; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is an oral controlled release pharmaceutical composition comprising a soft capsule shell and a matrix, the matrix comprising about 75 mg, about 80 mg, about 85 mg, about 90 mg, about 95 mg, about 100 mg, about 105 mg, about 108 mg, about 110 mg, about 115 mg, about 120 mg, about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg of DMF; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is an oral controlled release pharmaceutical composition dosage form comprising a daily total amount of FAE of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is an oral controlled release pharmaceutical composition dosage form comprising a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is an oral pharmaceutical composition providing a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg DMF; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is a method of treating multiple sclerosis in a subject in need thereof comprising orally administering to the subject one or more doses of a pharmaceutical composition providing a daily total amount of FAE of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is a method of treating multiple sclerosis in a subject in need thereof comprising orally administering to the subject one or more doses of a pharmaceutical composition providing a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is an oral pharmaceutical composition comprising a controlled release enteric soft capsule shell and matrix comprising: about 10% to about 64% of one or more fumarate esters (FAE; PSD<100 µm); about 18% to about 70% by weight of a mixture of mono- and di-glycerides; at least about 3% by weight of polyvinylpyrrolidone; at least about 10% by weight of polyoxyl 40 hydrogenated castor oil, and at least about 5% by weight of lactic acid. In one aspect, the composition comprises one or more FAEs in an amount of about 13% to about 16% by weight; about 27% to about 32% by weight; or about 53% to about 64% by weight. In another aspect, the composition comprises mono- and di-glycerides in an amount of about 66% to about 69% by weight; about 50% to about 55% by weight; or about 18% to about 29% by weight. In another aspect, the composition comprises one or more FAEs in an amount of about 80 mg to about 480 mg FAE. In another aspect, the composition comprises one or more FAEs in an amount of about 80 mg to about 100 mg FAE; about 90 mg to about 110 mg FAE, about 100 mg to about 120 mg FAE; about 180 mg to about 220 mg FAE; about 200 mg to about 240 mg FAE; or about 400 to about 480 mg FAE. In another aspect, the composition comprises one or more FAEs in an amount of about 90 mg to about 110 mg FAE. In another aspect, the composition comprises one or more FAEs in an amount of about 100 mg to about 120 mg FAE. In another aspect, the composition comprises one or more FAEs in an amount of about 200 mg to about 220 mg FAE. In another aspect, the composition comprises one or more FAEs in an amount of about 210 mg to about 220 mg FAE. In another aspect, the composition comprises one or more FAEs in an amount of about 215 mg FAE. In another aspect, the composition comprises one or more FAEs in an amount of about 1.5 to about 1.7 mmol FAE. In another aspect, the matrix comprises DMF, MMF, or a combination thereof. In another aspect, the matrix comprises DMF.

Another embodiment described herein is a method of treating multiple sclerosis in a subject in need thereof comprising orally administering to the subject one or more doses of one or more fumarate esters in an amount of about 180 mg to about 220 mg FAE, wherein the one or more doses comprise a controlled release pharmaceutical composition that releases the contents at a physiological pH of about pH 6.8.

Another embodiment described herein is a method of treating multiple sclerosis in a subject in need thereof comprising orally administering to the subject one or more doses of one or more fumarate esters in an amount of about 180 mg to about 220 mg FAE, wherein the FAE comprises a prodrug of methyl hydrogen fumarate or methyl hydrogen fumarate.

Another embodiment described herein is a method of treating multiple sclerosis in a subject in need thereof comprising orally administering to the subject one or more doses of one or more fumarate esters wherein methyl hydrogen fumarate activates a nuclear erythroid 2-related factor 2 (nuclear factor erythroid-derived 2-like 2; Nrf2) transcriptional pathway. In one aspect, the one or more doses of fumarate esters comprise an oral controlled release composition comprising: about 10% to about 64% by weight of one or more fumarate esters (FAE; PSD<100 μm); about 18% to about 70% by weight of a mixture of mono- and di-glycerides; at least about 3% by weight polyvinylpyrrolidone; at least about 10% by weight polyoxyl 40 hydrogenated castor oil, and at least about 5% by weight lactic acid. In another aspect, the dose comprises one or more FAEs in an amount of about 80 mg to about 480 mg. In another aspect, the dose comprises one or more FAEs in an amount of about 80 mg to about 120 mg. In another aspect, the dose comprises one or more FAEs in an amount of about 180 mg to about 240 mg. In another aspect, a daily total dose comprises one or more FAEs in an amount of about 360 mg to about 480 mg. In another aspect, the FAE comprises MMF, DMF, or a combination thereof. In another aspect, the FAE comprises DMF.

Another embodiment described herein is an oral controlled release pharmaceutical composition comprising a soft capsule and a matrix, the matrix comprising about 10% to about 64% by weight of one or more fumarate esters (FAE; PSD d90≤100 μm); about 18% to about 70% by weight of a mixture of mono- and di-glycerides; about 1% to about 10% by weight polyvinylpyrrolidone; about 2% to about 10% by weight polyoxyl 40 hydrogenated castor oil, and about 1% to about 5% by weight lactic acid. In one embodiment, the FAE is dimethyl fumarate. In one embodiment, the soft capsule is an enteric soft capsule shell comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is a method of treating multiple sclerosis in a subject in need thereof comprising orally administering to the subject one or more doses of an oral controlled release pharmaceutical composition comprising a soft capsule shell and a matrix, the matrix comprising about 10% to about 64% by weight of one or more fumarate esters (FAE; PSD d90≤100 μm); about 18% to about 70% by weight of a mixture of mono- and di-glycerides; about 1% to about 10% by weight polyvinylpyrrolidone; about 2% to about 10% by weight polyoxyl 40 hydrogenated castor oil, and about 1% to about 5% by weight lactic acid.

Another embodiment described herein is an oral controlled release pharmaceutical composition comprising a soft capsule shell and a matrix, the matrix comprising about 28% by weight of fumarate esters; about 53% by weight of a mixture of mono- and di-glycerides; about 10% by weight of polyvinylpyrrolidone; about 3% by weight of polyoxyl 40 hydrogenated castor oil, and about 5% by weight of lactic acid. In one embodiment, the fumarate ester is dimethyl fumarate. In one embodiment, the soft capsule is an enteric soft capsule comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is a method of treating multiple sclerosis in a subject in need thereof comprising orally administering to the subject one or more doses of an oral controlled release pharmaceutical composition comprising a soft capsule shell and a matrix, the matrix comprising about 28% by weight of fumarate esters; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is a method of treating multiple sclerosis in a subject in need thereof comprising orally administering to the subject one or more doses of an oral controlled release pharmaceutical composition comprising a soft capsule shell and a matrix, the matrix comprising about 28% by weight of DMF; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is an oral controlled release pharmaceutical composition comprising a soft capsule and a matrix, the matrix comprising about 75 mg, about 80 mg, about 85 mg, about 90 mg, about 95 mg, about 100 mg, about 105 mg, about 108 mg, about 110 mg, about 115 mg, about 120 mg, about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg of FAE and about 53% by weight of a mixture of mono- and di-glycerides; about 10% by weight of polyvinylpyrrolidone; about 3% by weight of polyoxyl 40 hydrogenated castor oil, and about 5% by weight of lactic acid. In one embodiment, the soft capsule is an enteric soft capsule comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is an oral controlled release pharmaceutical composition comprising a soft capsule and a matrix, the matrix comprising about 75 mg, about 80 mg, about 85 mg, about 90 mg, about 95 mg, about 100 mg, about 105 mg, about 108 mg, about 110 mg, about 115 mg, about 120 mg, about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg of DMF and about 53% by weight of a mixture of mono- and di-glycerides; about 10% by weight of polyvinylpyrrolidone; about 3% by weight of polyoxyl 40 hydrogenated castor oil, and about 5% by weight of lactic acid. In one embodiment, the soft capsule is an enteric soft capsule comprising about 30% by weight of gelatin; about 10% by weight of methylacrylic acid copolymer; about 18% by weight of glycerol; about 1% by weight of triethyl citrate; about 1.5% by weight of ammonia; and about 37% by weight of water.

Another embodiment described herein is an oral controlled release pharmaceutical composition dosage forms comprising a daily total amount of FAE of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is an oral controlled release pharmaceutical composition dosage form comprising a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg.

Another embodiment described herein is an oral pharmaceutical compositions providing a daily total amount of FAE of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg FAE; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is an oral pharmaceutical compositions providing a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg DMF; about 53% by weight of a mixture of mono- and di-glycerides; about 10% by weight of polyvinylpyrrolidone; about 3% by weight of polyoxyl 40 hydrogenated castor oil, and about 5% by weight of lactic acid.

Another embodiment described herein is a method of treating multiple sclerosis in a subject in need thereof comprising orally administering to the subject one or more doses of a pharmaceutical composition providing a daily total amount of FAE of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg. In one embodiment, the pharmaceutical composition comprises about 28% by weight of FAE; about 53% by weight of a mixture of mono- and di-glycerides; about 10% by weight of polyvinylpyrrolidone; about 3% by weight of polyoxyl 40 hydrogenated castor oil; and about 5% by weight of lactic acid.

Another embodiment described herein is a method of treating multiple sclerosis in a subject in need thereof comprising orally administering to the subject one or more doses of a pharmaceutical composition providing a daily total amount of DMF of about 180 mg, about 200 mg, about 210 mg, about 216 mg, about 220 mg, about 230 mg, about 240 mg, about 360 mg, about 400 mg, about 420 mg, about 432 mg, about 440 mg, about 460 mg, or about 480 mg. In one embodiment, the pharmaceutical composition comprises about 28% by weight of DMF; about 53% by weight of a mixture of mono- and di-glycerides; about 10% by weight of polyvinylpyrrolidone; about 3% by weight of polyoxyl 40 hydrogenated castor oil; and about 5% by weight of lactic acid.

Another embodiment described herein is an oral pharmaceutical composition for treating multiple sclerosis in a subject in need thereof comprising one or more fumarate esters comprising DMF, MMF, or a combination thereof.

Another embodiment described herein is an oral pharmaceutical composition for treating multiple sclerosis in a subject in need thereof comprising one or more fumarate esters comprising DMF.

Another embodiment described herein is any of the foregoing compositions or methods, wherein the fumarate ester comprises a therapeutically effective amount of DMF, MMF, or a combination thereof.

Another embodiment described herein is any of the foregoing compositions or methods, wherein the fumarate ester comprises a therapeutically effective amount of DMF.

BRIEF DESCRIPTION OF THE DRAWINGS

Further advantageous features of the present disclosure will become more apparent with the following detailed description when taken with reference to the accompanying drawings, each according to an aspect of the present disclosure.

DETAILED DESCRIPTION

Figure 1:
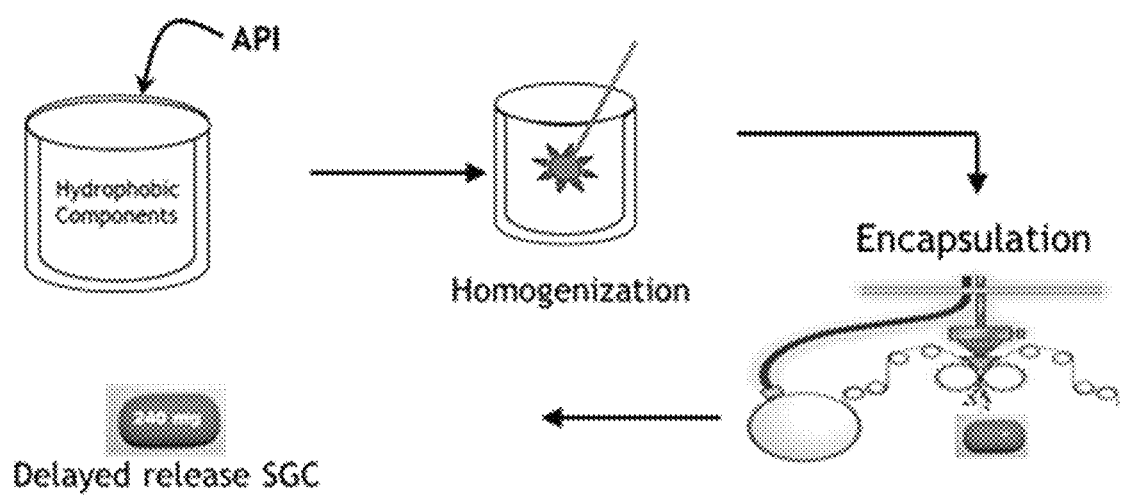
FIG. 1. Scheme for manufacturing enteric soft capsules comprising a DMF matrix.

Described herein are pharmaceutical compositions of fumarate esters such as dimethyl fumarate, monomethyl fumarate, other pharmacologically active fumarate esters, or combinations thereof.

The pharmaceutical compositions described herein provide matrix fills of fumarate esters, di-alkyl fumarates, mono-alkyl fumarates, such as dimethyl fumarate, monomethyl fumarate, or combinations thereof, and methods for preparation thereof. Also described herein are compositions and methods for manufacturing controlled, delayed, or extended release fumarate esters, dimethyl fumarate, monomethyl fumarate, or combinations thereof as soft capsule dosage forms. In one embodiment described herein, the fumarate ester pharmaceutical composition is encapsulated within an enteric soft capsule shell. In another embodiment, the fumarate ester is in the form of solid microparticles of defined size within a matrix comprising a lipid or lipophilic vehicle. In some aspects, described herein, the lipid or lipophilic vehicle may comprise an amount of one or more hydrophilic polymers, but as described herein, is considered a lipid or lipophilic vehicle.

As used herein, the terms "fumarate ester" or "FAE" refers to any pharmacologically active mono- or di-alkyl fumarate ester, such as monomethyl fumarate, dimethyl fumarate, or other fumarate esters, acids, salts, or derivatives thereof, and combinations or mixtures of any of the foregoing.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The terms "dosage" or "dose" as used herein denote any form of the active ingredient formulation that contains an amount sufficient to produce a therapeutic effect with a single administration. The dosage form used herein is for oral administration. The preferred oral dosage forms are soft capsules, or preferably, enteric soft capsules.

The terms "soft capsule" or "enteric soft capsule" as used herein refer to a soft capsule shell encapsulating a liquid or semisolid "matrix" or "fill" comprising vehicles, pharmaceutically acceptable excipients, and one or more active pharmaceutical ingredients.

The terms "active pharmaceutical ingredient load" or "drug load" as used herein refers to the quantity (mass) of the active pharmaceutical ingredient comprised in a single soft capsule fill.

The terms "formulation" or "composition" as used herein refers to the drug in combination with pharmaceutically acceptable excipients. This term includes orally administrable formulations as well as formulations administrable by other means.

The term "titration" as used herein refers to the incremental increase in drug dosage to a level that provides the optimal therapeutic effect.

The term "controlled release" as used herein encompasses the terms "immediate release," "modified release," "sustained release," "extended release," and "delayed release."

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of about 18 hours under physiological conditions or in an in vitro assay.

The term "modified release" as used herein refers to a composition that releases an active ingredient at a slower rate than does an immediate release formulation under physiological conditions or in an in vitro test.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

The term mean "particle size distribution" (PSD) as used herein refers to the mean particle size from a statistical distribution of a range of particle sizes as described herein. The distribution may be a Gaussian, normal distribution, or a non-normal distribution.

The terms "d90," "d50," and "d10" refer to the percentage (90%, 50%, or 10%, respectively) of particle sizes that are less than a specified size, range, or distribution. For example, d90≤90 µm as specified means that 90% of the particle sizes within a distribution of particles are less than or equal to 90 µm.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective (e.g., a therapeutic effect) to improve a condition, symptom, disorder, or parameter associated with a disorder, or a likelihood thereof.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to weight percent unless noted otherwise.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "having," and the like mean "comprising."

The term "or" can be conjunctive or disjunctive.

One embodiment described herein, is a controlled release pharmaceutical composition comprising an enteric soft capsule shell encapsulating a matrix fill comprising one or more fumarate esters.

In another embodiment, the enteric soft capsule provides controlled release properties.

In another embodiment, the matrix fill provides controlled release properties. Such controlled release matrix fills are described in International Patent Application Publication No. WO 2005/009409; U.S. Patent Application Publication No. US 2006/0115527; U.S. Pat. Nos. 8,293,270; and 8,333,989, each of which is incorporated by reference herein for such teachings. In one aspect, the matrix is configured to provide controlled release, extended release, sustained release, delayed release, or combinations thereof.

In another embodiment, the matrix comprises a lipid or lipophilic vehicle that provides a suspension of fumarate ester microparticles having defined sizes. In one aspect, an enteric soft capsule comprising a suspension of fumarate ester microparticles provides controlled release delivery of the fumarate ester.

The fumarate ester particles described herein (e.g., dimethyl fumarate or monomethyl fumarate) may be generated by any particle size reduction or particle growth methodology known to one having ordinary skill the art. Exemplary and non-limiting methods may comprise a "top-down" reduction in particle size including mechanical micronization techniques, wherein a larger particle is crushed, bashed, or ground into a smaller particle through techniques, such as jet milling, ball milling, or high pressure homogenization; or particle engineering techniques such as cryogenic spraying or crystal engineering. In addition, "bottom-up" processing may be used to build a suitable size of particles as described herein using dual solvent/anti-solvent rapid precipitation techniques. See, *Handbook of Pharmaceutical Granulation Technology*, CRC Press, 3rd Edition, 2010, which is incorporated by reference herein for teachings related to generating pharmaceutical particles. In one aspect described herein, fumarate ester particles of a specified size distribution are produce using a milling technique.

In another embodiment, the pharmaceutical composition comprises matrix fills for fumarate esters, such as dimethyl fumarate, monomethyl fumarate, or derivatives thereof, based on lipids or lipophilic vehicles. The described matrices have a hydrophobic (lipophilic) surface in contact with the hydrophilic soft enteric capsule shell to minimize any potential shell-fill interactions, such as when enteric soft capsules are filled with hydrophilic vehicles.

Described herein are methods for manufacturing matrix fills comprising fumarate esters, such as dimethyl fumarate, monomethyl fumarate, or derivatives thereof, in a controlled release enteric soft capsule in the form of a suspension, where part or all of the fumarate ester is suspended within the matrix. Also provided are compositions and formulations where the fumarate ester is incorporated into a one-phase or two-phase matrix.

Also described herein are methods for manufacturing matrix fills comprising fumarate esters or derivatives thereof, in a delayed release enteric soft capsule in the form of a suspension, where part or all of the fumarate ester is suspended within the matrix.

Described herein are methods for manufacturing matrix fills comprising fumarate esters or derivatives thereof, in an extended release enteric soft capsule in the form of a suspension, where part or all of the fumarate ester is suspended within the matrix.

Another embodiment described herein is a controlled, delayed, or extended release enteric soft capsule having a shell and a matrix fill, wherein the matrix fill includes fumarate esters such as dimethyl fumarate, monomethyl fumarate, or derivatives thereof, suspended as solid particles in a lipid or lipophilic vehicle. In another embodiment, the lipid or lipophilic vehicle comprises a vegetable oil, hydrogenated vegetable oil, fatty acid, wax, fatty acid ester, or a combination thereof.

Exemplary matrix lipid or lipophilic vehicles comprise mineral oil; light mineral oil; natural oils (e.g., vegetable, corn, canola, sunflower, soybean, olive, coconut, cocoa, peanut, almond, cottonseed, persic, sesame, squalane, castor, cod liver) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol monocaprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, or stearyl alcohol, inter alia, or combinations thereof.

In one embodiment, the matrix comprises a solvent or solubility enhancing agent. Exemplary solvents or solubility enhancing agents useful for the matrix fills described herein include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, or combinations thereof.

In one embodiment, the matrix comprises solid particles of fumarate ester suspended in a lipid or lipophilic vehicle of vegetable oil, hydrogenated vegetable oil, fatty acid, fatty acid ester, or a combination thereof. The matrix can also comprise solvents and suspension agents such as polyethylene glycols of molecular weight ranging from about 200 to about 8000 (MN, number average molecular weight), polyvinylpyrrolidone, or combinations thereof.

In another embodiment, the matrix fill comprises a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "*Physical Pharmacy: Physical Chemical Principles in the Pharmaceutical Sciences*," Fourth Edition, pp. 371-373, A. Martin, Ed., Lippincott Williams & Wilkins, Philadelphia (1993), which is incorporated by reference herein for such teachings.

In another embodiment, the matrix comprises emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof.

In another embodiment, the matrix comprises a neutralizing agent. Without being bound to any theory, the neutralizing agent stabilizes the fumarate ester in the matrix fill by preventing hydrolysis. In addition, without being bound by any theory, the neutralizing agent stabilizes the enteric soft capsule shell by forming salts with the methylacrylate moieties from the capsule shell. In one aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, esters or salts thereof, or combinations thereof. In one aspect, the neutralizing agent is lactic acid.

In another embodiment, the matrix includes a hydrophilic internal phase and a lipid or lipophilic external phase. The hydrophilic internal phase can comprise polypropylene glycol or polyethylene glycol of molecular weight ranging from about 200 to about 8000 (MN, number average molecular weight). In another embodiment, the internal phase comprises hydroalcoholic solutions of cellulose derivatives, polyacrylates, polyvinyl polymers, or combinations thereof. In one embodiment, the internal phase comprises polymers such as methylcellulose, hydroxypropylmethylcellulose, polymethylmethacrylate, or polyvinylpyrrolidone (PVP). In one embodiment, the internal phase of the matrix state is "fluid" or "structured." A "fluid" internal phase, as used herein, means a completely flowable liquid whose globules can aggregate to make a larger globule. A "structured" internal phase, as used herein, means a solid, semisolid, or a gel whose shape is relatively stable and does not usually aggregate to form a large globule. A structured internal phase can provide controlled drug release and stabilize the physical state of the matrix. Without being bound to any theory, the structured nature of the matrix impedes solvation or diffusion of the fumarate ester out of the matrix. In another embodiment, the external phase comprises a vegetable oil, hydrogenated vegetable oil, fatty acid, fatty acid ester, wax, or a combination thereof. In another embodiment, fumarate ester is dispersed in the internal phase as a suspension form.

In another embodiment, the matrix fill is an emulsion type, where the fumarate ester is distributed in one or both of the external (lipophilic) and internal (hydrophilic) phases. The external phase of the emulsion matrix fill comprises lipid or lipophilic vehicles similar to those described herein. The fumarate ester can be dispersed in the internal phase as a solution or as a suspension. For example, one portion of the fumarate ester in the form of a powder is incorporated in the internal phase, while another portion is dispersed in the external phase as solid particles. An emulsion-type matrix may comprise a surfactant or combination of surfactants having HLB values ranging from about 2 to about 40, including all integers within the specified range. In one aspect, the HLB range comprises from about 8 to about 20, including all integers within the specified range.

In one embodiment, the pharmaceutical composition described herein comprises an enteric soft capsule comprising a matrix comprising a lipid or lipophilic vehicle that provides a suspension of a fumarate ester. In one embodiment described herein, the fumarate ester is a mono- or di-alkyl fumarate of Formula I:

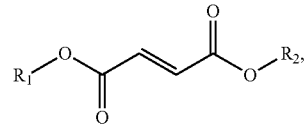

wherein $R_1$ and $R_2$, which may be the same or different, independently represent hydrogen or a linear, branched, or cyclic, saturated or unsaturated $C_{1-20}$ alkyl radical, which may be optionally substituted with halogen (Cl, F, I, Br), hydroxy, $C_{1-4}$ alkoxy, nitro, or cyano for preparing a pharmaceutical composition as described herein.

The $C_{1-20}$ alkyl radicals, $C_{1-8}$ alkyl radicals, and $C_{4-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. In one aspect, at least one of $R_1$ or $R_2$ is a $C_{1-5}$ alkyl, especially methyl or ethyl. In another aspect, $R_1$ and $R_2$ are the same or different $C_{1-5}$ alkyl radicals such as methyl, ethyl, n-propyl, or t-butyl. In one aspect, $R_1$ and $R_2$ are the same or different $C_{1-5}$ alkyl radicals such as methyl and ethyl. In one aspect, $R_1$ and $R_2$ are identical and are methyl or ethyl. In one aspect, the fumarate ester is monomethyl fumarate, dimethyl fumarate, methyl ethyl fumarate, or diethyl fumarate. In one aspect, the fumarate ester is monomethyl fumarate, dimethyl fumarate, or a combination thereof. In one aspect, the fumarate ester is monomethyl fumarate. In another aspect, the fumarate ester is dimethyl fumarate.

In one embodiment, the fumarate ester is:

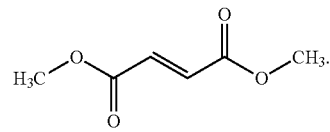

In one embodiment, the fumarate ester is:

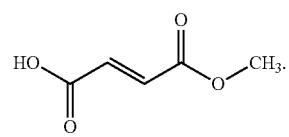

In one embodiment, the pharmaceutical compositions described herein comprise pharmaceutically acceptable salts of the active ingredient. The term "pharmaceutically acceptable salts" of an active ingredient includes alkali metal salts such as, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid, inter alia. In another embodiment, the active ingredient may also be in the form of pharmaceutically acceptable uncharged or charged molecules, molecular complexes, solvates, or anhydrates thereof, and, if relevant, single isomers, enantiomers, racemic mixtures, or mixtures thereof. In another embodiment, the active pharmaceutical ingredient may be in any of its crystalline, polymorphous, semi-crystalline, amorphous or polyamorphous forms, or mixtures thereof.

The fumarate esters described herein can be prepared by processes known in the art. See, e.g., EP 0 312 697 and U.S. Patent Application Publication Nos. US 2013/0295169; US 2014/0179779; and US 2014/0200363, each of which is incorporated by reference herein for such teachings.

In one embodiment, the pharmaceutical composition comprises an active ingredient or drug. In one embodiment, the active ingredient or drug is a pharmacologically active fumarate ester. In one embodiment described herein, the active ingredient is a dialkyl fumarate. In one embodiment described herein, the active ingredient is a fumarate ester or combination of fumarate esters. In one embodiment described herein, the active ingredient is dimethyl fumarate. In another embodiment described herein, the active ingredient is monomethyl fumarate. In another embodiment described herein, the active ingredient is a combination of dimethyl fumarate and monomethyl fumarate. In another embodiment described herein, the active ingredient is a combination of dimethyl fumarate, monomethyl fumarate, and other pharmacologically active fumarate esters, acids, salts, or derivatives thereof. In another embodiment, the active ingredient or drug comprises dimethyl fumarate, monomethyl fumarate, other pharmacologically active fumarate esters, acids, or salts, derivatives thereof, or combinations thereof. In another embodiment, the active ingredient comprises dimethyl fumarate, monomethyl fumarate, or derivatives thereof, combined with aspirin, ibuprofen, naproxene, diclofenac, ketoprofen, celecoxib, other nonsteroidal anti-inflamatory active drugs (NSAIDs), or combinations thereof. In one embodiment, the pharmaceutical composition comprises a fumarate ester combined with aspirin.

In another embodiment, the pharmaceutical composition comprises a fumarate ester combined with one or more leukotriene receptor antagonists. In another embodiment, the pharmaceutical composition comprises a fumarate ester combined with montelukast (Singulair®) or zafirlukast (Accolate®). In another embodiment, the pharmaceutical composition comprises a fumarate ester combined with montelukast or zafirlukast and an NSAID. In another embodiment, the pharmaceutical composition comprises a fumarate ester combined with montelukast or zafirlukast and aspirin.

In one embodiment, the fumarate ester-to-matrix ratio range comprises from about 1:50 to about 1:1 by weight, including all ratios within the specified range. In another embodiment, the fumarate ester-to-matrix ratio range comprises from about 1:10 to about 1:1 by weight, including all ratios within the specified range. In one aspect, the fumarate ester-to-matrix ratio comprises about 1:9 to about 1:1 by weight, including all ratios within the specified range. In another aspect, the fumarate ester-to-matrix ratio range comprises from about 1:5 to about 1:1 by weight, including all ratios within the specified range. In another aspect, the fumarate ester-to-matrix ratio is about 1:5; about 1:4; about 1:3; about 1:2; about 1:1; or about 0.5:1. In other aspects, the fumarate ester-to-matrix ratio is 1:3.5; 1:3.1; 1:2.9; 1:2.3; or 1:1.5.

In one embodiment, the active ingredient comprises about 1% to about 70% of the matrix, including all integers and fractions within the specified range. In another embodiment, the active ingredient comprises about 70%; about 60%; about 50%; about 40%; about 30%; about 20%; about 15%; about 10%; about 5%; about 2%; or about 1% of the matrix fill. In one aspect, the active ingredient comprises about 64% of the matrix. In another embodiment, the active ingredient comprises about 57% of the matrix. In another embodiment, the active ingredient comprises about 50% of the matrix. In another embodiment, the active ingredient comprises about 32% of the matrix. In another embodiment, the active ingredient comprises about 30% of the matrix. In another embodiment, the active ingredient comprises about 28% of the matrix. In another embodiment, the active ingredient comprises about 25% of the matrix.

In one embodiment, the solid fumarate ester particles are milled or micronized. In one embodiment, the fumarate ester comprises a particle size range of about 1 μm to about 500 μm, including all integers and fractions within the specified range. In one aspect, the micronized solid fumarate ester particles have a particle size of about 1 μm, 2 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, or even larger. In another aspect, the solid particles of fumarate ester comprise a distribution of particle sizes, comprising particles of any of the foregoing particle sizes.

In another embodiment, the solid fumarate ester particles have mean particle size distributions (PSD) ranging from about 20 μm, μm to about 300 μm, including all integers and fractions within the specified range. In one aspect, the solid particles of fumarate ester comprise mean particle size distributions of about 20 μm, about 30 μm, about 40 μm, about 50 μm, about 60 about 70 μm, about 80 μm, about 90 μm, about 100 μm, about 120 μm, about 140 μm, about 160 μm, about 180 μm, about 190 μm, about 200 μm, about 220 μm, about 240 μm, about 260 μm, about 280 μm, or about 300 μm. In one aspect, the solid particles of fumarate ester have a mean particle size distribution of about 260 μm. In one aspect, the solid particles of fumarate ester have a mean particle size distribution of about 170 µm. In one aspect, the solid particles of fumarate ester have a mean particle size distribution of about 140 µm. In one aspect, the solid particles of fumarate ester have a mean particle size distribution of about 90 µm. In one aspect, the solid particles of fumarate ester have a mean particle size distribution of about 80 µm. In one aspect, the solid particles of fumarate ester have a mean particle size distribution of about 25 µm.

In another embodiment, the solid fumarate ester particles have a particle size distribution with a d90 of less than or equal to about 500 µm. In one aspect, the particle size distribution of solid particles of fumarate ester have a d90 of ≤ to about 20 µm, about 30 µm, about 40 µm, about 50 µm, about 60 µm, about 70 µm, about 80 µm, about 90 µm, about 100 µm, about 120 µm, about 140 µm, about 160 µm, about 180 µm, about 190 µm, about 200 µm, about 220 µm, about 240 about 260 µm, about 280 µm, about 300 µm, or about 400 µm. In one aspect, the solid particles of fumarate ester have a particle size distribution with a d90 of ≤ about 260 µm (d90≤260 µm). In one aspect, the solid particles of fumarate ester have a particle size distribution with a d90 of ≤ about 170 µm, µm (d90≤170 µm). In one aspect, the solid particles of fumarate ester have a particle size distribution with a d90 of ≤ about 140 µm (d90≤140 µm). In one aspect, the solid particles of fumarate ester have a particle size distribution with a d90 of ≤ about 100 µm (d90≤100 µm). In one aspect, the solid particles of fumarate ester have a particle size distribution with a d90 of ≤ about 90 µm (d90≤90 µm). In one aspect, the solid particles of fumarate ester have a particle size distribution with a d90 of ≤ about 80 µm (d90≤80 µm). In one aspect, the solid particles of fumarate ester have a particle size distribution with a d90 of ≤ about 25 µm (d90≤25 µm).

In another embodiment, the solid fumarate ester particles have a mean particle size distribution comprising a range of particle sizes with a d10 of ≤10 µm and a d90 of ≤500 µm. In one aspect, the solid particles of fumarate ester have a particle size distribution with a d10 of ≤ to about 10 µm and a d90 of ≤ to about 400 µm, a d10 of ≤ to about 10 µm and a d90 of ≤ to about 300 µm, a d10 of ≤ to about 10 µm and a d90 of ≤ to about 250 µm, a d10 of ≤ to about 10 µm and a d90 of ≤ to about 200 µm, a d10 of ≤ to about 10 µm and a d90 of ≤ to about 150 µm, a d10 of ≤ to about 10 µm and a d90 of ≤ to about 100 µm. In one aspect, the solid particles of fumarate ester have a particle size distribution with a d10 of ≤ to about 10 µm and a d90 of ≤ to about 100 µm, a d10 of ≤ to about 20 µm and a d90 of ≤ to about 100 µm, a d10 of ≤ to about 30 µm and a d90 of ≤ to about 100 µm, a d10 of ≤ to about 40 µm and a d90 of ≤ to about 100 µm, a d10 of ≤ to about 50 µm and a d90 of ≤ to about 100 µm, a d10 of ≤ to about 60 µm and a d90 of ≤ to about 100 µm, a d10 of ≤ to about 70 µm and a d90 of ≤ to about 100 µm, a d10 of ≤ to about 80 µm and a d90 of ≤ to about 100 µm.

In another embodiment, the solid particles of fumarate ester comprise multiple distributions of particle sizes. In one aspect, the solid particles of fumarate ester may comprise a plurality of independently combined mean particle size distributions, wherein each independent mean particle size distribution ranges from about 20 µm to about 300 µm, including all integers and fractions within the specified range. In another aspect, the plurality of mean particle size distributions can comprise a mean particle size distribution of about 261 µm, a mean particle size distribution of about 168 µm, a mean particle size distribution of about 148 µm, a mean particle size distribution of about 90 µm, a mean particle size distribution of about 80 µm, or a mean particle size distribution of about 26 µm. In another aspect, the plurality of mean particle size distributions can comprise combinations of independent mean particle size distributions, wherein each independently combined mean particle size distribution is about 261 µm, about 168 µm, about 148 µm, about 90 µm, about 80 µm, or about 26 µm. In another aspect, the solid particles of fumarate ester comprise a combination of independently combined mean particle size distributions of about 30 µm to about 260 µm in a single matrix fill. Any of the foregoing particle size distributions may be combined to provide the desired controlled release profile.

The forgoing sizes of fumarate ester particles may be determined using standard techniques known to one of ordinary skill in the art. The exemplary techniques that can be used for measuring the size of fumarate ester particles may include laser diffraction analysis, light scattering (e.g., dynamic light scattering), microscopic particle image analysis, elutriation, or aerosol mass spectrometry. The sample of fumarate ester particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt following the recommended operating procedures according to the manufacturer's instructions.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter (D[4,3] or $d_{43}$), mean surface area diameter (D[3,2] or $d_{32}$) or the mean number particle diameter (D[1,0] or $d_{10}$). Because the particle size distribution values vary depending on the measurement methodology and how the distribution is expressed, the comparison of different mean particle size distributions must be calculated by the same methodology in order to have an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

Another embodiment described herein is a method for manufacturing a matrix fill for a controlled release soft enteric capsule comprising particles of fumarate esters such as dimethyl fumarate or monomethyl fumarate of defined sizes. In one aspect, the particles are of a similar size distribution. In another aspect, the fumarate ester particles comprise varied size distributions. In another aspect, the fumarate ester particles comprise several size distributions. In another aspect, the fumarate ester particles comprise a mixture of smaller and larger size distributions. Without being bound to any theory, smaller particles are generally solubilized and released more rapidly than larger particles. The release rate can be adjusted to achieve a specific therapeutic window over a defined period and produce controlled release, delayed release, or extended release compositions by combining multiple fumarate ester particle sizes or distributions.

Another embodiment described herein is a method for manufacturing a pharmaceutical composition comprising fumarate ester(s) where the fumarate ester does not sublime during processing, manufacturing, after production, or during storage. Soft enteric capsules comprising fumarate ester in the matrix fills described herein are stable for months or years. Without being bound to any theory, it is believed that suspending solid fumarate ester in a lipid or lipophilic vehicle comprising an organic acid prevents or retards sublimation and stabilizes the fumarate ester. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, or even longer. In another aspect, the pharmaceutical compositions described herein are stable for 1 year or longer at 25° C. and 60% RH. In another aspect, the pharmaceutical compositions described herein are stable for 2 years or longer at 25° C. and 60% RH.

Another embodiment described herein is a method for preparing a pharmaceutical matrix comprising a fumarate ester. An exemplary scheme of a manufacturing process is shown in FIG. 1. The method comprises applying heat to the matrix components during mixing or prior to mixing at about the melting point of the matrix fill composition; and then mixing the fumarate ester with the lipid or lipophilic matrix ingredients using mechanical or ultrasonic forces to form the matrix fill. The matrix fill is flowable such that it can be encapsulated using a rotary die encapsulation machine. In one embodiment, the matrix components are heated to a temperature in the range of from about 25° C. to about 70° C. In another embodiment, the matrix components are heated to a temperature in the range of from about 25° C. to about 30° C.

In one embodiment, the matrix comprises a lipid or lipophilic vehicle, a neutralizing agent, excipients, and sold particles of fumarate ester. In another aspect, the matrix comprises polyethylene glycols, polyvinylpyrrolidones, oils, and surfactants. In one aspect, the surfactant comprises polysorbate 80 or polyoxyl 40 hydrogenated castor oil. In another aspect, the matrix comprises dimethyl fumarate, a mixture of mono- and di-glycerides, polyvinylpyrrolidone, polyoxyl 40 hydrogenated castor oil, and lactic acid.

In one embodiment, the matrix comprising fumarate ester comprises the composition shown in Table 1 including all possible iterations of the specified ranges that provide 100% for the total weight percentage of the composition.

TABLE 1

Exemplary Matrix Fill Composition

| Ingredient | mg/capsule | % weight |
| --- | --- | --- |
| Fumarate Ester (Mean PSD 80 μm) | 240 | 32 |
| Capmul ® MCM | 375 | 50 |
| Povidone K 30 | 15-52.5 | 0.01-7 |
| Cremophor ® RH 40 | 15-75 | 2-10 |
| Lactic acid | 7.5-37.5 | 1-5 |
| TOTAL | 750 mg | 100% |

In one embodiment, the matrix comprises about 32% by weight of fumarate ester (PSD: 80 μm); about 50% by weight of a mixture of mono- and di-glycerides; at least about 0.01-7% by weight of polyvinylpyrrolidone; at least about 2-10% by weight of polyoxyl 40 hydrogenated castor oil, and at least about 1-5% by weight of lactic acid, including all iterations of the specified ranges. In one aspect, the composition prevents sublimation of the FAE during processing and manufacturing. In one aspect, the composition reduces the onset of symptoms of gastrointestinal side effects. In another aspect, the composition is stable for at least 6 months at 25° C. and 60% relative humidity. In one aspect, the composition is stable for at least 24 months.

In one embodiment, the matrix comprises the composition shown in Table 2 including all possible iterations of the specified ranges that provide 100% for the total weight percentage.

TABLE 2

Exemplary Matrix Fill Composition

| Ingredient | mg/capsule | % weight |
| --- | --- | --- |
| Fumarate ester PSD: d90 ≤ 100 μm | 480 | 48-60 |
| Capmul ® MCM | 216-470 | 25-48.0 |
| Cremophor ® RH 40 | 7.3-120 | 0.85-12.0 |
| Povidone K 30 | 7.3-50 | 0.85-5.0 |
| Lactic acid | 21.7-50 | 2.55-5.0 |
| TOTAL | 750 mg-1000 mg | 100% |

In another embodiment the matrix fill comprises about 32% of fumarate ester (PSD: ≤90 μm); about 25% to about 47% of a mixture of mono- and di-glycerides; at least about 0.01-7% polyvinylpyrrolidone; at least about 0.85-12% polyoxyl 40 hydrogenated castor oil, and at least about 1-5% lactic acid, including all iterations of the specified ranges. In one aspect, the composition prevents sublimation of the FAE during processing and manufacturing. In another aspect, the composition reduces the onset of symptoms of any gastrointestinal side effects. In another aspect, the composition is stable for at least 6 months at 25° C. and 60% relative humidity. In another aspect, the composition is stable for at least 24 months at 25° C. and 60% relative humidity.

In one embodiment, the fumarate ester pharmaceutical composition comprises a soft gelatin capsule shell comprising a matrix comprising a fumarate ester.

In one embodiment, the fumarate ester pharmaceutical composition comprises an enteric soft capsule shell comprising a matrix comprising a fumarate ester. Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-forming polymers that are useful for creating enteric soft capsules are gelatin or hydroxypropylmethylcellulose (HPMC). In one aspect of the enteric soft capsule shell described herein, the film-forming polymer is gelatin.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In another aspect, the methacrylic acid copolymer comprises EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; other poly(meth)acrylate polymers; or a mixture thereof. In one aspect, the enteric polymer is EUDRAGIT® L 100, a methacrylic acid copolymer, Type A. Acid-insoluble polymer specifications are detailed in the United States Pharmacopoeia and in various monographs.

In another embodiment described herein, the enteric polymer in the enteric soft capsule shell comprises poly(methacylic acid-co-ethyl acrylate) 1:1 (e.g., EUDRAGIT® L 100-55). In one embodiment described herein, the enteric polymer comprises poly(ethyl acrylate-co-methyl methacrylate) 2:1 (e.g., EUDRAGIT® NE 40 D). In another embodiment described herein, the enteric polymer comprises poly(methyl acrylate-co-methyl methacrylate-co-methacrylic acid) 7:3:1 (e.g., EUDRAGIT® FS 30 D). In another embodiment described herein, the enteric polymer comprises a combination of poly(methacylic acid-co-ethyl acrylate) 1:1 and poly(methyl acrylate-co-methyl methacrylate-co-methacrylic acid) 7:3:1. In another embodiment, the enteric polymer comprises a combination of poly(methacylic acid-co-ethyl acrylate) 1:1 and poly(ethyl acrylate-co-methyl methacrylate) 2:1. In another embodiment, the enteric polymer comprises a combination of poly(methacylic acid-co-ethyl acrylate) 1:1, poly(ethyl acrylate-co-methyl methacrylate) 2:1, and poly(methyl acrylate-co-methyl methacrylate-co-methacrylic acid) 7:3:1.

In another embodiment, plasticizers that are useful for creating enteric soft capsules as described herein are glycerol, sorbitol, Sorbitol Special®, maltitol, corn syrup, propylene glycol, poly-alcohols with 3 to 6 carbon atoms, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions are made by dissolving the enteric acid-insoluble polymer in an aqueous solution of an alkali-neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali-neutralizing agent, ammonia is preferred. The film-forming polymer can then be combined with the plasticizer and solvent and then blended with the acid-insoluble gel to make a final homogeneous mix in a heat-controlled vessel with degassing by vacuum. The fugitive ammonia evaporates during degassing. Using the foregoing process, the alkali concentrations do not require heating or neutralizing with acid in order to neutralize the gel mass.

In another embodiment described herein, the enteric soft capsule shell is made using an aqueous dispersion of the acid-insoluble polymer by adding an alkali-neutralizing agent such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the bases or alkalis as described herein are dissolved directly in water and mixed with the plasticizer-wetted, film-forming polymer.

In one embodiment described herein, enteric acid-insoluble polymers in the form of salts of the bases or alkalis described herein are dissolved directly in water and mixed with the plasticizer-wetted, film-forming polymer. In another embodiment described herein, an aqueous dispersion of the acid-insoluble polymer or polymers is used, which obviates the need for the addition of the alkali-neutralizing agent described herein.

In one embodiment, the enteric soft capsule shell has the composition of Table 3, including all possible iterations of the specified ranges that provide 100% for the total weight percentage, including or excluding the optional, excipients, opacifiers, colorants, and flavorings.

TABLE 3

Enteric Soft Capsule Shell Composition

| Component | Exemplary Component | Composition Range (%) |
|---|---|---|
| Film-forming polymer | Gelatin | 20-36 |
| Enteric, acid-insoluble polymer | Methacrylic Acid Copolymer | 8-20 |
| Plasticizer | Glycerol, sorbitol, Triethyl citrate | 15-22 |
| Alkali-neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, the enteric soft capsule shell comprises a composition of about 30% film forming polymer; about 10% enteric, acid-insoluble polymer; about 20% plasticizer; about 1% alkali-neutralizing agent; and about 37% solvent.

In another embodiment, the weight percentage range of total polymer content (i.e., film forming polymer and enteric acid-insoluble polymer) of the enteric soft capsule described herein is about 30% to about 45%, including all integers and fractions within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all integers and fractions within the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali-neutralizing agent is ammonia (ammonium hydroxide; 30% w/v) that is added to comprise a weight percentage of about 1% to about 5% of the total enteric soft capsule composition. In one aspect, 30% w/v ammonia is added to comprise a weight percentage of about 2%. In another aspect, 30% w/v ammonia is added to comprise a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali-neutralizing agent. In another aspect, practically all of the ammonia is evaporated except for ammonium ions comprising salts with other moieties in the composition.

In one embodiment, the weight ratio range of film forming polymer to enteric acid-insoluble polymer (i.e., film forming:enteric) is about 25:75 ($\approx$0.33) to about 40:60 ($\approx$0.67) (i.e., $\approx$0.33-0.67), including all ratios within the specified range. In one aspect, the ratio of film forming polymer to enteric acid-insoluble polymer is about 30:70 ($\approx$0.43). In another aspect, the ratio of film forming polymer to enteric acid-insoluble polymer is about 28:72 ($\approx$0.38).

In one embodiment, the weight ratio of total plasticizer to film forming polymer is about 20:40 to 21:30 (i.e., $\approx$0.5-0.7), including all ratios within the specified range. In one aspect, the weight ratio of total plasticizer to film forming polymer is about 20:40 ($\approx$0.5). In another aspect, the weight ratio of total plasticizer to film forming polymer is about 21:30 ($\approx$0.7). In another aspect, the weight ratio of total plasticizer to film forming polymer is about 19:29 ($\approx$0.65). In another aspect, the weight ratio of total plasticizer to film forming polymer is about 19.3:29.2 ($\approx$0.66).

In one embodiment, the weight ratio of total plasticizer to enteric acid-insoluble polymer is about 1:1 to about 2:1 ($\approx$1-2), including all ratios within the specified range. In one aspect, the weight ratio of total plasticizer to enteric acid-insoluble polymer is about 11:10 ($\approx$1.1). In another aspect, the weight ratio of total plasticizer to enteric acid-insoluble polymer is about 14:10 ($\approx$1.4). In another aspect, the weight ratio of total plasticizer to enteric acid-insoluble polymer is about 17:10 ($\approx$1.7). In another aspect, the weight ratio of total plasticizer to enteric acid-insoluble polymer is about 20:10 ($\approx$2). In another aspect, the weight ratio of total plasticizer to enteric acid-insoluble polymer is about 19.3:11.2 ($\approx$1.73).

In one embodiment, the weight ratio range of total plasticizer to total polymer (film forming and enteric acid-insoluble polymer) is about 18:45 to about 20:40 (i.e., $\approx$0.40-0.5), including all ratios within the specified range. In one aspect, the weight ratio range of total plasticizer to total polymer is about 18:45 ($\approx$0.40). In another aspect, the weight ratio range of total plasticizer to total polymer is about 19:40 ($\approx$0.475). In another aspect, the weight ratio range of total plasticizer to total polymer is about 20:40 ($\approx$0.5). In another aspect, the weight ratio range of total plasticizer to total polymer is about 19.3:40.4 ($\approx$0.477).

In one embodiment, the solvent comprises about 20% to about 40% of the enteric soft capsule composition, including all integers and fractions within the specified range. In one embodiment, the solvent is water. The quantity of water in the composition varies depending on the quantities of the other ingredients. For example, the quantity of opacifier, colorant, flavoring, or other excipients can change the percentage of water present in the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers and fractions within the specified range. In another embodiment, the moisture content is about 8% to about 12%, including all integers and fractions within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 4.

TABLE 4

Exemplary Enteric Soft Capsule Shell Composition

| Component | Percent weight (%) |
| --- | --- |
| Gelatin | 29.2 |
| Methacrylic Acid Copolymer (EUDRAGIT ® L 100) | 11.2 |
| Glycerol or Sorbitol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | 8.5-9.0 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

In another embodiment, the enteric soft capsule is described in U.S. Provisional Patent Application No. 62/015,063, which is incorporated by reference herein for such teachings.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

Films of the enteric soft capsule shell do not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. Enteric soft capsules made using the compositions described herein remain intact in hydrochloric acid or simulated gastric fluid for at least two hours. The capsules readily release the contents upon shifting the pH of the solution to ca. 6.8, such as that of simulated intestinal fluid.

In another embodiment, the final enteric capsule composition provides films of increased strength without substantially compromising film elasticity. Moreover, films made from the enteric soft capsule compositions as described herein are sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches ($\approx$0.254 mm) to about 0.050 inches ($\approx$1.27 mm), including all integers and fractions within the specified range. The shell thickness comprises about 0.010 inch ($\approx$0.254 mm), about 0.015 inch ($\approx$0.381 mm), about 0.02 in ($\approx$0.508 mm), about 0.03 in ($\approx$0.762 mm), about 0.04 in ($\approx$1.02 mm), or about 0.05 in ($\approx$1.27 mm). In one embodiment, the thickness is about 0.02 inches ($\approx$0.508 mm) to about 0.040 inches ($\approx$1.02 mm). In one embodiment, the shell thickness is about 0.028 inches ($\approx$0.711 mm). In another embodiment, the shell thickness is about 0.033 inches ($\approx$0.838 mm). In another embodiment, the shell thickness is about 0.038 inches ($\approx$0.965 mm).

In one embodiment described herein, the enteric soft capsule shell described herein, encapsulates a matrix fill as described herein. In another embodiment described herein, the enteric soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20 oval, or 30 oval). In another embodiment described herein, the enteric soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those of ordinary skill in the art. See *Remington's Essentials of Pharmaceutics*, Pharmaceutical Press Publishing Company, London, UK, 1st Edition, 2013, which is incorporated by reference herein for such teachings.

The enteric soft capsules described herein can contain a matrix fill that is liquid, semi-solid, or solid. Capsules prepared as described herein can contain a hydrophobic solution or suspension, such as vegetable oils or shortening, or waxes, or combinations thereof. The matrix fill can be formulated to prevent interaction with the capsule shell components and release the pharmaceutical composition at a specified rate.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

In one embodiment, the pharmaceutical composition described herein provides a dosage of fumarate ester for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from about 0 to about 9 years of age. In another aspect, the human subject is from about 10 years to about 17 years of age. In another aspect, the human subject is over 17 years of age. In another aspect, the human subject is an adult ($\geq$18 years of age).

The dosage form can be administered, for example, 1x, 2x, 3x, 4x, 5x, 6x, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, general autoimmune or neurodegenerative disorders.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In another embodiment, the pharmaceutical composition described herein may be used to treat, prevent, retard the progression of, delay the onset, ameliorate, reduce the symptoms of, or prophylaxis of general autoimmune or neurodegenerative disorders. Neurodegenerative disorders, as used herein, include multiple sclerosis (MS), which includes relapsing remitting multiple sclerosis (RRMS), secondary progressive multiple sclerosis (SPMS), primary progressive multiple sclerosis (PPMS), progressive relapsing multiple sclerosis (PPvMS), amyotrophic lateral sclerosis (ALS), psoriasis, psoriatic arthritis, Alzheimer's disease, Parkinson's disease, or any combination thereof.

In one embodiment described herein, other conditions, disorders, or diseases are controlled by administration of fumarate esters. The administration of pharmaceutical compositions comprising fumarate esters, as described herein, may be used for treating, preventing, retarding the progression of, delaying the onset, ameliorating, reducing the symptoms of, or prophylaxis of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behcet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome.

One embodiment described herein comprises a method for orally administering a dosage form that provides a total amount of fumarate ester of about 20 mg to about 1000 mg (e.g., ~20-1000 mg), including all integers and fractions within the specified range.

In one embodiment described herein, the fumarate ester (FAE) dosage form can comprise, but is not limited to about 50 mg FAE, about 55 mg FAE, about 60 mg FAE, about 65 mg FAE, about 70 mg FAE, about 75 mg FAE, about 80 mg FAE, about 85 mg FAE, about 90 mg FAE, about 95 mg FAE, about 100 mg FAE, about 105 mg FAE, about 110 mg FAE, about 115 mg FAE, about 120 mg FAE, about 125 mg FAE, about 130 mg FAE, about 135 mg FAE, about 140 mg FAE, about 145 mg FAE, about 150 mg FAE, about 155 mg FAE, about 160 mg FAE, about 165 mg FAE, about 170 mg FAE, about 175 mg FAE, about 180 mg FAE, about 185 mg FAE, about 190 mg FAE, about 195 mg FAE, about 200 mg FAE, about 205 mg FAE, about 210 mg FAE, about 215 mg FAE, about 220 mg FAE, about 225 mg FAE, about 230 mg FAE, about 235 mg FAE, about 240 mg FAE, about 245 mg FAE, about 250 mg FAE, about 255 mg FAE, about 260 mg FAE, about 265 mg FAE, about 270 mg FAE, about 275 mg FAE, about 280 mg FAE, about 285 mg FAE, about 290 mg FAE, about 295 mg FAE, about 300 mg FAE, about 305 mg FAE, about 310 mg FAE, about 315 mg FAE, about 320 mg FAE, about 325 mg FAE, about 330 mg FAE, about 335 mg FAE, about 340 mg FAE, about 345 mg FAE, about 350 mg FAE, about 355 mg FAE, about 360 mg FAE, about 365 mg FAE, about 370 mg FAE, about 375 mg FAE, about 380 mg FAE, about 385 mg FAE, about 390 mg FAE, about 395 mg FAE, about 400 mg FAE, about 405 mg FAE, about 410 mg FAE, about 415 mg FAE, about 420 mg FAE, about 425 mg FAE, about 430 mg FAE, about 435 mg FAE, about 440 mg FAE, about 445 mg FAE, about 450 mg FAE, about 455 mg FAE, about 460 mg FAE, about 465 mg FAE, about 470 mg FAE, about 475 mg FAE, or about 480 mg FAE. In one embodiment, the foregoing dosages comprise a partial dose, e.g., including but not limited to one dose of a twice or thrice daily regimen. In another embodiment, any of the foregoing dosages comprise a total daily dose.

In another embodiment described herein, the fumarate ester (FAE) dosage form can comprise, but is not limited to about 50 mg FAE, about 52 mg FAE, about 54 mg FAE, about 56 mg FAE, about 58 mg FAE, about 60 mg FAE, about 62 mg FAE, about 64 mg FAE, about 66 mg FAE, about 68 mg FAE, about 70 mg FAE, about 72 mg FAE, about 74 mg FAE, about 76 mg FAE, about 78 mg FAE, about 80 mg FAE, about 82 mg FAE, about 84 mg FAE, about 86 mg FAE, about 88 mg FAE, about 90 mg FAE, about 92 mg FAE, about 94 mg FAE, about 96 mg FAE, about 98 mg FAE, about 100 mg FAE, about 102 mg FAE, about 104 mg FAE, about 106 mg FAE, about 108 mg FAE, about 110 mg FAE, about 112 mg FAE, about 114 mg FAE, about 116 mg FAE, about 118 mg FAE, about 120 mg FAE, about 122 mg FAE, about 124 mg FAE, about 126 mg FAE, about 128 mg FAE, about 130 mg FAE, about 132 mg FAE, about 134 mg FAE, about 136 mg FAE, about 138 mg FAE, about 140 mg FAE, about 142 mg FAE, about 144 mg FAE, about 146 mg FAE, about 148 mg FAE, about 150 mg FAE, about 152 mg FAE, about 154 mg FAE, about 156 mg FAE, about 158 mg FAE, about 160 mg FAE, about 162 mg FAE, about 164 mg FAE, about 166 mg FAE, about 168 mg FAE, about 170 mg FAE, about 172 mg FAE, about 174 mg FAE, about 176 mg FAE, about 178 mg FAE, about 180 mg FAE, about 182 mg FAE, about 184 mg FAE, about 186 mg FAE, about 188 mg FAE, about 190 mg FAE, about 192 mg FAE, about 194 mg FAE, about 196 mg FAE, about 198 mg FAE, about 200 mg FAE, about 202 mg FAE, about 204 mg FAE, about 206 mg FAE, about 208 mg FAE, about 210 mg FAE, about 212 mg FAE, about 214 mg FAE, about 216 mg FAE, about 218 mg FAE, about 220 mg FAE, about 222 mg FAE, about 224 mg FAE, about 226 mg FAE, about 228 mg FAE, about 230 mg FAE, about 232 mg FAE, about 234 mg FAE, about 236 mg FAE, about 238 mg FAE, about 240 mg FAE, about 242 mg FAE, about 244 mg FAE, about 246 mg FAE, about 248 mg FAE, about 250 mg FAE, about 252 mg FAE, about 254 mg FAE, about 256 mg FAE, about 258 mg FAE, about 260 mg FAE, about 262 mg FAE, about 264 mg FAE, about 266 mg FAE, about 268 mg FAE, about 270 mg FAE, about 272 mg FAE, about 274 mg FAE, about 276 mg FAE, about 278 mg FAE, about 280 mg FAE, about 282 mg FAE, about 284 mg FAE, about 286 mg FAE, about 288 mg FAE, about 290 mg FAE, about 292 mg FAE, about 294 mg FAE, about 296 mg FAE, about 298 mg FAE, about 300 mg FAE, about 302 mg FAE, about 304 mg FAE, about 306 mg FAE, about 308 mg FAE, about 310 mg FAE, about 312 mg FAE, about 314 mg FAE, about 316 mg FAE, about 318 mg FAE, about 320 mg FAE, about 322 mg FAE, about 324 mg FAE, about 326 mg FAE, about 328 mg FAE, about 330 mg FAE, about 332 mg FAE, about 334 mg FAE, about 336 mg FAE, about 338 mg FAE, about 340 mg FAE, about 342 mg FAE, about 344 mg FAE, about 346 mg FAE, about 348 mg FAE, about 350 mg FAE, about 352 mg FAE, about 354 mg FAE, about 356 mg FAE, about 358 mg FAE, about 360 mg FAE, about 362 mg FAE, about 364 mg FAE, about 366 mg FAE, about 368 mg FAE, about 370 mg FAE, about 372 mg FAE, about 374 mg FAE, about 376 mg FAE, about 378 mg FAE, about 380 mg FAE, about 382 mg FAE, about 384 mg FAE, about 386 mg FAE, about 388 mg FAE, about 390 mg FAE, about 392 mg FAE, about 394 mg FAE, about 396 mg FAE, about 398 mg FAE, about 400 mg FAE, about 402 mg FAE, about 404 mg FAE, about 406 mg FAE, about 408 mg FAE, about 410 mg FAE, about 412 mg FAE, about 414 mg FAE, about 416 mg FAE, about 418 mg FAE, about 420 mg FAE, about 422 mg FAE, about 424 mg FAE, about 426 mg FAE, about 428 mg FAE, about 430 mg FAE, about 432 mg FAE, about 434 mg FAE, about 436 mg FAE, about 438 mg FAE, about 440 mg FAE, about 442 mg FAE, about 444 mg FAE, about 446 mg FAE, about 448 mg FAE, about 450 mg FAE, about 452 mg FAE, about 454 mg FAE, about 456 mg FAE, about 458 mg FAE, about 460 mg FAE, about 462 mg FAE, about 464 mg FAE, about 466 mg FAE, about 468 mg FAE, about 470 mg FAE, about 472 mg FAE, about 474 mg FAE, about 476 mg FAE, about 478 mg FAE, or about 480 mg FAE. In one embodiment, the foregoing dosages comprise a partial dose, e.g., including but not limited to one dose of a twice or thrice daily regimen. In another embodiment, any of the foregoing dosages comprise a total daily dose.

In one embodiment, the daily dosage is about 80 mg FAE to about 480 mg FAE including all integers and fractions within the specified range. In another embodiment, the daily dosage is about 90 mg FAE to about 120 mg FAE, including all integers and fractions within the specified range. In another embodiment, the daily dosage is about 90 mg FAE to about 240 mg FAE, including all integers and fractions within the specified range. In another embodiment, the daily dosage is about 100 mg FAE to about 200 mg FAE, including all integers and fractions within the specified range. In another embodiment, the daily dosage is about 100 mg FAE to about 240 mg FAE, including all integers and fractions within the specified range. In another embodiment, the daily dosage is about 180 mg FAE to about 240 mg FAE, including all integers and fractions within the specified range. In one embodiment, the daily dosage is about 200 mg FAE to about 240 mg FAE, including all integers and fractions within the specified range. In another embodiment, the daily dosage is about 360 mg FAE to about 480 mg FAE, including all integers and fractions within the specified range. In another embodiment, the daily dosage is about 400 mg FAE to about 480 mg FAE, including all integers and fractions within the specified range. In another embodiment, the daily dosage is about 480 mg FAE.

In another embodiment, the daily dosage form can comprise, but is not limited to, a total amount of FAE of about 80 mg FAE, about 82 mg FAE, about 84 mg FAE, about 86 mg FAE, about 88 mg FAE, about 90 mg FAE, about 92 mg FAE, about 94 mg FAE, about 96 mg FAE, about 98 mg FAE, about 100 mg FAE, about 102 mg FAE, about 104 mg FAE, about 106 mg FAE, about 108 mg FAE, about 110 mg FAE, about 112 mg FAE, about 114 mg FAE, about 116 mg FAE, about 118 mg FAE, about 120 mg FAE, about 122 mg FAE, about 124 mg FAE, about 126 mg FAE, about 128 mg FAE, about 130 mg FAE, about 132 mg FAE, about 134 mg FAE, about 136 mg FAE, about 138 mg FAE, about 140 mg FAE, about 142 mg FAE, about 144 mg FAE, about 146 mg FAE, about 148 mg FAE, about 150 mg FAE, about 152 mg FAE, about 154 mg FAE, about 156 mg FAE, about 158 mg FAE, about 160 mg FAE, about 162 mg FAE, about 164 mg FAE, about 166 mg FAE, about 168 mg FAE, about 170 mg FAE, about 172 mg FAE, about 174 mg FAE, about 176 mg FAE, about 178 mg FAE, about 180 mg FAE, about 182 mg FAE, about 184 mg FAE, about 186 mg FAE, about 188 mg FAE, about 190 mg FAE, about 192 mg FAE, about 194 mg FAE, about 196 mg FAE, about 198 mg FAE, about 200 mg FAE, about 202 mg FAE, about 204 mg FAE, about 206 mg FAE, about 208 mg FAE, about 210 mg FAE, about 212 mg FAE, about 214 mg FAE, about 216 mg FAE, about 218 mg FAE, about 220 mg FAE, about 222 mg FAE, about 224 mg FAE, about 226 mg FAE, about 228 mg FAE, about 230 mg FAE, about 232 mg FAE, about 234 mg FAE, about 236 mg FAE, about 238 mg FAE, about 240 mg FAE, about 242 mg FAE, about 244 mg FAE, about 246 mg FAE, about 248 mg FAE, about 250 mg FAE, about 252 mg FAE, about 254 mg FAE, about 256 mg FAE, about 258 mg FAE, about 260 mg FAE, about 262 mg FAE, about 264 mg FAE, about 266 mg FAE, about 268 mg FAE, about 270 mg FAE, about 272 mg FAE, about 274 mg FAE, about 276 mg FAE, about 278 mg FAE, about 280 mg FAE, about 282 mg FAE, about 284 mg FAE, about 286 mg FAE, about 288 mg FAE, about 290 mg FAE, about 292 mg FAE, about 294 mg FAE, about 296 mg FAE, about 298 mg FAE, about 300 mg FAE, about 302 mg FAE, about 304 mg FAE, about 306 mg FAE, about 308 mg FAE, about 310 mg FAE, about 312 mg FAE, about 314 mg FAE, about 316 mg FAE, about 318 mg FAE, about 320 mg FAE, about 322 mg FAE, about 324 mg FAE, about 326 mg FAE, about 328 mg FAE, about 330 mg FAE, about 332 mg FAE, about 334 mg FAE, about 336 mg FAE, about 338 mg FAE, about 340 mg FAE, about 342 mg FAE, about 344 mg FAE, about 346 mg FAE, about 348 mg FAE, about 350 mg FAE, about 352 mg FAE, about 354 mg FAE, about 356 mg FAE, about 358 mg FAE, about 360 mg FAE, about 362 mg FAE, about 364 mg FAE, about 366 mg FAE, about 368 mg FAE, about 370 mg FAE, about 372 mg FAE, about 374 mg FAE, about 376 mg FAE, about 378 mg FAE, about 380 mg FAE, about 382 mg FAE, about 384 mg FAE, about 386 mg FAE, about 388 mg FAE, about 390 mg FAE, about 392 mg FAE, about 394 mg FAE, about 396 mg FAE, about 398 mg FAE, about 400 mg FAE, about 402 mg FAE, about 404 mg FAE, about 406 mg FAE, about 408 mg FAE, about 410 mg FAE, about 412 mg FAE, about 414 mg FAE, about 416 mg FAE, about 418 mg FAE, about 420 mg FAE, about 422 mg FAE, about 424 mg FAE, about 426 mg FAE, about 428 mg FAE, about 430 mg FAE, about 432 mg FAE, about 434 mg FAE, about 436 mg FAE, about 438 mg FAE, about 440 mg FAE, about 442 mg FAE, about 444 mg FAE, about 446 mg FAE, about 448 mg FAE, about 450 mg FAE, about 452 mg FAE, about 454 mg FAE, about 456 mg FAE, about 458 mg FAE, about 460 mg FAE, about 462 mg FAE, about 464 mg FAE, about 466 mg FAE, about 468 mg FAE, about 470 mg FAE, about 472 mg FAE, about 474 mg FAE, about 476 mg FAE, about 478 mg FAE, or about 480 mg FAE. The daily dosage form can contain a total amount of fumarate ester effective for treatment of retarding the progression of, prophylaxis of delaying the onset of, amelioration of, or reducing symptoms of multiple sclerosis or psoriasis or other neurodegenerative disorders.

In one embodiment, the amount of fumarate ester can comprise about 80 mg to about 500 mg (e.g., 80-500 mg) of fumarate ester, including all integers and fractions within the specified range. In one embodiment, the amount can comprise, but is not limited to, about 80 mg to about 480 mg FAE, including all integers and fractions within the specified range. In one embodiment, the amount of fumarate ester can comprise about 80 mg FAE to about 85 mg FAE, about 85 mg FAE to about 90 mg FAE, about 85 mg FAE to about 100 mg FAE, about 90 mg FAE to about 95 mg FAE, about 90 mg FAE to about 100 mg FAE, about 90 mg FAE, to about 105 mg FAE, about 95 mg FAE to about 100 mg FAE, about 100 mg FAE to about 105 mg FAE, about 100 mg FAE to about 110 mg FAE, about 100 mg FAE to about 115 mg FAE, about 100 mg FAE to about 120 mg FAE, about 100 mg FAE to about 200 mg FAE, about 100 mg FAE to about 210 mg FAE, about 100 mg FAE to about 220 mg FAE, about 100 mg FAE to about 230 mg FAE, about 100 mg FAE to about 240 mg FAE, about 100 mg FAE to about 400 mg FAE, about 100 mg FAE to about 420 mg FAE, about 100 mg FAE to about 430 mg FAE, about 100 mg FAE to about 440 mg FAE, about 100 mg FAE to about 460 mg FAE, about 100 mg FAE to about 480 mg FAE, about 105 mg FAE to about 110 mg FAE, about 105 mg FAE to about 115 mg FAE, about 105 mg FAE to about 120 mg FAE, about 105 mg FAE to about 200 mg FAE, about 105 mg FAE to about 210 mg FAE, about 105 mg FAE to about 220 mg FAE, about 105 mg FAE to about 230 mg FAE, about 105 mg FAE to about 240 mg FAE, about 105 mg FAE to about 400 mg FAE, about 105 mg FAE to about 420 mg FAE, about 105 mg FAE to about 430 mg FAE, about 105 mg FAE to about 440 mg FAE, about 105 mg FAE to about 460 mg FAE, about 105 mg FAE to about 480 mg FAE, about 110 mg FAE to about 115 mg FAE, about 110 mg FAE to about 120 mg FAE, about 110 mg FAE to about 200 mg FAE, about 110 mg FAE to about 210 mg FAE, about 110 mg FAE to about 220 mg FAE, about 110 mg FAE to about 230 mg FAE, about 110 mg FAE to about 240 mg FAE, about 110 mg FAE to about 400 mg FAE, about 110 mg FAE to about 420 mg FAE, about 120 mg FAE to about 430 mg FAE, about 110 mg FAE to about 440 mg FAE, about 110 mg FAE to about 460 mg FAE, about 110 mg FAE to about 480 mg FAE, about 115 mg FAE to about 120 mg FAE, about 115 mg FAE to about 200 mg FAE, about 115 mg FAE to about 210 mg FAE, about 115 mg FAE to about 220 mg FAE, about 115 mg FAE to about 230 mg FAE, about 115 mg FAE to about 240 mg FAE, about 115 mg FAE to about 400 mg FAE, about 115 mg FAE to about 420 mg FAE, about 115 mg FAE to about 430 mg FAE, about 115 mg FAE to about 440 mg FAE, about 115 mg FAE to about 460 mg FAE, about 115 mg FAE to about 480 mg FAE, about 120 mg FAE to about 200 mg FAE, about 120 mg FAE to about 210 mg FAE, about 120 mg FAE to about 220 mg FAE, about 120 mg FAE to about 230 mg FAE, about 120 mg FAE to about 240 mg FAE, about 120 mg FAE to about 400 mg FAE, about 120 mg FAE to about 420 mg FAE, about 120 mg FAE to about 430 mg FAE, about 120 mg FAE to about 440 mg FAE, about 120 mg FAE to about 460 mg FAE, about 120 mg FAE to about 480 mg FAE, about 200 mg FAE to about 210 mg FAE, about 200 mg FAE to about 220 mg FAE, about 200 mg FAE to about 230 mg FAE, about 200 mg FAE to about 240 mg FAE, about 200 mg FAE to about 400 mg FAE, about 200 mg FAE to about 420 mg FAE, about 200 mg FAE to about 430 mg FAE, about 200 mg FAE to about 440 mg FAE, about 200 mg FAE to about 460 mg FAE, about 200 mg FAE to about 480 mg FAE, about 210 mg FAE to about 220 mg FAE, about 210 mg FAE to about 230 mg FAE, about 210 mg FAE to about 240 mg FAE, about 210 mg FAE to about 400 mg FAE, about 210 mg FAE to about 420 mg FAE, about 210 mg FAE to about 430 mg FAE, about 210 mg FAE to about 440 mg FAE, about 210 mg FAE to about 460 mg FAE, about 210 mg FAE to about 480 mg FAE, about 220 mg FAE to about 230 mg FAE, about 220 mg FAE to about 240 mg FAE, about 220 mg FAE to about 400 mg FAE, about 220 mg FAE to about 420 mg FAE, about 220 mg FAE to about 430 mg FAE, about 220 mg FAE to about 440 mg FAE, about 220 mg FAE to about 460 mg FAE, about 220 mg FAE to about 480 mg FAE, about 230 mg FAE to about 240 mg FAE, about 230 mg FAE to about 400 mg FAE, about 230 mg FAE to about 420 mg FAE, about 230 mg FAE to about 430 mg FAE, about 230 mg FAE to about 440 mg FAE, about 230 mg FAE to about 460 mg FAE, about 230 mg FAE to about 480 mg FAE, about 240 mg FAE to about 400 mg FAE, about 240 mg FAE to about 420 mg FAE, about 240 mg FAE to about 430 mg FAE, about 240 mg FAE to about 440 mg FAE, about 240 mg FAE to about 460 mg FAE, about 240 mg FAE to about 480 mg FAE, about 400 mg FAE to about 420 mg FAE, about 400 mg FAE to about 430 mg FAE, about 400 mg FAE to about 440 mg FAE, about 400 mg FAE to about 460 mg FAE, about 400 mg FAE to about 480 mg FAE, about 420 mg FAE to about 430 mg FAE, about 420 mg FAE to about 440 mg FAE, about 420 mg FAE to about 460 mg FAE, about 420 mg FAE to about 480 mg FAE, about 430 mg FAE to about 440 mg FAE, about 430 mg FAE to about 460 mg FAE, about 430 mg FAE to about 480 mg FAE, about 440 mg FAE to about 460 mg FAE, about 440 mg FAE to about 480 mg FAE, or about 460 mg FAE to about 480 mg FAE, including all integers and fractions within the specified ranges.

In another embodiment, the effective amount of fumarate ester can comprise, but is not limited to, about 70 mg FAE to about 480 mg FAE (e.g., 70-480 mg FAE), including all integers and fractions within the specified range. In one aspect, the daily effective amount can comprise, but is not limited to, an effective amount of about 70 mg to about 90 mg FAE, about 75 mg to about 95 mg FAE, about 80 mg to about 100 mg FAE, about 85 mg to about 105 mg FAE, about 90 mg to about 105 mg FAE, about 95 mg to about 108 mg FAE, about 100 mg to about 110 mg FAE, about 100 mg to about 115 mg FAE, about 100 mg to about 120 mg FAE, about 105 mg to about 110 mg FAE, about 105 mg to about 115 mg FAE, about 105 mg to about 120 mg FAE, about 105 mg to about 125 mg FAE, about 110 mg to about 120 mg FAE, about 110 mg to about 125 mg FAE, about 115 mg FAE to about 120 mg FAE, about 115 mg FAE to about 125 mg FAE, about 100 mg to about 200 mg FAE, about 105 mg to about 210 mg FAE, about 110 mg to about 220 mg FAE, about 115 mg FAE to about 230 mg FAE, about 120 mg to about 240 mg FAE, about 200 mg to about 220 mg FAE, about 210 mg to about 240 mg FAE, about 220 mg to about 250 mg FAE, about 400 mg to about 420 mg FAE; about 400 mg to about 430 mg FAE, about 400 mg to about 440 mg FAE, about 400 mg to about 450 mg FAE, about 400 mg to about 460 mg FAE, about 400 mg to about 480 mg FAE, about 410 mg to about 420 mg FAE; about 410 mg to about 430 mg FAE, about 410 mg to about 440 mg FAE, about 410 mg to about 450 mg FAE, about 410 mg to about 460 mg FAE, about 410 mg to about 480 mg FAE, about 420 mg to about 430 mg FAE, about 420 mg to about 440 mg FAE, about 420 mg to about 450 mg FAE, about 420 mg to about 460 mg FAE, about 420 mg to about 480 mg FAE, about 425 mg to about 430 mg FAE, about 425 mg to about 440 mg FAE; about 425 mg to about 450 mg FAE, about 425 mg to about 460 mg FAE, about 425 mg to about 480 mg FAE, about 430 mg to about 440 mg FAE, about 430 mg to about 450 mg FAE, about 430 mg to about 460 mg FAE, about 430 mg to about 480 mg FAE, about 440 mg to about 450 mg FAE, about 440 mg to about 460 mg FAE, or about 440 mg to about 480 mg FAE, including all integers and fractions within the specified ranges.

In one embodiment described herein, the FAE may comprise a solution or suspension having an active pharmaceutical ingredient load (e.g., drug load) of about 1% to about 65% by weight, including all integers and fractions within the specified range. In one embodiment, the drug load can comprise about 12% to about 16% by weight, including all integers and fractions within the specified range. In one embodiment, the drug load can comprise about 24% to about 32% by weight, including all integers and fractions within the specified range. In one embodiment, the drug load can comprise about 48% to about 64% by weight, including all integers and fractions within the specified range. In one embodiment, the drug load can comprise about 1%, about 2%, about 2.5%, about 5%, about 10%, about 15%, about 20%, about 25%, about 30%, about 35%, about 40%, about 45%, about 40%, about 50%, about 60%, about 65%, or even higher, by weight. In one embodiment, the drug load can comprise 13.3%, 14.0%, 14.4%, 14.7%, 15.3%, 16.0%, 26.7%, 28.0%, 28.8%, 29.3%, 30.7%, 32.0%, 53.3%, 56.0%, 57.6%, 58.7%, 61.3%, or 64.0%, each by weight. In one aspect, the drug load is about 20% by weight. In one aspect, the drug load is about 30% by weight. In one aspect, the drug load is about 40% by weight. In one aspect, the drug load is about 50% by weight. In one aspect, the drug load is about 60% by weight. In one aspect, the drug load is about 28% by weight. In one aspect, the drug load is about 32% by weight. In one aspect, the drug load is about 44% by weight. In one embodiment, the drug load is about 48% by weight. In one embodiment, the drug load is about 56% by weight.

In one embodiment described herein, pharmaceutical composition can comprise about 0.4 mmol FAE to about 4.0 mmol FAE, including all integers and fractions within the specified range. In one embodiment, the pharmaceutical composition comprises 0.4 mmol FAE, 0.5 mmol FAE, 0.6 mmol FAE, 0.7 mmol FAE, 0.8 mmol FAE, 0.9 mmol FAE, 1.0 mmol FAE, 1.1 mmol FAE, 1.2 mmol FAE, 1.3 mmol FAE, 1.4 mmol FAE, 1.5 mmol FAE, 1.6 mmol FAE, 1.7 mmol FAE, 1.8 mmol FAE, 1.9 mmol FAE, 2.0 mmol FAE, 2.1 mmol FAE, 2.2 mmol FAE, 2.3 mmol FAE, 2.4 mmol FAE, 2.5 mmol FAE, 2.6 mmol FAE, 2.7 mmol FAE, 2.8 mmol FAE, 2.9 mmol FAE, 3.0 mmol FAE, 3.1 mmol FAE, 3.2 mmol FAE, 3.3 mmol FAE, 3.4 mmol FAE, 3.5 mmol FAE, 3.6 mmol FAE, 3.7 mmol FAE, 3.8 mmol FAE, 3.9 mmol FAE, or 4.0 mmol FAE.

One embodiment described herein is a pharmaceutical dosage form comprising any one of the pharmaceutical compositions described herein for administration to a subject having a general autoimmune or neurodegenerative disorder, including but not limited to multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject; and wherein the administration does not require titration of the pharmaceutical composition.

Another embodiment described herein is a method for treating, retarding the progression of, prophylaxis of, delaying the onset of, ameliorating, or reducing the symptoms of multiple sclerosis or psoriasis comprising the administration of a therapeutically effective amount of one or more fumarate esters comprising any one of the pharmaceutical compositions described herein to a subject with multiple sclerosis, wherein the administration is sufficient to achieve a reduction of about 0.224 annualized relapse rate relative to baseline in the subject without substantially inducing one or more of flushing, abdominal pain, diarrhea, and nausea in the subject. In one aspect, after administration of any one the pharmaceutical compositions described herein, the subject experiences one or more of flushing, abdominal pain, diarrhea, and nausea at a rate of less than about 10%. In another aspect, the endpoint may be less than about 2%, about 5%, about 10%, about 15%, about 20%, about 25%, about 30%, about 35%, about 45%, about 50%, or greater than about 50%.

Another embodiment described herein is a pharmaceutical composition and a method for treating, retarding the progression of, delaying the onset of, prophylaxis of, amelioration of, or reducing the symptoms of a general autoimmune or neurodegenerative disorder, including but not limited to multiple sclerosis or psoriasis, the method comprising the administration of a therapeutically effective amount of one or more fumarate esters comprising any one of the pharmaceutical compositions described herein to a subject in need thereof, wherein the subject achieves a reduction of annualized relapse rate relative to baseline without substantially experiencing one or more of flushing, abdominal pain, diarrhea, and nausea. In another aspect, the endpoint may be less than about 2%, about 5%, about 10%, about 15%, about 20%, about 25%, about 30%, about 35%, about 45%, about 50%, or greater than about 50%, relative to baseline.

Endpoints for treating multiple sclerosis using fumarate esters are described in the TECFIDERA® Prescribing Information (Biogen Idec Inc.), and U.S. Patent Application Publication No. US 2014/0163100, each of which is incorporated by reference herein for such teachings. Other pharmaceutical compositions and methods for treating multiple sclerosis are described in U.S. Pat. Nos. 6,509,376; 7,320,999; 7,619,001; 7,803,840; 8,399,514; 8,524,773; and 8,759,393, and International Patent Application Publication No. WO 2013/119677, each of which is incorporated by reference herein for such teachings.

Another embodiment described herein is a pharmaceutical composition for administration to a subject with multiple sclerosis or psoriasis comprising a therapeutically effective amount of one or more fumarate esters, wherein the subject achieves a reduction of annualized relapse rate relative to baseline without substantially experiencing one or more of flushing, abdominal pain, diarrhea, and nausea. In one aspect the reduction of annualized relapse rate may be about 1%, about 2%, about 5%, about 10%, about 15%, about 20%, about 25%, about 30%, about 35%, about 45%, about 50%, or greater than about 50%.

For the treatment of multiple sclerosis (e.g., relapsing forms of MS such as RRMS), the dosage form administered to the subject or subject in need thereof comprises an enteric soft capsule comprising micronized solid particles of a fumarate ester as the only active ingredient or in combination with one or more NSAIDS (e.g., aspirin) or leukotriene receptor antagonists (e.g., montelukast or zafirlukast). In one aspect, the effective amount of fumarate ester is about 360 mg to about 480 mg FAE per day and the subjects can receive the effective amount, e.g., about 80 mg to about 120 mg FAE quater in die (QID), in the form of four capsules a day, to be taken orally, including all integers and fractions within the specified ranges. In another aspect, the effective amount is about 80 mg to about 110 mg FAE quater in die (QID). In another aspect, the effective amount is about 90 mg to about 107 mg FAE quater in die (QID). In another aspect, the effective amount is about 102 mg to about 115 mg FAE quater in die (QID). In one aspect, the effective amount of fumarate ester is about 360 mg to about 480 mg FAE per day and the subjects can receive the effective amount, e.g., about 180 mg to about 240 mg FAE bis in die (BID), in the form of two capsules a day, to be taken orally, including all integers and fractions within the specified ranges. In another aspect, the effective amount is about 205 mg to about 230 mg FAE BID. In a further aspect, the effective amount is about 210 mg to about 225 mg FAE BID, or about 215 mg to 220 mg FAE BID. In another aspect, the effective amount of FAE is about 360 mg to about 480 mg FAE per day and the subjects can receive the effective amount, e.g., about 360 to about 480 mg FAE quaque die (QD), in the form of one capsule a day, to be taken orally, including all integers and fractions within the specified ranges.

In another embodiment, for the treatment of multiple sclerosis the daily effective amount of FAE is from 80 mg FAE to 85 mg FAE, 80 mg FAE to 90 mg FAE, 80 mg FAE to 95 mg FAE, 85 mg FAE to 100 mg FAE, 85 mg FAE to 90 mg FAE, 85 mg FAE to 95 mg FAE, 90 mg FAE to 100 mg FAE, 90 mg FAE to 105 mg FAE, 90 mg FAE to 95 mg FAE, 95 mg FAE to 100 mg FAE, 95 mg FAE to 105 mg FAE, 95 mg FAE to 110 mg FAE, 100 mg FAE to 105 mg FAE, 100 mg FAE to 110 mg FAE, 100 mg FAE to 115 mg FAE, 105 mg FAE to 110 mg FAE, 105 mg FAE to 115 mg FAE, 105 mg FAE to 120 mg FAE, 110 mg FAE to 115 mg FAE, 110 mg FAE to 120 mg FAE, 110 mg FAE to 125 mg FAE, 115 mg FAE to 120 mg FAE, 115 mg FAE to 125 mg FAE, 115 mg FAE to 130 mg FAE, 120 mg FAE to 125 mg FAE, 120 mg FAE to 130 mg FAE, 120 mg FAE to 135 mg FAE, 125 mg FAE to 130 mg FAE, 125 mg FAE to 135 mg FAE, 125 mg FAE to 140 mg FAE, 130 mg FAE to 135 mg FAE, 130 mg FAE to 140 mg FAE, 130 mg FAE to 145 mg FAE, 135 mg FAE to 140 mg FAE, 135 mg FAE to 145 mg FAE, 135 mg FAE to 150 mg FAE, 140 mg FAE to 145 mg FAE, 140 mg FAE to 150 mg FAE, 140 mg FAE to 155 mg FAE, 145 mg FAE to 150 mg FAE, 145 mg FAE to 155 mg FAE, 145 mg FAE to 160 mg FAE, 150 mg FAE to 155 mg FAE, 150 mg FAE to 160 mg FAE, 150 mg FAE to 165 mg FAE, 155 mg FAE to 160 mg FAE, 155 mg FAE to 165 mg FAE, 155 mg FAE to 170 mg FAE, 160 mg FAE to 165 mg FAE, 160 mg FAE to 170 mg FAE, 160 mg FAE to 175 mg FAE, 165 mg FAE to 170 mg FAE, 165 mg FAE to 175 mg FAE, 165 mg FAE to 180 mg FAE, 170 mg FAE to 175 mg FAE, 170 mg FAE to 180 mg FAE, 170 mg FAE to 185 mg FAE, 175 mg FAE to 180 mg FAE, 175 mg FAE to 185 mg FAE, 175 mg FAE to 190 mg FAE, 180 mg FAE to 185 mg FAE, 180 mg FAE to 190 mg FAE, 180 mg FAE to 195 mg FAE, 185 mg FAE to 190 mg FAE, 185 mg FAE to 195 mg FAE, 185 mg FAE to 200 mg FAE, 190 mg FAE to 195 mg FAE, 190 mg FAE to 200 mg FAE, 190 mg FAE to 205 mg FAE, 195 mg FAE to 200 mg FAE, 195 mg FAE to 205 mg FAE, 195 mg FAE to 210 mg FAE, 200 mg FAE to 205 mg FAE, 200 mg FAE to 210 mg FAE, 200 mg FAE to 215 mg FAE, 205 mg FAE to 210 mg FAE, 205 mg FAE to 215 mg FAE, 205 mg FAE to 220 mg FAE, 210 mg FAE to 215 mg FAE, 210 mg FAE to 220 mg FAE, 210 mg FAE to 225 mg FAE, 215 mg FAE to 220 mg FAE, 215 mg FAE to 225 mg FAE, 215 mg FAE to 230 mg FAE, 220 mg FAE to 225 mg FAE, 220 mg FAE to 230 mg FAE, 220 mg FAE to 235 mg FAE, 225 mg FAE to 230 mg FAE, 225 mg FAE to 235 mg FAE, 225 mg FAE to 240 mg FAE, 230 mg FAE to 235 mg FAE, 230 mg FAE to 240 mg FAE, 230 mg FAE to 245 mg FAE, 235 mg FAE to 240 mg FAE, 235 mg FAE to 245 mg FAE, 235 mg FAE to 250 mg FAE, 240 mg FAE to 245 mg FAE, 240 mg FAE to 250 mg FAE, 240 mg FAE to 255 mg FAE, 245 mg FAE to 250 mg FAE, 245 mg FAE to 255 mg FAE, 245 mg FAE to 260 mg FAE, 250 mg FAE to 255 mg FAE, 250 mg FAE to 260 mg FAE, 250 mg FAE to 265 mg FAE, 255 mg FAE to 260 mg FAE, 255 mg FAE to 265 mg FAE, 255 mg FAE to 270 mg FAE, 260 mg FAE to 265 mg FAE, 260 mg FAE to 270 mg FAE, 260 mg FAE to 275 mg FAE, 265 mg FAE to 270 mg FAE, 265 mg FAE to 275 mg FAE, 265 mg FAE to 280 mg FAE, 270 mg FAE to 275 mg FAE, 270 mg FAE to 280 mg FAE, 270 mg FAE to 285 mg FAE, 275 mg FAE to 280 mg FAE, 275 mg FAE to 285 mg FAE, 275 mg FAE to 290 mg FAE, 280 mg FAE to 285 mg FAE, 280 mg FAE to 290 mg FAE, 280 mg FAE to 295 mg FAE, 285 mg FAE to 290 mg FAE, 285 mg FAE to 295 mg FAE, 285 mg FAE to 300 mg FAE, 290 mg FAE to 295 mg FAE, 290 mg FAE to 300 mg FAE, 290 mg FAE to 305 mg FAE, 295 mg FAE to 300 mg FAE, 295 mg FAE to 305 mg FAE, 295 mg FAE to 310 mg FAE, 300 mg FAE to 305 mg FAE, 300 mg FAE to 310 mg FAE, 300 mg FAE to 315 mg FAE, 305 mg FAE to 310 mg FAE, 305 mg FAE to 315 mg FAE, 305 mg FAE to 320 mg FAE, 310 mg FAE to 315 mg FAE, 310 mg FAE to 320 mg FAE, 310 mg FAE to 325 mg FAE, 315 mg FAE to 320 mg FAE, 315 mg FAE to 325 mg FAE, 315 mg FAE to 330 mg FAE, 320 mg FAE to 325 mg FAE, 320 mg FAE to 330 mg FAE, 320 mg FAE to 335 mg FAE, 325 mg FAE to 330 mg FAE, 325 mg FAE to 335 mg FAE, 325 mg FAE to 340 mg FAE, 330 mg FAE to 335 mg FAE, 330 mg FAE to 340 mg FAE, 330 mg FAE to 345 mg FAE, 335 mg FAE to 340 mg FAE, 335 mg FAE to 345 mg FAE, 335 mg FAE to 350 mg FAE, 340 mg FAE to 345 mg FAE, 340 mg FAE to 350 mg FAE, 340 mg FAE to 355 mg FAE, 345 mg FAE to 350 mg FAE, 345 mg FAE to 355 mg FAE, 345 mg FAE to 360 mg FAE, 350 mg FAE to 355 mg FAE, 350 mg FAE to 360 mg FAE, 350 mg FAE to 365 mg FAE, 355 mg FAE to 360 mg FAE, 355 mg FAE to 365 mg FAE, 355 mg FAE to 370 mg FAE, 360 mg FAE to 365 mg FAE, 360 mg FAE to 370 mg FAE, 360 mg FAE to 375 mg FAE, 365 mg FAE to 370 mg FAE, 365 mg FAE to 375 mg FAE, 365 mg FAE to 380 mg FAE, 370 mg FAE to 375 mg FAE, 370 mg FAE to 380 mg FAE, 370 mg FAE to 385 mg FAE, 375 mg FAE to 380 mg FAE, 375 mg FAE to 385 mg FAE, 375 mg FAE to 390 mg FAE, 380 mg FAE to 385 mg FAE, 380 mg FAE to 390 mg FAE, 380 mg FAE to 395 mg FAE, 385 mg FAE to 390 mg FAE, 385 mg FAE to 395 mg FAE, 385 mg FAE to 400 mg FAE, 390 mg FAE to 395 mg FAE, 390 mg FAE to 400 mg FAE, 390 mg FAE to 405 mg FAE, 395 mg FAE to 400 mg FAE, 395 mg FAE to 405 mg FAE, 395 mg FAE to 410 mg FAE, 400 mg FAE to 405 mg FAE, 400 mg FAE to 410 mg FAE, 400 mg FAE to 415 mg FAE, 405 mg FAE to 410 mg FAE, 405 mg FAE to 415 mg FAE, 405 mg FAE to 420 mg FAE, 410 mg FAE to 415 mg FAE, 410 mg FAE to 420 mg FAE, 410 mg FAE to 425 mg FAE, 415 mg FAE to 420 mg FAE, 415 mg FAE to 425 mg FAE, 415 mg FAE to 430 mg FAE, 420 mg FAE to 425 mg FAE, 420 mg FAE to 430 mg FAE, 420 mg FAE to 435 mg FAE, 425 mg FAE to 430 mg FAE, 425 mg FAE to 435 mg FAE, 425 mg FAE to 440 mg FAE, 430 mg FAE to 435 mg FAE, 430 mg FAE to 440 mg FAE, 430 mg FAE to 445 mg FAE, 435 mg FAE to 440 mg FAE, 435 mg FAE to 445 mg FAE, 435 mg FAE to 450 mg FAE, 440 mg FAE to 445 mg FAE, 440 mg FAE to 450 mg FAE, 440 mg FAE to 455 mg FAE, 445 mg FAE to 450 mg FAE, 445 mg FAE to 455 mg FAE, 445 mg FAE to 460 mg FAE, 450 mg FAE to 455 mg FAE, 450 mg FAE to 460 mg FAE, 450 mg FAE to 465 mg FAE, 455 mg FAE to 460 mg FAE, 455 mg FAE to 465 mg FAE, 455 mg FAE to 470 mg FAE, 460 mg FAE to 465 mg FAE, 460 mg FAE to 470 mg FAE, 460 mg FAE to 475 mg FAE, 465 mg FAE to 470 mg FAE, 465 mg FAE to 475 mg FAE, 465 mg FAE to 480 mg FAE, 470 mg FAE to 475 mg FAE, 470 mg FAE to 480 mg FAE, or 475 mg FAE to 480 mg FAE. The effective amount can be administered in one or more doses, once, twice, three, four, or more times per day.

For the treatment of autoimmune disorders, including multiple sclerosis and psoriasis, the dosage form administered to the subject or subject in need thereof comprises an enteric soft capsule comprising micronized solid particles of a fumarate ester as the only active ingredient or in combination with one or more NSAIDS (e.g., aspirin) or leukotriene receptor antagonists (e.g., montelukast or zafirlukast). In one aspect, the effective amount of fumarate ester is about 360 mg to about 480 mg FAE per day and the subjects can receive the effective amount, e.g., about 80 mg to about 120 mg FAE quater in die (QID), in the form of four capsules a day, to be taken orally, including all integers and fractions within the specified ranges. In one aspect, the effective amount of fumarate ester is about 360 mg to about 480 mg FAE per day and the subjects can receive the effective amount, e.g., about 180 mg to about 240 mg FAE bis in die (BID), in the form of two capsules a day, to be taken orally, including all integers and fractions within the specified ranges. In another aspect, the effective amount of fumarate ester is about 360 mg to about 480 mg FAE per day and the subjects can receive the effective amount, e.g., about 360 mg to about 480 mg FAE quaque die (QD), in the form of one capsule a day, to be taken orally, including all integers and fractions within the specified ranges.

Fumarate esters can cause flushing and gastrointestinal (GI) side effects in some subjects. While the side effects generally subside soon after subjects start on the treatment, in one aspect the starting dose is about 80 mg to about 120 mg FAE BID orally for the first 7 days, including all integers and fractions within the specified range. The dose is increased to the effective dose of about 180 mg to about 240 mg FAE BID (e.g., about 360 mg to about 480 mg FAE per day), including all integers and fractions within the specified ranges. In another aspect, the starting dose is about 180 mg to about 240 mg FAE BID orally for the first 7 days, including all integers and fractions within the specified ranges. The dose is increased to the effective dose of about 360 mg to about 480 mg FAE QD (e.g., about 360 mg to about 480 mg FAE per day), including all integers and fractions within the specified ranges. For those subjects who experience GI or flushing side effects, taking FAE with food can improve tolerability. In one aspect described herein, FAE is administered after a meal. In another aspect described herein, FAE is administered after a high-fat meal to reduce or ameliorate the one or more symptoms of flushing, abdominal pain, diarrhea, and nausea in the subject.

In one embodiment, the pharmaceutical compositions described herein can be administered without titration of the pharmaceutical composition. In one aspect, the pharmaceutical compositions can be administered without titration and without substantially inducing one or more of flushing, abdominal pain, diarrhea, and nausea in the subject.

In one embodiment, the pharmaceutical composition described herein does not elicit the flushing and gastrointestinal side effects when the dose is about 80 mg to about 120 mg FAE quater in die (QID) (e.g., 360 mg to about 480 mg FAE per day), including all integers and fractions within the specified ranges. In another embodiment, the pharmaceutical composition described herein does not elicit the flushing and gastrointestinal side effects when the dose is about 180 mg to about 240 mg FAE bis in die (BID) (e.g., 360 mg to about 480 mg FAE per day), including all integers and fractions within the specified ranges. In one embodiment, the pharmaceutical composition described herein does not elicit the flushing and gastrointestinal side effects when the dose is about 360 mg to about 480 mg FAE quaque die (QD) (e.g., 360 mg to about 480 mg FAE per day), including all integers and fractions within the specified ranges.

In one embodiment, the pharmaceutical composition described herein does not elicit flushing and gastrointestinal side effects when the effective amount is about 180 mg FAE quaque die (QD) (e.g., 180 mg FAE per day). In another embodiment, the pharmaceutical composition described herein does not elicit the flushing and gastrointestinal side effects when the effective amount is about 180 mg to about 240 mg FAE quaque die (QD) (e.g., 180 mg to about 240 mg FAE per day), including all integers and fractions within the specified ranges. In another embodiment, the pharmaceutical composition described herein does not elicit the flushing and gastrointestinal side effects when the effective amount is about 360 mg to about 480 mg FAE quaque die (QD) (e.g., 360 mg to about 480 mg FAE per day), including all integers and fractions within the specified ranges.

In another aspect, the administration of about 325 mg of non-enteric coated aspirin 30-minutes prior to FAE dosing can reduce the occurrence and severity of flushing. In one aspect, subjects who experience flushing with gastrointestinal side effects may reduce the dose to about 100 mg to about 120 mg FAE BID temporarily, including all integers and fractions within the specified range. Within a month, the effective dose of about 180 mg to about 240 mg FAE BID should be resumed, including all integers and fractions within the specified range. In another aspect, subjects who experience flushing with gastrointestinal side effects may reduce the dose to about 180 mg to about 240 mg FAE BID temporarily, including all integers and fractions within the specified range. Within a month, the effective dose of about 360 mg to about 480 mg FAE QD should be resumed, including all integers and fractions within the specified range.

In one embodiment, a subject administered a FAE pharmaceutical composition described herein may take one or more non-steroidal anti-inflammatory drugs (NSAID) before (for example, about 10 minutes to an hour, e.g., about 30 minutes before) taking a FAE pharmaceutical composition described herein. In one embodiment, the subject administered a dosage form takes the one or more non-steroidal anti-inflammatory drugs to reduce flushing. In one embodiment, the one or more non-steroidal anti-inflammatory drugs comprise aspirin, ibuprofen, naproxen, ketoprofen, celecoxib, or combinations thereof. The one or more non-steroidal anti-inflammatory drugs can be administered in an amount of about 50 mg to about 500 mg before taking the dosage form described herein. In one embodiment, a subject takes 325 mg aspirin about 30-minutes before taking the dosage forms described herein.

In another embodiment, a subject administered a FAE pharmaceutical composition described herein may take one or more leukotriene receptor antagonists. In another embodiment, a subject administered a FAE pharmaceutical composition described herein may take 10 to 20 mg of montelukast (Singulair®) or zafirlukast)(Accolate®).

In another embodiment described herein, subjects are orally administered one or more non-steroidal anti-inflammatory drugs before taking the dosage form described herein exhibit the same pharmacokinetic properties (e.g., $C_{max}$ and AUC) as subjects orally administered the dosage form described herein without administering one or more non-steroidal anti-inflammatory drugs (e.g., aspirin, ibuprofen, naproxen, ketoprofen, celecoxib, or combinations thereof). The NSAID can be administered about 30-minutes before taking the dosage form described herein.

In one embodiment described herein, a subject is administered one or more soft capsules containing about 80 mg to about 480 mg FAE, one or more times daily for a total daily dose of about 360 mg to about 480 mg, including all integers and fractions within the specified range. In one aspect, the pharmaceutical composition comprises an immediate release, delayed release, controlled release, or extended release formulation of a fumarate ester. In one embodiment, the matrix is a controlled release matrix. In another embodiment, the matrix is a delayed release matrix. In another embodiment, the matrix is an extended release matrix. In another aspect, the pharmaceutical composition comprises an enteric soft capsule.

In one embodiment, subjects having a general autoimmune or neurodegenerative disorder, including but not limited to multiple sclerosis or psoriasis, are administered one or more enteric soft capsules containing about 80 mg to about 120 mg FAE, twice-daily for a total daily dose of about 360 mg to about 480 mg, wherein the enteric soft capsule comprises solid microparticles of FAE in a matrix, including all integers and fractions within the specified ranges. In one embodiment, the matrix is a controlled release matrix. In one embodiment, the matrix is a delayed release matrix. In one embodiment, the matrix is an extended release matrix.

In one embodiment, subjects having a general autoimmune or neurodegenerative disorder, including but not limited to multiple sclerosis or psoriasis, are administered one or more enteric soft capsules containing about 180 mg to about 240 mg FAE, twice-daily for a total daily dose of about 360 mg to about 480 mg, wherein the enteric soft capsule comprises solid microparticles of FAE in a matrix, including all integers and fractions within the specified ranges. In one embodiment, the matrix is a controlled release matrix. In another embodiment, the matrix is a delayed release matrix. In another embodiment, the matrix is an extended release matrix.

In one embodiment, subjects having a general autoimmune or neurodegenerative disorder, including but not limited to multiple sclerosis or psoriasis, are administered an enteric soft capsule containing about 360 mg to about 480 mg FAE, once daily for a total daily dose of about 360 mg to about 480 mg, wherein the enteric soft capsule comprises solid microparticles of FAE in a matrix, including all integers and fractions within the specified ranges. In one embodiment, the matrix is a controlled release matrix. In another embodiment, the matrix is a delayed release matrix. In another embodiment, the matrix is an extended release matrix.

Pharmacokinetics of fumarate esters, particularly DMF, are described by Sheikh et al., *Clinical Therapeutics* 35(10): 1582-1594 (2013), which is incorporated by reference herein for such teachings.

In one aspect, the pharmaceutical composition described herein is provided in a dosage form containing a total amount of about 80 mg to about 120 mg of a fumarate ester, wherein subjects administered the dosage exhibit a mean plasma monomethyl fumarate $C_{max}$ ranging from about 0.2 mg/L to about 2.41 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 0.4 mg/L to about 2.41 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 1.5 mg/L to about 3.4 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 1.03 mg/L to about 2.41 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 0.4 mg/L to about 0.75 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 0.76 mg/L to about 1.03 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 1.04 mg/L to about 1.75 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ ranging from about 1.75 mg/L to about 2.41 mg/L, including all integers and fractions within the specified ranges. In another aspect, the composition is provided in a dosage form containing a total amount of about 80 mg to about 120 mg of a fumarate ester, wherein subjects administered the dosage exhibit a mean plasma monomethyl fumarate $C_{max}$ of at least 0.4 mg/L, at least 0.5 mg/L, at least 0.6 mg/L, at least 0.7 mg/L, at least 0.8 mg/L, at least 0.9 mg/L, at least 1 mg/L, at least 1.1 mg/L, at least 1.2 mg/L, at least 1.3 mg/L, at least 1.4 mg/L, at least 1.5 mg/L, at least 1.6 mg/L, at least 1.7 mg/L, at least 1.8 mg/L, at least 1.9 mg/L, at least 2 mg/L, at least 2.1 mg/L, at least 2.2 mg/L, at least 2.3 mg/L, at least 2.4 mg/L, at least 2.5 mg/L, at least 2.6 mg/L, at least 2.7 mg/L, at least 2.8 mg/L, at least 2.9 mg/L, at least 3 mg/L, at least 3.1 mg/L, at least 3.2 mg/L, at least 3.3 mg/L, or at least 3.4 mg/L.

In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 1.0 h·mg/L to about 15.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 2.01 h·mg/L to about 5.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 1.0 h·mg/L to about 5.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 11.3 h·mg/L to about 15.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 3.2 h·mg/L to about 11.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ ranging from about 5.2 h·mg/L to about 11.2 h·mg/L, including all integers and fractions within the specified ranges. In another aspect, the composition is provided in a dosage form containing a total amount of about 80 mg to about 120 mg of a fumarate ester, wherein subjects administered the dosage form four times daily exhibit a mean plasma monomethyl fumarate $AUC_{overall}$ at least about 1.0 h·mg/L, at least 1.2 h·mg/L, at least 1.4 h·mg/L, at least 1.6 h·mg/L, at least 1.8 h·mg/L, at least 2.0 h·mg/L, at least 2.3 h·mg/L, at least about 2.6 h·mg/L, at least about 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5.0 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4·h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.3 h·mg/L, at least 13.6 h·mg/L, at least 13.9 h·mg/L, at least 14.2 h·mg/L, at least 14.5 h·mg/L, at least 14.8 h·mg/L, or at least 15.2 h·mg/L.

In another aspect, the composition is provided in a dosage form containing a total amount of about 80 mg to about 120 mg of a fumarate ester, wherein subjects administered the dosage form exhibit a mean plasma monomethyl fumarate $AUC_{0 \to 12h}$ ranging from about 0.5 h·mg/L to about 5.5 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to 12h}$ ranging from about 0.5 h·mg/L to about 2.5 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to 12h}$ ranging from about 2.6 h·mg/L to about 5.5 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to 12h}$ of at least about 0.5 h·mg/L, at least 1.0 h·mg/L, at least 1.2 h·mg/L, at least 1.4 h·mg/L, at least 1.6 h·mg/L, at least 1.8 h·mg/L, at least 2.0 h·mg/L, at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, or at least 5.5 h·mg/L.

In another aspect, the composition is provided in a dosage form containing a total amount of about 80 mg to about 120 mg of a fumarate ester, wherein subjects administered the dosage form exhibit a mean plasma monomethyl fumarate $AUC_{0 \to \infty}$ ranging from about 0.5 h·mg/L to about 5.6 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to \infty}$ ranging from about 0.5 h·mg/L to about 2.6 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to \infty}$ ranging from about 2.6 h·mg/L to about 5.5 h·mg/L, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $AUC_{0 \to \infty}$ of at least about 0.5 h·mg/L, at least 1.0 h·mg/L, at least 1.2 h·mg/L, at least 1.4 h·mg/L, at least 1.6 h·mg/L, at least 1.8 h·mg/L, at least 2 h·mg/L, at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, or at least 5.5 h·mg/L.

In another aspect, the composition is provided in a dosage form containing a total amount of about 80 mg to about 120 mg of a fumarate ester, wherein subjects administered the dosage form exhibit a mean plasma monomethyl fumarate $T_{max}$ ranging from about 1.5 hours to about 8.5 hours, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $T_{max}$ ranging from about 1.6 hours to about 2.5 hours, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $T_{max}$ ranging from about 2.6 hours to about 5 hours, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $T_{max}$ ranging from about 5.1 hours to about 7.5 hours, including all integers and fractions within the specified ranges. In another aspect, the composition is provided in a dosage form containing a total amount of about 80 mg to about 120 mg of a fumarate ester, wherein subjects administered the dosage form exhibit a mean plasma monomethyl fumarate $T_{max}$ ranging from about 7.6 hours to about 8.5 hours, including all integers and fractions within the specified ranges. In another aspect, the composition is provided in a dosage form containing a total amount of about 240 mg to about 240 mg of a fumarate ester, wherein subjects administered the dosage form exhibit a mean plasma monomethyl fumarate $T_{max}$ of at least 1.6 hours, at least 1.8 hours, at least 2 hours, at least 2.2 hours, at least 2.4 hours, at least 2.6 hours, at least 2.8 hours, at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, at least 6.6 hours, at least 6.8 hours, at least 7 hours, at least 7.2 hours, at least 7.4 hours, at least 7.6 hours, at least 7.8 hours, at least 8 hours, at least 8.2 hours, or at least 8.4 hours.

In one embodiment described herein, a subject is administered a capsule containing about 180 mg to about 240 mg FAE, twice daily for a total daily dose of about 360 mg to about 480 mg, including all integers and fractions within the specified range. In one aspect, the pharmaceutical composition comprises an immediate release, delayed release, controlled release, or extended release formulation of a fumarate ester. In another aspect, the pharmaceutical composition comprises an enteric soft capsule.

In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 0.4 mg/L to about 2.41 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 1.0 mg/L to about 3.4 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 1.03 mg/L to about 2.41 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 0.4 mg/L to about 0.75 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 0.76 mg/L to about 1.03 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 1.04 mg/L to about 1.75 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ ranging from about 1.75 mg/L to about 2.41 mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $C_{max}$ of at least 0.4 mg/L, at least 0.5 mg/L, at least 0.6 mg/L, at least 0.7 mg/L, at least 0.8 mg/L, at least 0.9 mg/L, at least 1 mg/L, at least 1.1 mg/L, at least 1.2 mg/L, at least 1.3 mg/L, at least 1.4 mg/L, at least 1.5 mg/L, at least 1.6 mg/L, at least 1.7 mg/L, at least 1.8 mg/L, at least 1.9 mg/L, at least 2 mg/L, at least 2.1 mg/L, at least 2.2 mg/L, at least 2.3 mg/L, at least 2.4 mg/L, at least 2.5 mg/L, at least 2.6 mg/L, at least 2.7 mg/L, at least 2.8 mg/L, at least 2.9 mg/L, at least 3 mg/L, at least 3.1 mg/L, at least 3.2 mg/L, at least 3.3 mg/L, or at least 3.4 mg/L.

In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ ranging from about 1.0 h·mg/L to about 15.2 h·mg/L, including all integers and fractions within the specified ranges. In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ ranging from about 2.01 h·mg/L to about 5.2 h·mg/L, including all integers and fractions within the specified ranges. In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ ranging from about 1.0 h·mg/L to about 5.2 h·mg/L, including all integers and fractions within the specified ranges. In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ ranging from about 11.3 h·mg/L to about 15.2 h·mg/L, including all integers and fractions within the specified ranges. In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ ranging from about 4.8 h·mg/L to about 11.2 h·mg/L, including all integers and fractions within the specified ranges. In another aspect, the composition is provided in a dosage form containing a total amount of about 180 mg to about 240 mg of a fumarate ester, wherein subjects administered the dosage form twice-daily exhibit a mean plasma monomethyl fumarate $AUC_{overall}$ at least about 1.0 h·mg/L, at least 1.2 h·mg/L, at least 1.4 h·mg/L, at least 1.6 h·mg/L, at least 1.8 h·mg/L, at least 2.0 h·mg/L, at least 2.3 h·mg/L, at least about 2.6 h·mg/L, at least about 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5.0 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.3 h·mg/L, at least 13.6 h·mg/L, at least 13.9 h·mg/L, at least 14.2 h·mg/L, at least 14.5 h·mg/L, at least 14.8 h·mg/L, or at least 15.2 h·mg/L.

In another aspect, the composition is provided in a dosage form containing a total amount of about 180 mg to about 240 mg of a fumarate ester, wherein subjects administered the dosage form exhibit a mean plasma monomethyl fumarate $AUC_{0 \to 12h}$ ranging from about 1.0 h·mg/L to about 5.5 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to 12h}$ ranging from about 1.0 h·mg/L to about 2.5 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to 12h}$ ranging from about 2.6 h·mg/L to about 5.5 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to 12h}$ of at least about 1.0 h·mg/L, at least 1.2 h·mg/L, at least 1.4 h·mg/L, at least 1.6 h·mg/L, at least 1.8 h·mg/L, at least 2.0 h·mg/L, at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, or at least 5.5 h·mg/L.

In another aspect, the composition is provided in a dosage form containing a total amount of about 180 mg to about 240 mg of a fumarate ester, wherein subjects administered the dosage form exhibit a mean plasma monomethyl fumarate $AUC_{0 \to \infty}$ ranging from about 1.0 h·mg/L to about 5.6 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to \infty}$ ranging from about 1.0 h·mg/L to about 2.5 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to \infty}$ ranging from about 2.6 h·mg/L to about 5.5 h·mg/L, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $AUC_{0 \to \infty}$ of at least about 1.0 h·mg/L, at least 1.2 h·mg/L, at least 1.4 h·mg/L, at least 1.6 h·mg/L, at least 1.8 h·mg/L, at least 2 h·mg/L, at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, at least 5.5 h·mg/L, or at least 5.6 h·mg/L.

In another aspect, the composition is provided in a dosage form containing a total amount of about 180 mg to about 240 mg of a fumarate ester, wherein subjects administered the dosage form exhibit a mean plasma monomethyl fumarate $T_{max}$ ranging from about 1.5 hours to about 8.5 hours, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $T_{max}$ ranging from about 1.6 hours to about 2.5 hours, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $T_{max}$ ranging from about 2.6 hours to about 5 hours, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $T_{max}$ ranging from about 5.1 hours to about 7.5 hours, including all integers and fractions within the specified ranges. In another aspect, the composition is provided in a dosage form containing a total amount of about 180 mg to about 240 mg of a fumarate ester, wherein subjects administered the dosage form exhibit a mean plasma monomethyl fumarate $T_{max}$ ranging from about 7.6 hours to about 8.5 hours, including all integers and fractions within the specified ranges. In one aspect, the composition is provided in a dosage form containing a total amount of about 240 mg to about 240 mg of a fumarate ester, wherein subjects administered the dosage form exhibit a mean plasma monomethyl fumarate $T_{max}$ of at least 1.6 hours, at least 1.8 hours, at least 2 hours, at least 2.2 hours, at least 2.4 hours, at least 2.6 hours, at least 2.8 hours, at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, at least 6.6 hours, at least 6.8 hours, at least 7 hours, at least 7.2 hours, at least 7.4 hours, at least 7.6 hours, at least 7.8 hours, at least 8 hours, at least 8.2 hours, or at least 8.4 hours.

In one embodiment described herein, a subject is administered a capsule containing about 360 to about 480 mg FAE, once daily for a total daily dose of about 360 to about 480 mg, including all integers and fractions within the specified ranges. In one aspect, the pharmaceutical composition comprises an immediate release, delayed release, controlled release, or extended release formulation of a fumarate ester. In another aspect, the pharmaceutical composition comprises an enteric soft capsule. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 0.4 mg/L to about 5.2 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 1.5 mg/L to about 5.2 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 0.4 mg/L to about 0.75 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 0.76 mg/L to about 1.03 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 1.04 mg/L to about 1.75 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 1.75 mg/L to about 2.41 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 2.42 mg/L to about 3.5 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ ranging from about 3.6 mg/L to about 5.2 mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $C_{max}$ of at least about 1.0 mg/L, at least 1.1 mg/L, at least 1.2 mg/L, at least 1.3 mg/L, at least 1.4 mg/L, at least 1.5 mg/L, at least 1.6 mg/L, at least 1.7 mg/L, at least 1.8 mg/L, at least 1.9 mg/L, at least 2.0 mg/L, at least 2.1 mg/L, at least 2.2 mg/L, at least 2.3 mg/L, at least 2.4 mg/L, at least 2.5 mg/L, at least 2.6 mg/L, at least 2.7 mg/L, at least 2.8 mg/L, at least 2.9 mg/L, at least 3.0 mg/L, at least 3.1 mg/L, at least 3.2 mg/L, at least 3.3 mg/L, at least 3.4 mg/L, at least 3.5 mg/L, at least 3.6 mg/L, at least 3.7 mg/L, at least 3.8 mg/L, at least 3.9 mg/L, at least 4.0 mg/L, at least 4.1 mg/L, at least 4.2 mg/L, at least 4.3 mg/L, at least 4.4 mg/L, at least 4.5 mg/L, at least 4.6 mg/L, at least 4.7 mg/L, at least 4.8 mg/L, at least 4.9 mg/L, at least 5.0 mg/L, or at least 5.1 mg/L.

In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ ranging from about 1.0 h·mg/L to about 15.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ ranging from about 1.0 h·mg/L to about 2.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 42h}$ ranging from about 2.6 h·mg/L to about 5.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ ranging from about 5.6 h·mg/L to about 7.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ ranging from about 7.6 h·mg/L to about 10.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ ranging from about 10.5 h·mg/L to about 15.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0 \to 12h}$ of at least about 1.0 h·mg/L, at least 1.2 h·mg/L, at least 1.4 h·mg/L, at least 1.6 h·mg/L, at least 1.8 h·mg/L, at least 2.0 h·mg/L, at least 2.3 h·mg/L, at least 2.6 h·mg/L, at least 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.4 h·mg/L, at least 13.7 h·mg/L, at least 14 h·mg/L, at least 14.3 h·mg/L, at least 14.6 h·mg/L, at least 14.9 h·mg/L, at least 15.2 h·mg/L, or at least 15.5 h·mg/L.

In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 1.0 h·mg/L to about 15.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 1.5 h·mg/L to about 2.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 2.6 h·mg/L to about 5.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 5.6 h·mg/L to about 7.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 7.6 h·mg/L to about 11.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ ranging from about 10.5 h·mg/L to about 15.5 h·mg/L, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $AUC_{0\to\infty}$ of at least about 1.0 h·mg/L, at least 1.2 h·mg/L, at least 1.4 h·mg/L, at least 1.6 h·mg/L, at least 1.8 h·mg/L, at least 2.0 h·mg/L, at least 2.3 h·mg/L, at least 2.6 h·mg/L, at least 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.4 h·mg/L, at least 13.7 h·mg/L, at least 14 h·mg/L, at least 14.3 h·mg/L, at least 14.6 h·mg/L, at least 14.9 h·mg/L, at least 15.2 h·mg/L, or at least 15.5 h·mg/L.

In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 1.5 hours to about 10.5 hours including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 1.6 hours to about 2.5 hours, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 2.6 hours to about 5 hours, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 5.1 hours to about 7.5 hours, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 7.6 hours to about 8.5 hours, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ ranging from about 8.6 hours to about 10.6 hours, including all integers and fractions within the specified ranges. In another aspect, the composition is provided in a dosage form containing a total amount of about 360 mg to about 480 mg of a fumarate ester, wherein subjects administered the dosage form once daily exhibit a mean plasma monomethyl fumarate $T_{max}$ of at least 1.6 hours, at least 1.8 hours, at least 2 hours, at least 2.2 hours, at least 2.4 hours, at least 2.6 hours, at least 2.8 hours, at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, at least 6.6 hours, at least 6.8 hours, at least 7 hours, at least 7.2 hours, at least 7.4 hours, at least 7.6 hours, at least 7.8 hours, at least 8 hours, at least 8.2 hours, at least 8.4 hours, at least 8.6 hours, at least 8.8 hours, at least 9.0 hours, at least 9.2 hours, at least 9.4 hours, at least 9.6 hours, at least 9.8 hours, at least 10 hours, at least 10.2 hours, at least 10.4 hours, or at least 10.6 hours.

Another embodiment described herein is a pharmaceutical composition for treating, prophylaxis, or amelioration of general autoimmune or neurodegenerative disorders, comprising a fumarate ester, wherein the composition exhibits an in vitro dissolution rate (% dissolution per minute) at pH 6.8, as described herein in any one of Drawings 2-12.

Another embodiment described herein is a pharmaceutical composition for treating, prophylaxis, or amelioration of general autoimmune or neurodegenerative disorders, including but not limited to multiple sclerosis or psoriasis, comprising a fumarate ester, wherein the composition exhibits an in vitro dissolution rate comprising about 10% to about 80% dissolution after about 5 minutes to about 480 minutes at pH 6.8, including all integers and fractions within the specified ranges of dissolution and time. In another aspect, the in vitro dissolution rate at pH 6.8 is about 50% after about 20 minutes to about 1080 minutes, including all integers and fractions within the specified ranges of dissolution and time. In one aspect, the in vitro dissolution rate at pH 6.8 is about 50% after about 5 min, is about 50% after about 10 min, about 50% after about 20 min, about 50% after about 30 min, about 50% after about 40 min, about 50% after about 50 min, about 50% after about 60 min, about 50% after about 70 min, about 50% after about 80 min, about 50% after about 90 min, about 50% after about 120 min, about 50% after about 150 min, about 50% after about 180 min, about 50% after about 210 min, about 50% after about 240 min, about 50% after about 300 min, is about 50% after about 330 min, about 50% after about 360 min, is about 50% after about 390 min, about 50% after about 420 min, about 50% after about 480 min, about 50% after about 540 min, about 50% after about 600 min, about 50% after about 660 min, about 50% after about 720 min, about 50% after about 780 min, about 50% after about 840 min, about 50% after about 900 min, about 50% after about 960 min, or about 50% after 1080 min. In another aspect, the in vitro dissolution rate at pH 6.8 is about 50% after about 0.5 hour, about 50% after about 1 hour, about 50% after about 2 hours, about 50% after about 3 hours, about 50% after about 4 hours, about 50% after about 5 hours, about 50% after about 6 hours, about 50% after about 7 hours, about 50% after about 8 hours, about 50% after about 9 hours, about 50% after about 10 hours, about 50% after about 11 hours, about 50% after about 12 hours, about 50% after about 13 hours, about 50% after about 14 hours, about 50% after about 15 hours, about 50% after about 16 hours, about 50% after about 17 hours, or about 50% after about 18 hours. In one aspect, the in vitro dissolution rate at pH 6.8 is about 50% after about 10 minutes. In another aspect, the in vitro dissolution rate at pH 6.8 is about 50% after about 20 minutes. In another aspect, the in vitro dissolution rate at pH 6.8 is about 50% after about 45 minutes. In another aspect, the in vitro dissolution rate at pH 6.8 is about 50% after about 60 minutes. In one aspect, the in vitro dissolution rate at pH 6.8 is about 50% after about 120 minutes. In another aspect, the in vitro dissolution rate at pH 6.8 is about 50% after about 180 minutes. In another aspect, the in vitro dissolution rate at pH 6.8 is about 50% after about 240 minutes. In one aspect, the in vitro dissolution rate at pH 6.8 is about 50% after about 480 minutes.

Another embodiment described herein is a method of treating a neurological disease, neurodegenerative disease, or autoimmune disease comprising orally administering one or more doses of one or more fumarate esters described herein to a patient in need thereof, wherein the administration activates or modulates one or more cellular signaling pathways. In one aspect, the autoimmune disease comprises multiple sclerosis or psoriasis and the cellular signaling pathway comprises the nuclear erythroid-derived 2-like 2 (Nrf2) dependent antioxidant response element (ARE) pathway. Without being bound by any theory, it is believed that at least one aspect of the pharmacological activity of the fumarate esters described herein exert an anti-inflammatory and neuroprotective effect in patients with, for example, multiple sclerosis or psoriasis, by activating the Nrf2 cellular signaling pathway. Although not completely understood, the Nrf2 pathway is involved in the cellular response to oxidative stress, which has been linked to neuronal degeneration in multiple sclerosis and in other neurodegenerative or autoimmune diseases (e.g., HIV), see, e.g., Gao et al., *Clin. Pharmacol.* 6:19-34 (2014), which is incorporated by reference herein for its teachings thereof.

It is currently thought that under basal conditions, Nrf2 is sequestered in the cytoplasm to the actin-bound Kelch-like ECH-associated protein 1 (Keap1). Keap1 associates with the Cullin3 ubiquitin ligase adaptor protein, which positions Keap1 and its substrate in proximity (e.g., NRF2) to the E3 ubiquitin ligase Rbx1. Thus, under normal conditions, the substrate (Nrf2) is polyubiquitinated and targeted for degradation. In response to oxidative stress, Nrf2 is released from the Keap1/Nrf2 complex, preventing its degradation resulting in the concommitant translocation of NRF2 to the nucleus and activation of ARE-mediated gene transcription. Based on this understanding, any of the non-limiting methods for determining the activation of Nrf2 may be used that are further described herein. See U.S. Pat. No. 8,399,514, which is incorporated by reference herein for its teachings thereof.

Nrf2 activation may be determined by assessing the in vitro activation levels of Nrf2 and/or Nrf2 mRNA or protein expression levels. The sequence of the promoter region of the Nrf2 gene (−1065 to −35) is known. In vitro Nrf2 activation may be measured using a cell model system transfected or transduced with an expression construct containing the Nrf2 promoter element described above and an artificial reporter gene (e.g., luciferase or a fluorescent reporter gene (GFP, RFP, YFP etc.,). See, e.g., Chan et al., *Proc. Natl. Aacd. Sci. USA* 93:13943-13948 (1996) and Kwak et al., *Mol. Cell. Biol.* 22(9):2883-2892 (2002), each of which is incorporated by reference herein for their teachings thereof. Nrf2 activation may be assessed by measuring reporter gene expression in treated vs. non-treated cells using standard imaging or fluorescence quantification techniques. Alternatively, PCR (e.g., qRT-PCR) or Northern blotting may be used to determine expression levels of Nrf2 mRNA, or Western blotting to determine Nrf2 protein levels. See, e.g., Kwak et al., *Mol. Cell. Biol.* 22(9):2883-2892 (2002) and Kwak et al., *Mol. Med.* 7:135-145 (2001), each of which is incorporated by reference herein for their teachings thereof. Antibodies against Nrf2 are can be produced by methods known in the art and are commercially available from, for example, StressGen.

In addition, Nrf2 activation may be assessed by determining the subcellular localization and/or nuclear translocation of Nrf2 in treated vs. non-treated cells. Such assays include cell staining, or analysis of cytoplasmic versus nuclear cell extracts. For example, an Nrf2-green fluorescence protein (GFP) fusion protein construct can be introduced into cells and visualized as described in, e.g., Kraft et al., *J. Neurosci.* 24:1101-1112 (2004) and in Satoh et al., *Proc. Natl. Aacd. Sci.* USA 103(3):768-773 (2006).

Nrf2 activation may be determined through indirect measurement of the expression levels and/or activity of one or more genes under the control of Nrf2 in treated vs. non-treated cells. For example, the expression levels of NADPH dehydrogenase quinone 1 (NQO1) may be determined using, for example, qRT-PCR, Northern blotting, or Western blotting, see, e.g., Wierinckx et al., *J. Neuroimmunology.* 166:132-143 (2005). Methods for measuring enzymatic activity of NQO1, using menadione as a substrate, are described in Dinkova-Kostova et al., *Proc. Natl. Aacd. Sci. USA* 98:3404-09 (2001).

The cell type being contacted with the one or more fumarate esters described herein may comprise a neuron or a neuronal cell line, a colon carcinoma cell line (e.g., DLD1), a neuroblastoma cell line (e.g., SkNSH or IMR32), or a primary immune cell (e.g., a monocyte or T-lymphocyte or B-lymphocyte). The cell may be a cell in culture (in vitro) or be inside of a mammal (in vivo). Alternatively, endogenous Nrf2 activation may be determined by measuring the levels of Nrf2 or a Nrf2 regulated gene (e.g., NQO1) in a primary cell or cell population (e.g., a monocyte, T-lymphocyte, or neuronal cell) taken from a human patient having neurological disease, neurodegenerative disease, or autoimmune disease (e.g., multiple sclerosis or psoriasis).

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

DMF Enteric Soft Capsule Fills

Based on results of dimethyl fumarate (DMF) solubility testing in various lipid or lipophilic vehicles (data not shown), two formulations were selected for further studies and encapsulated in enteric soft gelatin capsules: one having polyethylene glycol and one with medium chain mono- and diglycerides. Organic acids such as caprylic acid, lactic acid, or oleic acid, were incorporated into the matrix fill to prevent the hydrolysis of dimethyl fumarate and to retain enteric properties of the shell. Application batches of enteric soft capsules were prepared by rotary die encapsulation using the fill compositions shown in Table 5.

TABLE 5

DMF Fill Compositions

| Ingredient | Capmul ® MCM Matrix (A413-A) | | PEG Matrix (A413-B) | |
|---|---|---|---|---|
| | mg/capsule | % wt | mg/capsule | % wt |
| Dimethyl Fumarate (Mean PSD: 80 μm) | 240 | 32.0 | 240 | 32.0 |
| Capmul ® MCM | 367.5 | 49.0 | — | — |
| PEG 400 | — | — | 382.5 | 51.0 |
| Povidone K30 | 52.5 | 7.0 | 37.5 | 5.0 |
| Tween ® 80 | 75 | 10.0 | 75 | 10.0 |
| Lactic acid | 15 | 2.0 | 15 | 2.0 |
| TOTAL | 750 | 100% | 750 | 100% |

Figure 2:
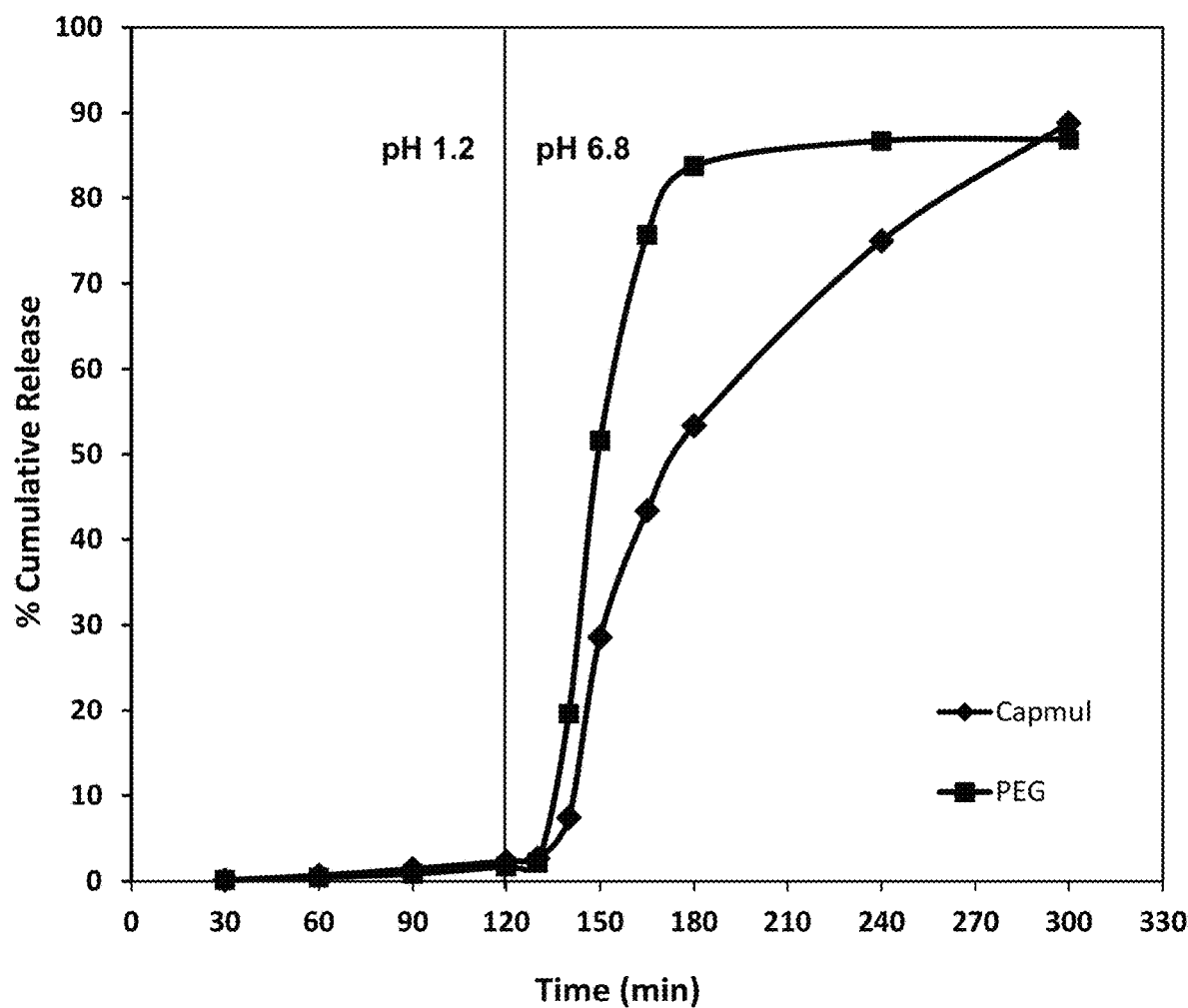
FIG. 2. Dissolution of enteric soft capsules comprising two DMF formulations.

The enteric soft capsules comprising the matrix formulations shown in Table 5 were subject to two-stage dissolution experiments in a USP Apparatus II (e.g., paddle method at 100 rpm). For these experiments, the capsules were introduced in to simulated gastric fluid, 0.1 NHC1, pH 1.2, for 2 hours. After 2 hours, the capsules were transferred to simulated intestinal fluid, phosphate buffer, pH 6.8. The results are shown in FIG. 2. The results show that the capsules retain their enteric properties for at least 2 hours in simulated gastric fluid at pH 1.2. Both types of capsules released DMF shortly (~10 minutes) after being transferred to simulated intestinal fluid, pH 6.8. The enteric soft capsules comprising matrices comprising PEG 400 released DMF more rapidly than those comprising Capmul® MCM (ABITEC Corp.; medium chain mono- and di-glycerides).

Example 2

Stability of the Enteric Soft Capsules Over Time

Figure 3:
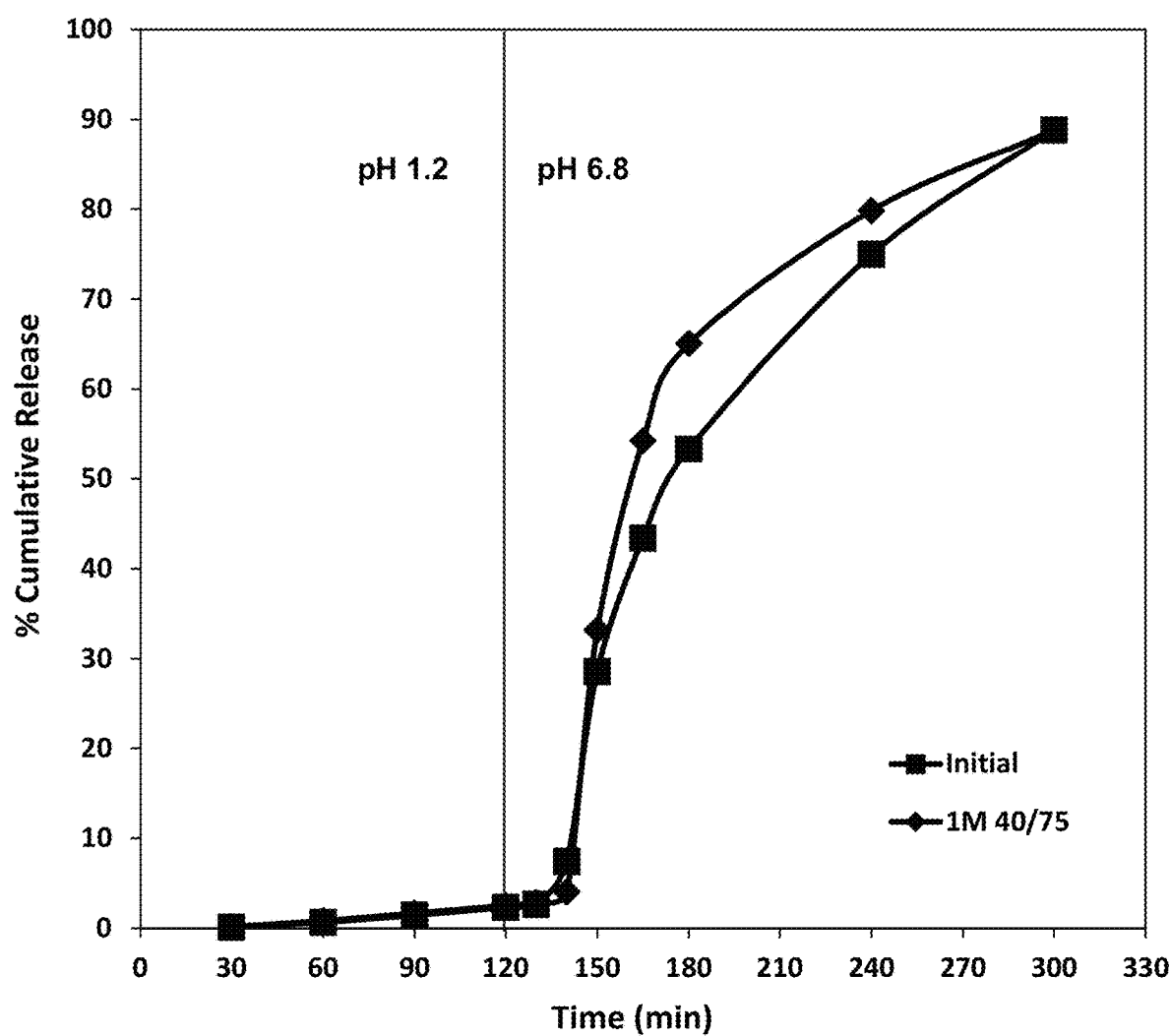
FIG. 3. DMF enteric soft capsule stability.

The temporal stability of the dimethyl fumarate enteric soft capsule fill formulation shown in Table 6 was assessed. A sample of DMF enteric soft capsules was subjected to accelerated aging by a 1 month of exposure to 40° C. and 75% relative humidity conditions and then evaluated in two-stage dissolution experiment. A second sample of DMF enteric soft capsules was subject to two-stage dissolution shortly after manufacturing. Both sets of enteric capsules remained intact in the acidic conditions for at least 2 hours. FIG. 3. The freshly manufactured capsules released DMF slightly faster than the age-accelerated capsules when the pH was shifted to 6.8 (phosphate buffer).

TABLE 6

DMF Fill Composition

| Ingredient | mg/capsule | % weight |
|---|---|---|
| Dimethyl fumarate (Mean PSD: 80 μm) | 240 | 32.0 |
| Capmul ® MCM | 367.5 | 49.0 |
| Povidone K 30 | 52.5 | 7.0 |
| Tween ® 80 | 75 | 10.0 |
| Lactic acid | 15 | 2.0 |
| TOTAL | 750 mg | 100% |

Example 3

DMF Release in Enteric Soft Capsules

Figure 4:
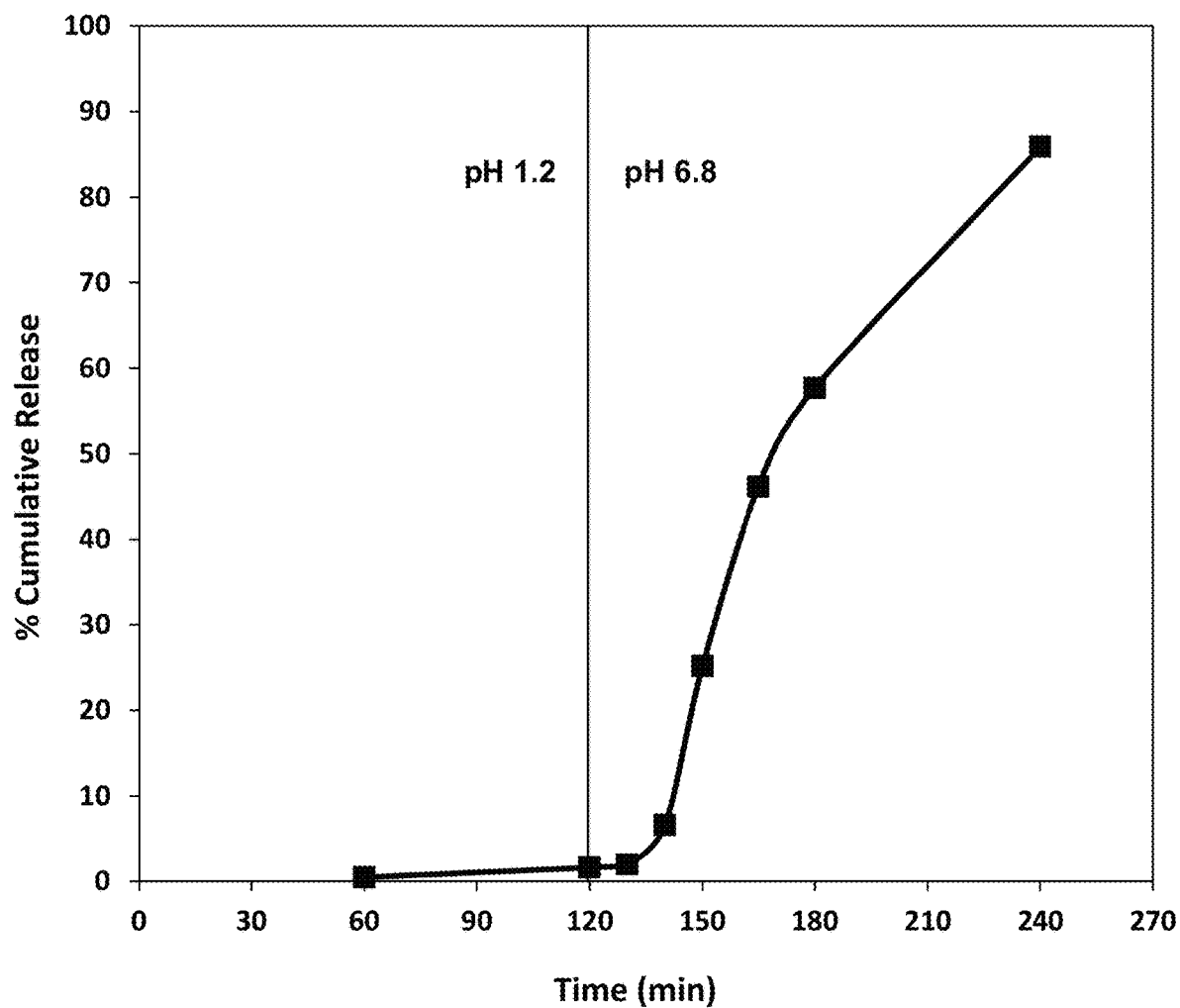
FIG. 4. DMF release in enteric soft capsules.

A developmental batch of enteric soft capsules comprising a Capmul® MCM matrix containing particles of dimethyl fumarate (Table 6) was subject to two-stage dissolution at pH 1.2 in simulated gastric fluid for 2 hours, then the buffer was changed to phosphate buffer, pH 6.8, containing 2% Cremophor® RH 40. FIG. 4. The enteric capsules remained intact in the acidic condition, and then began releasing DMF within 20 minutes of the pH-shift to simulated intestinal fluid.

Example 4

Surfactants Affect DMF Release Rate

Figure 5:
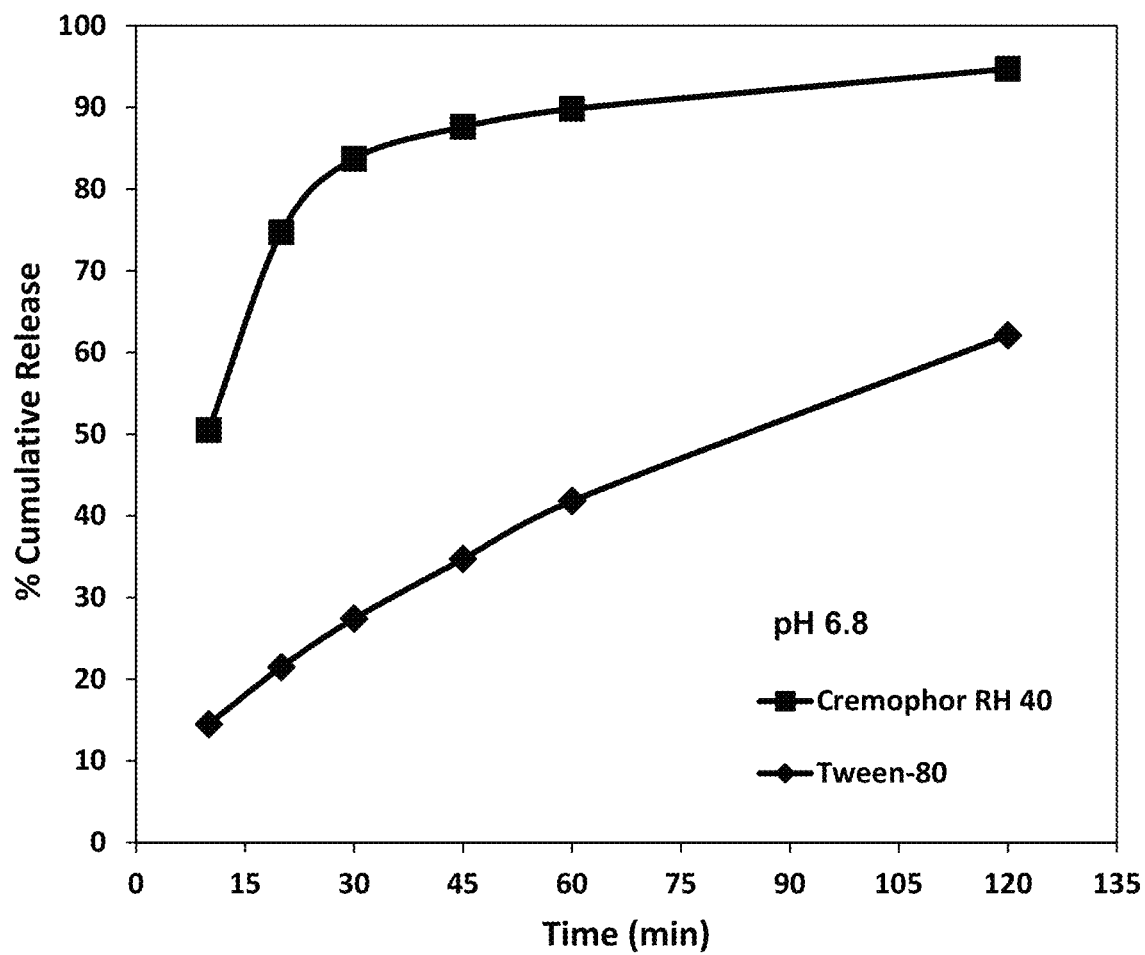
FIG. 5. Surfactant affects DMF release rate.

Enteric soft capsules were prepared with matrices comprising 10% Tween® 80 (Uniqema, ICI Americas Inc; polyoxyethylene (80) sorbitan monooleate; e.g., polysorbate 80) or 10% Cremophor® RH 40 (BASF SE; polyoxyl 40 hydrogenated castor oil) (Table 7) and then tested in dissolution experiments at pH 6.8. FIG. 5. The enteric soft capsules with fills containing Cremophor® released DMF much more rapidly than those containing Tween® 80.

TABLE 7

| | DMF Fill Compositions | | | |
|---|---|---|---|---|
| | Tween ® 80 Matrix | | Cremophor ® RH 40 Matrix | |
| Ingredient | mg/capsule | % wt | mg/capsule | % wt |
| Dimethyl Fumarate (Mean PSD: 80 μm) | 240 | 32.0 | 240 | 32.0 |
| Capmul ® MCM | 367.5 | 49.0 | 367.5 | 49.0 |
| Povidone K 30 | 52.5 | 7.0 | 52.5 | 7.0 |
| Tween ® 80 | 75 | 10.0 | — | — |
| Cremophor ® RH 40 | — | — | 75 | 10.0 |
| Lactic acid | 15 | 2.0 | 15 | 2.0 |
| TOTAL | 750 | 100% | 750 | 100% |

Example 5

Polyvinylpyrrolidone Concentration Affects DMF Release Rate

Figure 6:
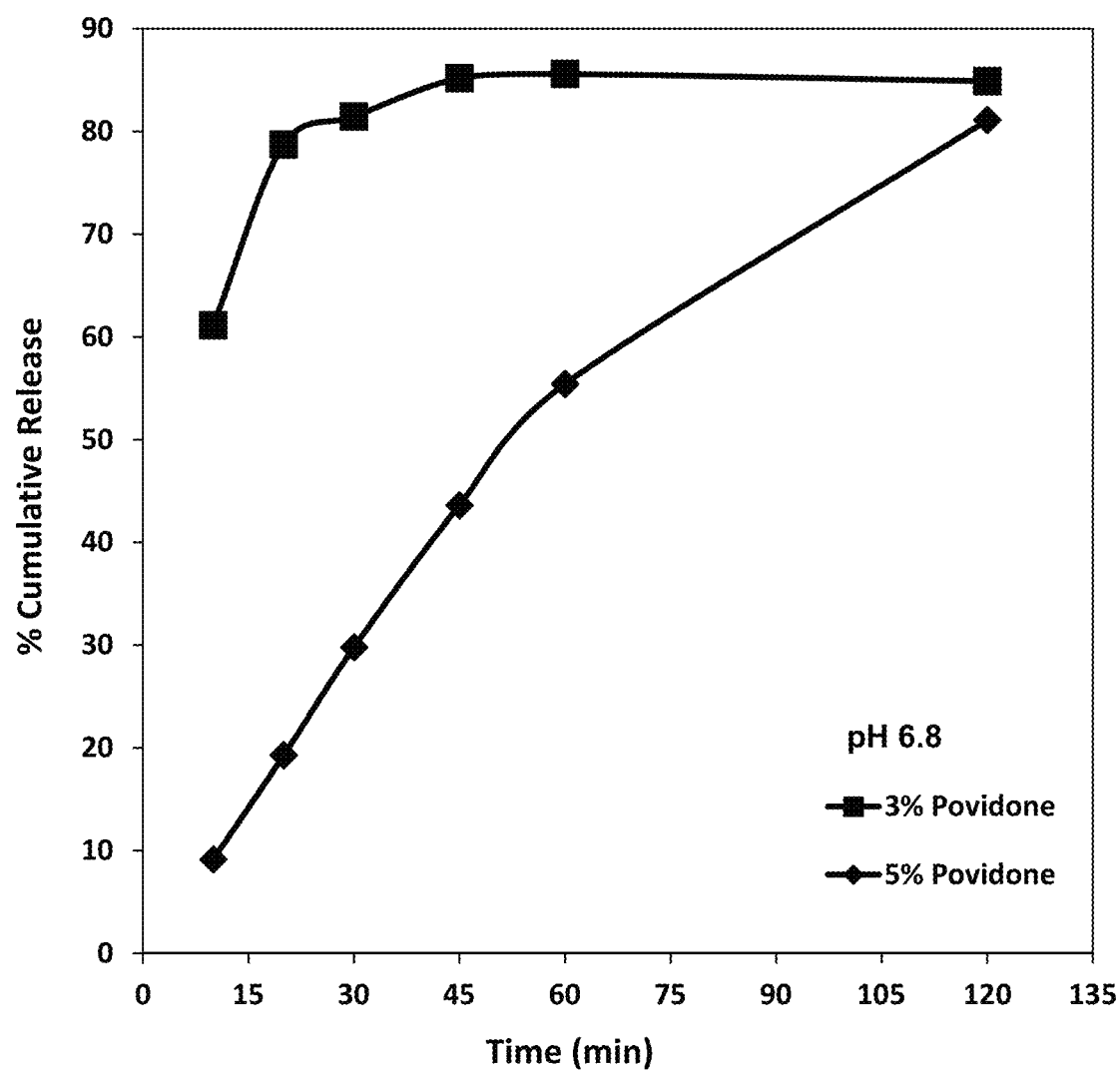
FIG. 6. Polyvinylpyrrolidone concentration affects DMF release rate.

Enteric soft capsules prepared containing fills with of 3% or 5% concentrations of Povidone K30 (e.g., PVP; 30,000 average MW) (Table 8) were tested in dissolution experiments at pH 6.8. FIG. 6. The enteric soft capsules with matrices containing 5% Povidone K30 released DMF more rapidly at pH 6.8 than those with fills containing 3% Povidone K30.

TABLE 8

| | DMF Fill Compositions | | | |
|---|---|---|---|---|
| | 3% PVP | | 5% PVP | |
| Ingredient | mg/capsule | % wt | mg/capsule | % wt |
| Dimethyl Fumarate (Mean PSD: 80 μm) | 240 | 32.0 | 240 | 32.0 |
| Capmul ® MCM | 397.5 | 53 | 382.5 | 51 |
| Cremophor ® RH 40 | 75 | 10.0 | 75 | 10.0 |
| Povidone K 30 | 22.5 | 3.0 | 37.5 | 5.0 |
| Lactic acid | 15 | 2.0 | 15 | 2.0 |
| TOTAL | 750 | 100% | 750 | 100% |
| Viscosity: | 43191 Cp | | 122000 Cp | |

Based on the foregoing formulation studies, the Capmul® MCM-based formulation was selected for further analysis. A batch was manufactured using the formulation below (Table 9).

TABLE 9

| DMF Fill Composition | | |
|---|---|---|
| Ingredient | mg/capsule | % weight |
| Dimethyl Fumarate (Mean PSD: 80 μm) | 240 | 32 |
| Capmul ® MCM | 375 | 50 |
| Cremophor ® RH 40 | 75 | 10 |
| Povidone K 30 | 52.5 | 7 |
| Lactic acid | 15 | 2 |
| TOTAL | 750 mg | 100% |

Example 6

DMF Enteric Soft Capsules are Amenable to Controlled or Extended Release

Figure 7:
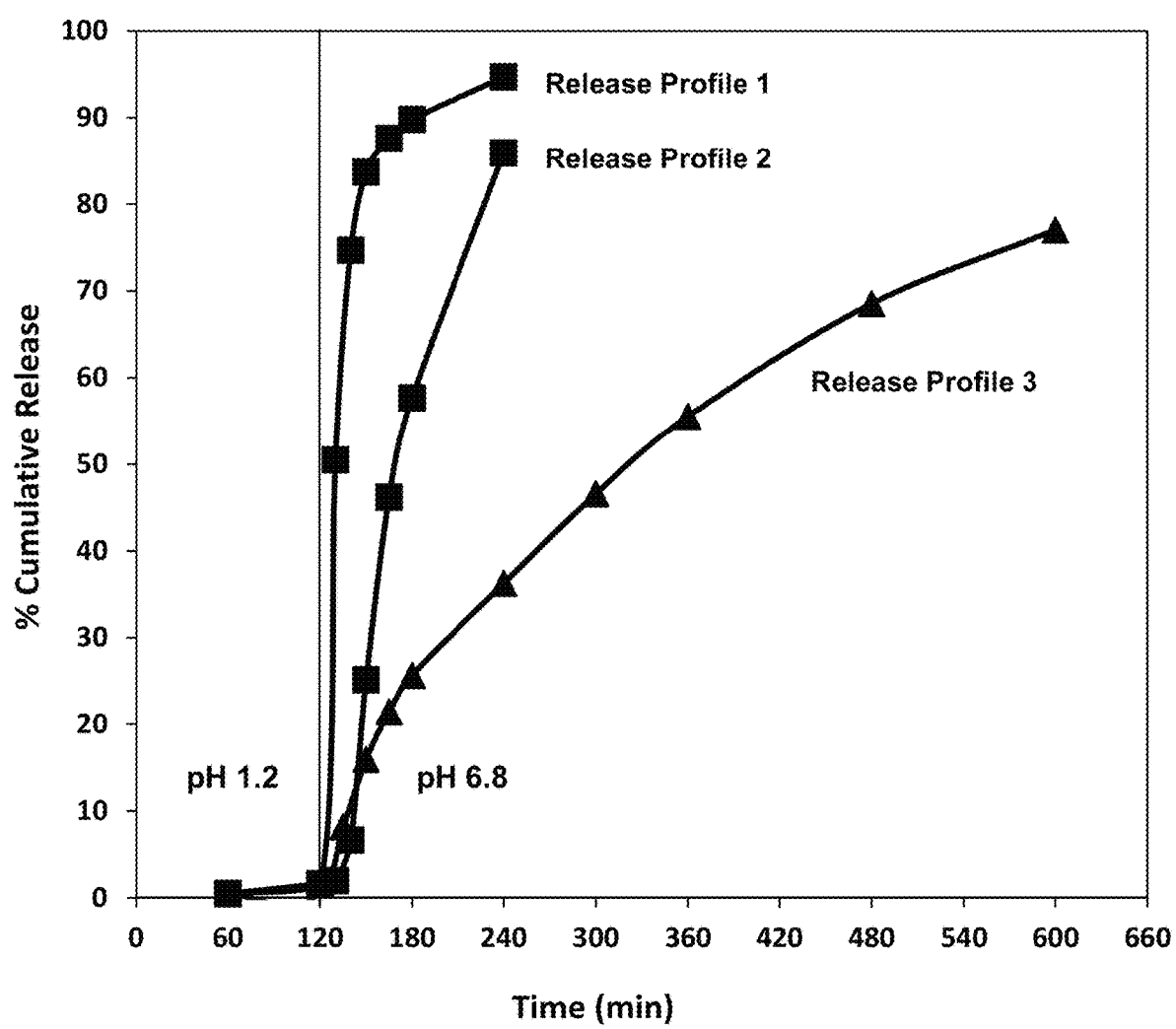
FIG. 7. DMF enteric soft capsules are amenable to controlled or extended release.

The release profile of DMF is modified by varying the enteric soft capsule shell composition or by altering the fill composition or particle size of the active ingredient. Three different release profiles were observed under two-stage dissolution experiments. All enteric soft capsules were resistant to acid for at least 2 hours, and begin releasing DMF upon transition to pH 6.8. FIG. 7. A release profile was observed in an enteric soft capsule comprising a matrix of Capmul® MCM and Cremophor® RH 40 (Table 10; Release Profile 1). A different release profile was observed with an enteric soft capsule shell comprising a Capmul® MCM and Tween® 80 matrix (Table 6; Release Profile 2). Another release profile was observed with an enteric soft capsule shell comprising a matrix of soybean oil, Tween® 80, and solid particles of DMF having a mean particle distribution size of 148 μm (Table 11; Release Profile 3).

TABLE 10

| DMF Fill Composition (P31) | | |
|---|---|---|
| Ingredient | mg/capsule | % weight |
| Dimethyl fumarate (Mean PSD: 80 μm) | 240 | 32.0 |
| Capmul ® MCM | 367.5 | 49.0 |
| Cremophor ® RH 40 | 75 | 10.0 |
| Povidone K 30 | 52.5 | 7.0 |
| Lactic acid | 15 | 2.0 |
| TOTAL | 750 mg | 100% |

TABLE 11

| DMF Fill Composition (P6) | | |
|---|---|---|
| Ingredient | mg/capsule | % weight |
| Dimethyl fumarate (Mean PSD 148 μm) | 240 | 43.6 |
| Soybean oil | 285.25 | 51.9 |
| Aerosil 200 | 75 | 10.0 |
| Tween ® 80 | 11 | 2.0 |
| Caprylic acid | 11 | 2.0 |
| TOTAL | 550 mg | 100% |

Example 7

DMF Particle Size Affects Release Rate

Figure 8:
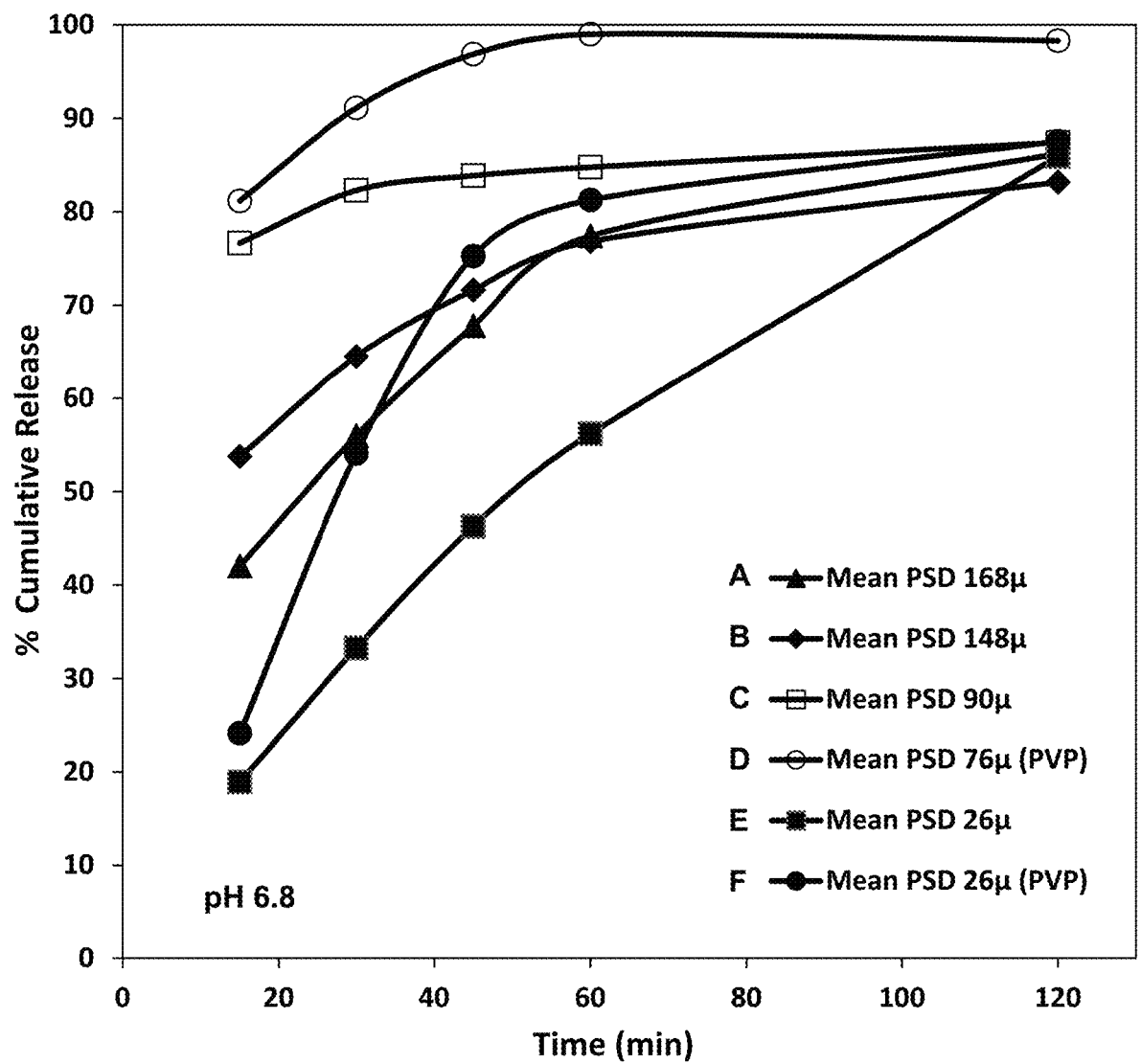
FIG. 8. DMF particle size affects release rate.

Enteric soft capsules comprising matrices with DMF particles of differing mean particle size distributions as shown in Table 12 were subject to dissolution at pH 6.8. FIG. 8.

TABLE 12

Matrices with Varying DMF Particle Sizes

| | Formulation | | | | | |
|---|---|---|---|---|---|---|
| | A (P7) | | B (P8) | | C (P9) | |
| Ingredient | mg/capsule | % weight | mg/capsule | % weight | mg/capsule | % weight |
| DMF Mean PSD: 168 μm | 240 | 43.6 | — | — | — | — |
| DMF Mean PSD: 148 μm | — | — | 240 | 43.6 | — | — |
| DMF Mean PSD: 90 μm | — | — | — | — | 240 | 43.6 |
| PEG 400 | 244 | 44.4 | 244 | 44.4 | 244 | 44.4 |
| Povidone K30 | — | — | — | — | — | — |
| Tween ® 80 | 55 | 10 | 55 | 10 | 55 | 10 |
| Caprylic acid | 11 | 2 | 11 | 2 | 11 | 2 |
| Lactic acid | — | — | — | — | — | — |
| TOTAL | 550 | 100 | 550 | 100 | 550 | 100 |

| | Formulation | | | | | |
|---|---|---|---|---|---|---|
| | D (P25) | | E (P15) | | F (P23) | |
| Ingredient | mg/capsule | % weight | mg/capsule | % weight | mg/capsule | % weight |
| DMF Mean PSD: 76 μm | 240 | 34.3 | — | — | — | — |
| DMF Mean PSD: 26 μm | — | — | 240 | 28.2 | 240 | 28.2 |
| PEG 400 | 355 | 50.7 | 508 | 59.8 | 482 | 56.8 |
| Povidone K30 | 21 | 3 | — | — | 26 | 3 |
| Tween ® 80 | 70 | 10 | 85 | 10 | 85 | 10 |
| Caprylic acid | — | — | 17 | 2 | 17 | 2 |
| Lactic acid | 14 | 2 | — | — | — | — |
| TOTAL | 700 | 100 | 850 | 100 | 850 | 100 |

Example 8

Enteric soft capsules comprising various matrices comprising DMF particles having particle size distribution of d90≤90 μm were prepared and analyzed in two stage (pH 1.2 and pH 6.8) or single stage (pH 6.8) dissolution experiments (data not shown). (Tables 13-15).

TABLE 13

Various DMF Fill Compositions

| | Formulation | | | | | |
|---|---|---|---|---|---|---|
| | A (P32) | | B (P33) | | C (P34) | |
| Ingredient | mg/capsule | % weight | mg/capsule | % weight | mg/capsule | % weight |
| DMF PSD: d90 ≤ 90 μm | 240 | 32.0 | 240 | 32.0 | 240 | 32.0 |
| Capmul ® MCM | 360 | 48.0 | 322.5 | 43.0 | 352.5 | 47.0 |
| Cremophor ® RH 40 | 112.5 | 15.0 | 150 | 20.0 | 112.5 | 15.0 |
| Lactic acid | 37.5 | 5.0 | 37.5 | 5.0 | 37.5 | 5.0 |
| TOTAL | 750 | 100 | 750 | 100 | 750 | 100 |

| | D (P35) | | E (P37) | | F (P38) | |
|---|---|---|---|---|---|---|
| Ingredient | mg/capsule | % weight | mg/capsule | % weight | mg/capsule | % weight |
| DMF PSD: d90 ≤ 90 μm | 240 | 32.0 | 240 | 32.0 | 240 | 32.0 |
| Capmul ® MCM | 315 | 42.0 | 360 | 48.0 | 360 | 48.0 |
| Cremophor ® RH 40 | 150 | 20.0 | 75 | 10.0 | 75 | 10.0 |
| Lactic acid | 37.5 | 5.0 | 37.5 | 5.0 | 37.5 | 5.0 |

TABLE 13-continued

Various DMF Fill Compositions

Formulation

| | | | | | | |
|---|---|---|---|---|---|---|
| Povidone K 30 | 7.5 | 1.0 | — | — | — | — |
| PEG 400 | — | — | 37.5 | 5.0 | — | — |
| Polypropylene glycol | — | — | — | — | 37.5 | 5.0 |
| TOTAL | 750 | 100 | 750 | 100 | 750 | 100 |

| | G (P39) | | H (P41) | | I (P43) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 482.5 | 56.8 | 397.5 | 46.8 | 397.5 | 46.8 |
| Cremophor ® RH 40 | 85 | 10.0 | 85 | 10.0 | — | — |
| Lactic acid | 42.5 | 5.0 | 42.5 | 5.0 | 42.5 | 5.0 |
| Labrasol ® | — | — | 85 | 10.0 | 170 | 20.0 |
| TOTAL | 850 | 100 | 850 | 100 | 850 | 100 |

TABLE 14

Various DMF Fill Compositions

Formulation

| | A (P44) | | B (P45) | | C (P46) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 372 | 43.8 | 355 | 41.8 | 329.5 | 38.8 |
| Cremophor ® RH 40 | 85 | 10.0 | 85 | 10.0 | 85 | 10.0 |
| Lactic acid | 42.5 | 5.0 | 42.5 | 5.0 | 42.5 | 5.0 |
| Labrasol ® | 85 | 10.0 | 85 | 10.0 | 85 | 10.0 |
| Povidone K 30 | 25.5 | 3.0 | — | — | 25.5 | 3.0 |
| Mannitol | — | — | 42.5 | 5.0 | 42.5 | 5.0 |
| TOTAL | 850 | 100 | 850 | 100 | 850 | 100 |

| | D (P47) | | E (P48) | | F (P49) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 384.75 | 45.3 | 284.195 | 33.43 | 312.5 | 36.76 |
| Cremophor ® RH 40 | 85 | 10.0 | 85 | 10.0 | 85 | 10.0 |
| Lactic acid | 42.5 | 5.0 | 42.5 | 5.0 | 42.5 | 5.0 |
| Povidone K 30 | 12.75 | 1.5 | — | — | — | — |
| Labrasol ® | — | — | 85 | 10.0 | 85 | 10.0 |
| PEG 3350 | 85 | 10.0 | 113.305 | 13.33 | 85 | 10.00 |
| TOTAL | 850 | 100 | 850 | 100 | 850 | 100 |

| | G (P50) | | H (P51) | | I (P52) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 333.75 | 39.26 | 287 | 33.76 | 333.75 | 39.26 |
| Cremophor ® RH 40 | 85 | 10.0 | 85 | 10.00 | 85 | 10.00 |
| Lactic acid | 42.5 | 5.0 | 42.5 | 5.0 | 42.5 | 5.0 |
| Labrasol ® | 85 | 10.0 | 85 | 10.0 | 85 | 10.00 |
| PEG 3350 | 63.75 | 7.50 | — | — | — | — |
| Povidone K 17 | — | — | 25.5 | 3.00 | — | — |
| Mannitol | — | — | 85 | 10.00 | — | — |
| Crospovidone-CL | — | — | — | — | 63.75 | 7.50 |
| TOTAL | 850 | 100 | 850 | 100 | 850 | 100 |

TABLE 15

Various DMF Fill Compositions

| | A (P53) | | B (P54) | | C (P55) | |
|---|---|---|---|---|---|---|
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 397.5 | 46.76 | 397.5 | 46.76 | 390.7 | 45.96 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| PEG 3350 | 85 | 10.00 | — | — | — | — |
| PEG 400 | — | — | — | — | 42.5 | 5.00 |
| Lutrol ® F 68 | — | — | 85 | 10.00 | — | — |
| Sodium lauryl sulfate | — | — | — | — | 49.3 | 5.80 |
| TOTAL | 850 | 100 | 850 | 100 | 850 | 100 |

| | D (P56) | | E (P57) | | F (P58) | |
|---|---|---|---|---|---|---|
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 355 | 41.76 | 363.5 | 42.76 | 355 | 41.76 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| PEG 400 | 85 | 10.00 | 85 | 10.00 | 85 | 10.00 |
| Crospovidone CL | 42.5 | 5.00 | — | — | — | — |
| Crospovidone CL-F | — | — | 34 | 4.00 | — | — |
| Crospovidone CL-M | — | — | — | — | 42.5 | 5.00 |
| TOTAL | 850 | 100 | 850 | 100 | 850 | 100 |

| | G (P59) | | H (P60) | | I (P61) | |
|---|---|---|---|---|---|---|
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 312.5 | 36.76 | 355 | 41.76 | 329.5 | 38.76 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| Labrasol ® | 85 | 10.00 | 85 | 10.00 | 85 | 10.00 |
| Pearlitol ® Flash | 85 | 10.00 | — | — | 42.5 | 5.00 |
| Croscarmellose Sodium | — | — | 42.5 | 5.00 | 25.5 | 3.00 |
| TOTAL | 850 | 100 | 850 | 100 | 850 | 100 |

Example 9

Capsule Shell Thickness Affects Release Rate

Figure 9:
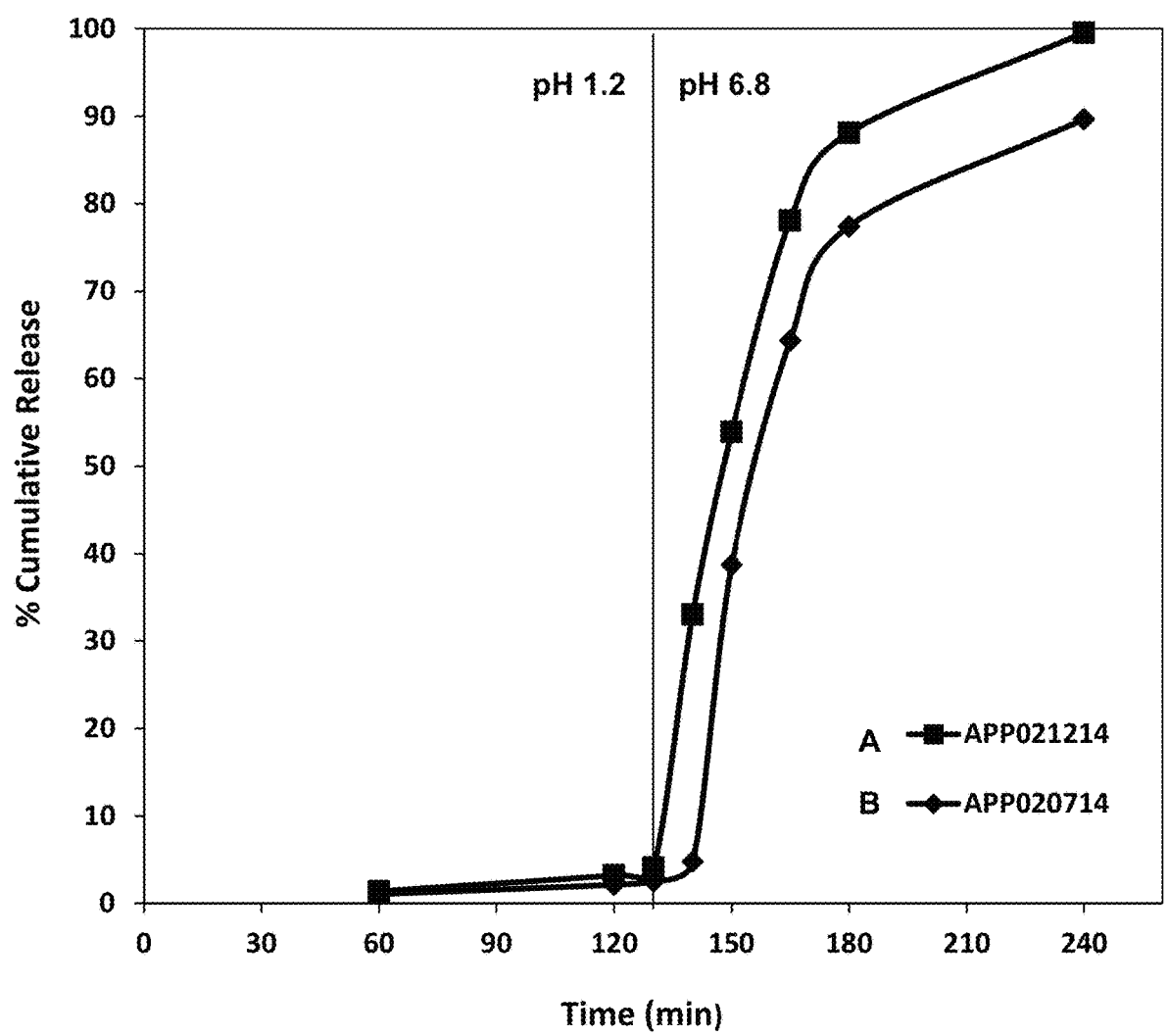
FIG. 9. Two-stage dissolution of application batches.

Application batches of enteric soft capsules with shell thicknesses of 0.028 inches or 0.033 inches were prepared comprising DMF particles having particle size distributions of d90≤90 μm in various matrices (Table 16) and analyzed in two stage (pH 1.2 and pH 6.8) dissolution experiments (FIG. 9).

TABLE 16

DMF Fill Compositions

| | A (APP021214) (0.028 inch ribbon) | | B (APP020714) (0.033 inch ribbon) | |
|---|---|---|---|---|
| Ingredient | mg/capsule | % wt | mg/capsule | % wt |
| Dimethyl Fumarate PSD: d90 ≤ 90 μm | 240 | 28.2 | 240 | 28.2 |
| Capmul ® MCM | 440 | 51.8 | 465.5 | 54.8 |
| Cremophor ® RH 40 | 85 | 10.0 | 85 | 10.0 |
| Povidone K30 | 42.5 | 5.0 | 42.5 | 5.0 |
| PEG 400 | — | — | 42.5 | 5.0 |
| Crospovidone-CL | 17 | 2.0 | — | — |
| TOTAL | 850 | 100% | 850 | 100% |

| | C (APP022414-A) (0.028 inch ribbon) | | D (APP022414-B) (0.028 inch ribbon) | |
|---|---|---|---|---|
| Ingredient | mg/capsule | % wt | mg/capsule | % wt |
| Dimethyl Fumarate PSD: d90 ≤ 90 μm | 240 | 28.24 | 240 | 28.24 |
| Capmul ® MCM | 312.5 | 36.76 | 312.5 | 36.76 |
| Cremophor ® RH 40 | 85 | 10.0 | 85 | 10.0 |
| Povidone K30 | 42.5 | 5.0 | 42.5 | 5.0 |
| PEG 600 | 127.5 | 15.0 | — | — |

TABLE 16-continued

| DMF Fill Compositions | | | | |
|---|---|---|---|---|
| Crospovidone-CL | 42.5 | 5.0 | — | — |
| Labrasol ® | — | — | 85 | 10.0 |
| Pearlitol ® Flash | — | — | 85 | 10.0 |
| TOTAL | 850 | 100% | 850 | 100% |

Example 10

Figure 10:
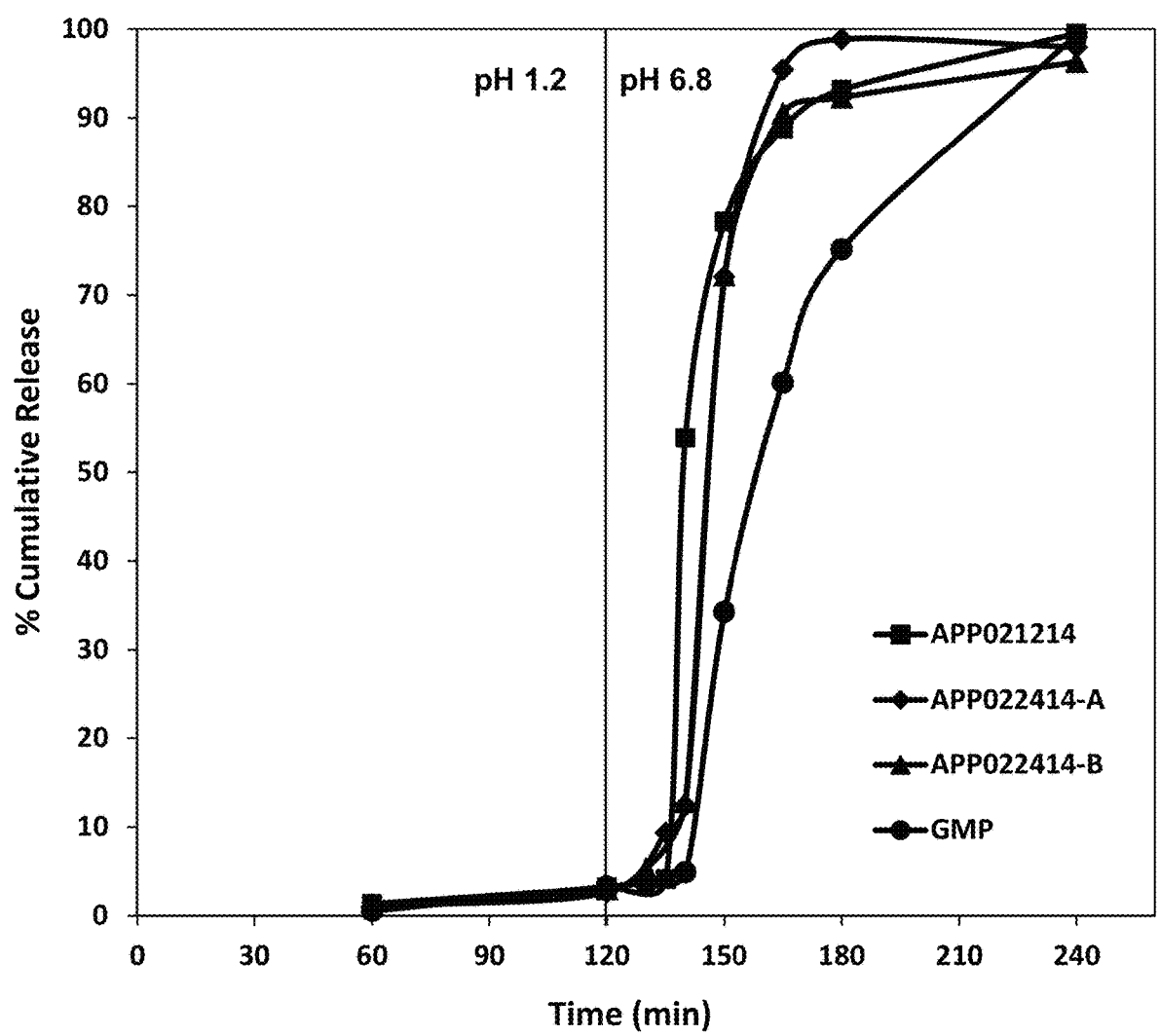
FIG. 10. Two-stage dissolution of GMP batch compared to application batches.

A GMP batch of enteric soft capsules (0.038-inch shell thickness) comprising DMF particles having a particle size distribution of PSD: d90≤90 µm was prepared with the matrix composition shown in Table 17 and analyzed in two stage (pH 1.2 and pH 6.8) dissolution experiments (FIG. 10) and compared to application batches (Table 15).

TABLE 17

| GMP DMF Fill Composition | | |
|---|---|---|
| Ingredient | mg/capsule | % weight |
| Dimethyl fumarate PSD: d90 ≤ 90 µm | 240 | 32.0 |
| Capmul ® MCM | 375 | 50.0 |
| Cremophor ® RH 40 | 75 | 10.0 |
| Povidone K 30 | 22.5 | 3.0 |
| Lactic acid | 37.5 | 5.0 |
| TOTAL | 750 mg | 100% |

Example 11

Povidone K30 and PEG 600 Affect DMF Release Rate

Figure 11:
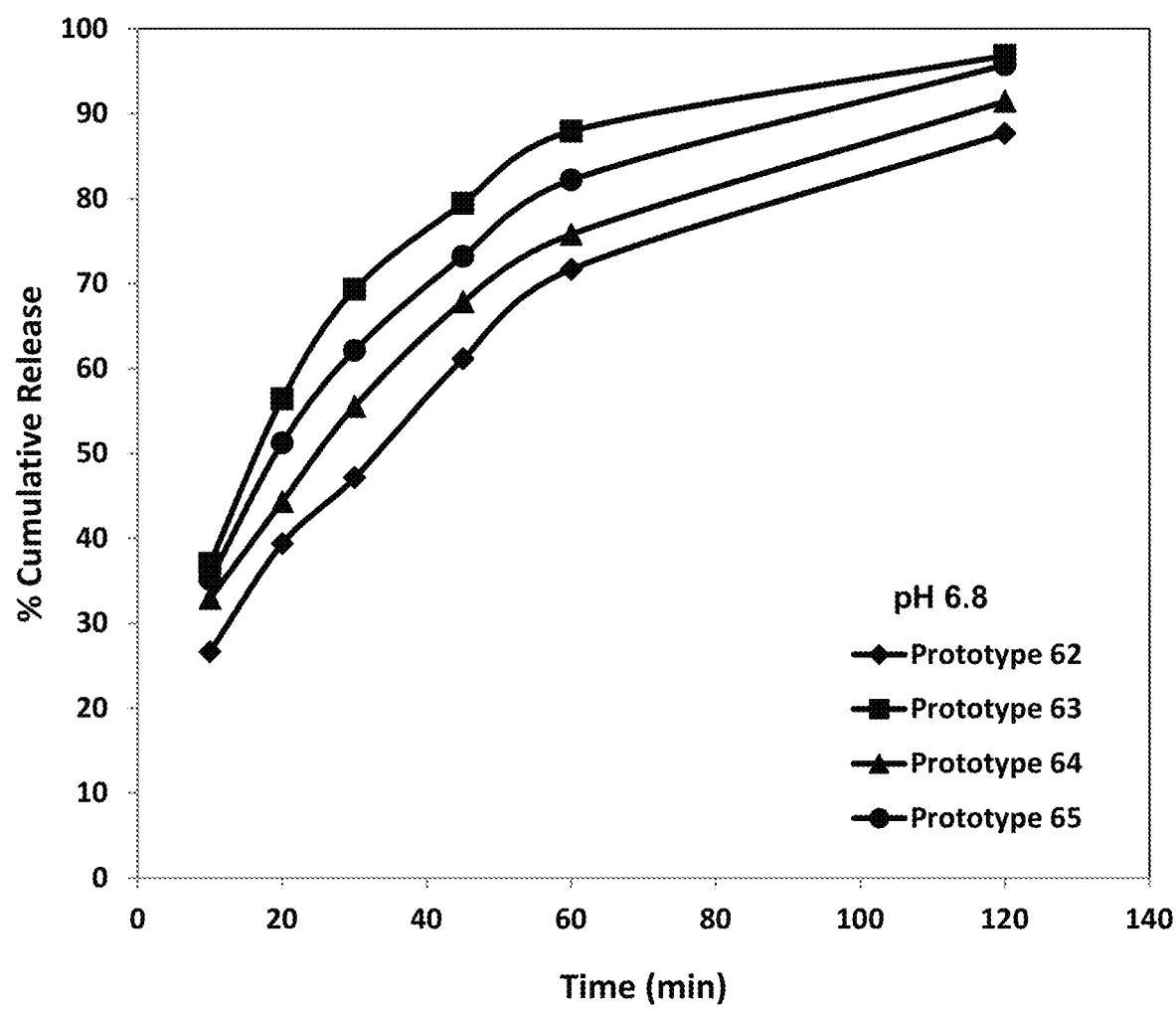
FIG. 11. Effects of Povidone K30 and PEG 600 on DMF release rate.

DMF matrices were prepared with and without Povidone K30 or PEG 600 (Table 18) and analyzed in single stage (pH 6.8) dissolution experiments (FIG. 11).

TABLE 18

| DMF Fill Compositions | | | | |
|---|---|---|---|---|
| | A (P62) | | B (P63) | |
| Ingredient | mg/capsule | % weight | mg/capsule | % weight |
| Dimethyl fumarate PSD: d90 ≤ 90 µm | 240 | 28.2 | 240 | 28.24 |
| Capmul ® MCM | 482.5 | 56.8 | 384.75 | 45.26 |
| Cremophor ® RH 40 | 85 | 10.0 | 85 | 10.00 |
| Povidone K 30 | — | — | 12.75 | 1.50 |
| PEG 600 | — | — | 85 | 10.00 |
| Lactic acid | 42.5 | 5.0 | 42.5 | 5.0 |
| TOTAL | 850 mg | 100% | 850 mg | 100% |

| | C (P64) | | D (P65) | |
|---|---|---|---|---|
| Ingredient | mg/capsule | % weight | mg/capsule | % weight |
| Dimethyl fumarate PSD: d90 ≤ 90 µm | 240 | 28.24 | 240 | 28.24 |
| Capmul ® MCM | 457 | 53.76 | 372 | 43.76 |
| Cremophor ® RH 40 | 85 | 10.00 | 85 | 10.00 |
| Povidone K 30 | 25.5 | 3.00 | 25.5 | 3.00 |
| PEG 600 | — | — | 85 | 10.00 |
| Lactic acid | 42.5 | 5.00 | 42.5 | 5.00 |
| TOTAL | 850 mg | 100% | 850 mg | 100% |

Example 12

Figure 12:
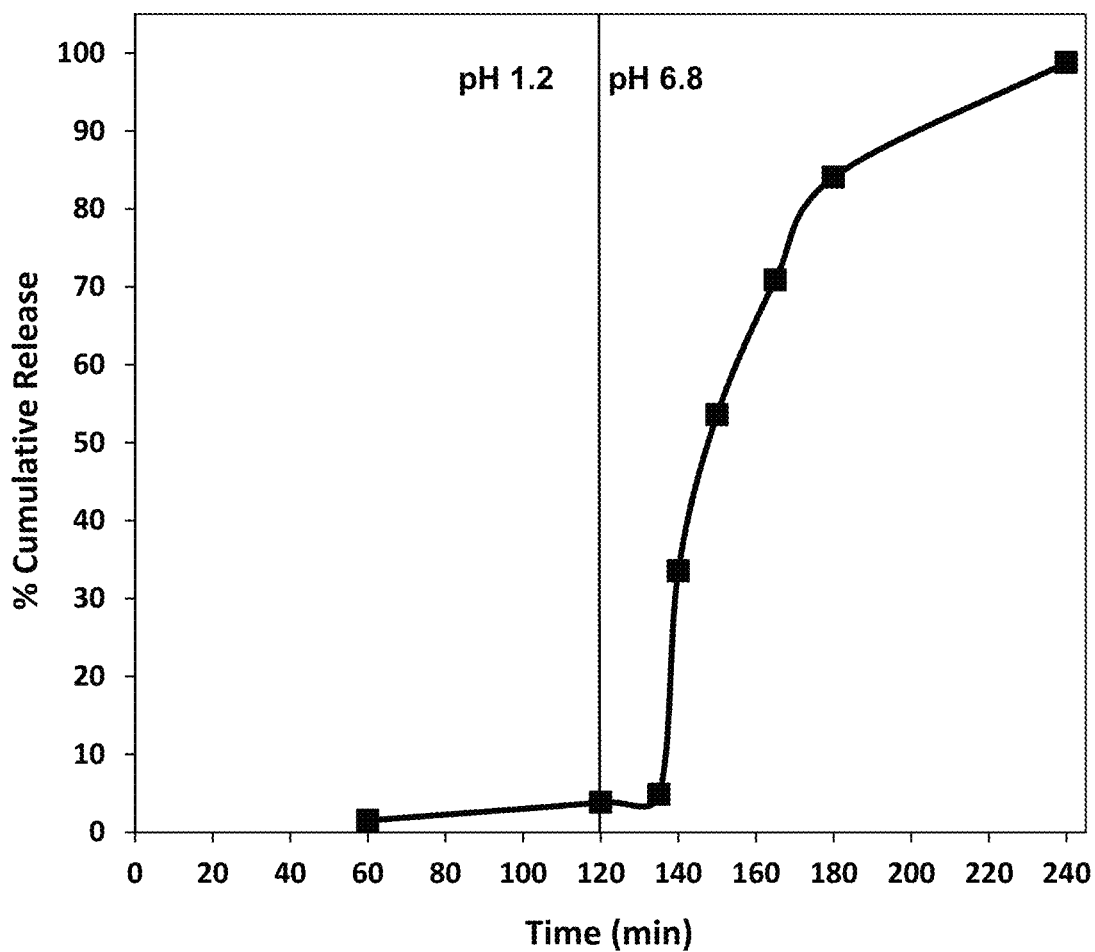
FIG. 12. Two-stage dissolution of 120 mg DMF enteric soft capsule.

A batch of enteric soft capsules (0.038 inch shell thickness) comprising DMF particles having particle size distribution of PSD: d90≤90 µm was prepared with the matrix composition shown in Table 19 and analyzed in two stage (pH 1.2 and pH 6.8) dissolution experiments (FIG. 12). This example provides a lower dose of DMF (120 mg) compared with that shown in Table 6 (240 mg).

TABLE 19

| DMF Fill Composition | | |
|---|---|---|
| Ingredient | mg/capsule | % weight |
| Dimethyl fumarate PSD: d90 ≤ 90 µm | 120 | 28.2 |
| Capmul ® MCM | 228.5 | 53.8 |
| Cremophor ® RH 40 | 42.5 | 10.0 |
| Povidone K 30 | 12.75 | 3.0 |
| Lactic acid | 21.25 | 5.0 |
| TOTAL | 425 mg | 100% |

Example 13

A batch of enteric soft capsules (0.038 inch shell thickness) comprising monomethyl fumarate (MMF) particles having particle size distribution of PSD: d90≤90 µm was prepared with the matrix composition shown in Table 20. This example provides MMF (240 mg).

TABLE 20

MMF Fill Composition

| Ingredient | mg/capsule | % weight |
|---|---|---|
| Monomethyl fumarate PSD: d90 ≤ 90 μm | 240 | 28.2 |
| Capmul ® MCM | 457 | 53.8 |
| Cremophor ® RH 40 | 85 | 10.0 |
| Povidone K 30 | 25.5 | 3.0 |
| Lactic acid | 42.5 | 5.0 |
| TOTAL | 850 mg | 100% |

Example 14

A batch of enteric soft capsules (0.038 inch shell thickness) comprising monomethyl fumarate (MMF) particles having particle size distribution of PSD: d90≤90 μm was prepared with the matrix composition shown in Table 21. This example provides MMF (480 mg).

TABLE 21

MMF Fill Composition

| Ingredient | mg/capsule | % weight |
|---|---|---|
| Monomethyl fumarate PSD: d90 ≤ 90 μm | 480 | 48-56.4 |
| Capmul ® MCM | 216-470 | 25.5-47 |
| Cremophor ® RH 40 | 7.3-120 | 0.85-12 |
| Povidone K 30 | 7.3-50 | 0.85-5 |
| Lactic acid | 21.7-50 | 2.55-5 |
| TOTAL | 850 mg-1000 mg | 100% |

Example 15

Enteric soft capsules comprising particles of dimethyl fumarate, monomethyl fumarate, or a combination thereof having particle size distribution of PSD: d90≤90 μm can be prepared with an 850 mg matrix in the compositions shown in Table 22. This example provides DMF or MMF in a QD formulation (~480 mg).

TABLE 22

DMF or MMF 850 mg Fill Compositions

| | Percent Weight (%) | | | | | |
|---|---|---|---|---|---|---|
| Ingredient | EX1 | EX2 | EX3 | EX4 | EX5 | EX6 |
| Dimethyl fumarate or Monomethyl fumarate PSD: d90 ≤ 90 μm | 56.4 | 56.4 | 56.4 | 56.4 | 56.4 | 56.4 |
| Capmul ® MCM | 30.6 | 39.95 | 28.9 | 28.9 | 25.5 | 32.7 |
| Cremophor ® RH 40 | 8.5 | 0.85 | 8.5 | 8.5 | 10.2 | 6.1 |
| Povidone K 30 | 0.85 | 0.85 | 2.55 | 2.55 | 4.25 | 1.8 |
| Lactic acid | 4.25 | 2.55 | 4.25 | 4.25 | 4.25 | 3.0 |
| TOTAL | 100 | 100 | 100 | 100 | 100 | 100 |

Example 16

Enteric soft capsules comprising particles of dimethyl fumarate, monomethyl fumarate, or a combination thereof having particle size distribution of PSD: d90≤90 μm can be prepared with a 1000 mg matrix in the compositions shown in Table 23. This example provides DMF or MMF in a QD formulation (~480 mg).

TABLE 23

DMF or MMF 1000 mg Fill Compositions

| | Percent Weight (%) | | | | | |
|---|---|---|---|---|---|---|
| Ingredient | EX1 | EX2 | EX3 | EX4 | EX5 | EX6 |
| Dimethyl fumarate or Monomethyl fumarate PSD: d90 ≤ 90 μm | 48 | 48 | 48 | 48 | 48 | 48 |
| Capmul ® MCM | 44 | 36 | 47 | 34 | 34 | 38.9 |
| Cremophor ® RH 40 | 2 | 10 | 1 | 10 | 10 | 7.2 |
| Povidone K 30 | 1 | 1 | 1 | 3 | 3 | 2.2 |
| Lactic acid | 5 | 5 | 3 | 5 | 5 | 3.6 |
| TOTAL | 100 | 100 | 100 | 100 | 100 | 100 |

Example 17

Stability of the Enteric Soft Capsules Over Time

Figure 13:
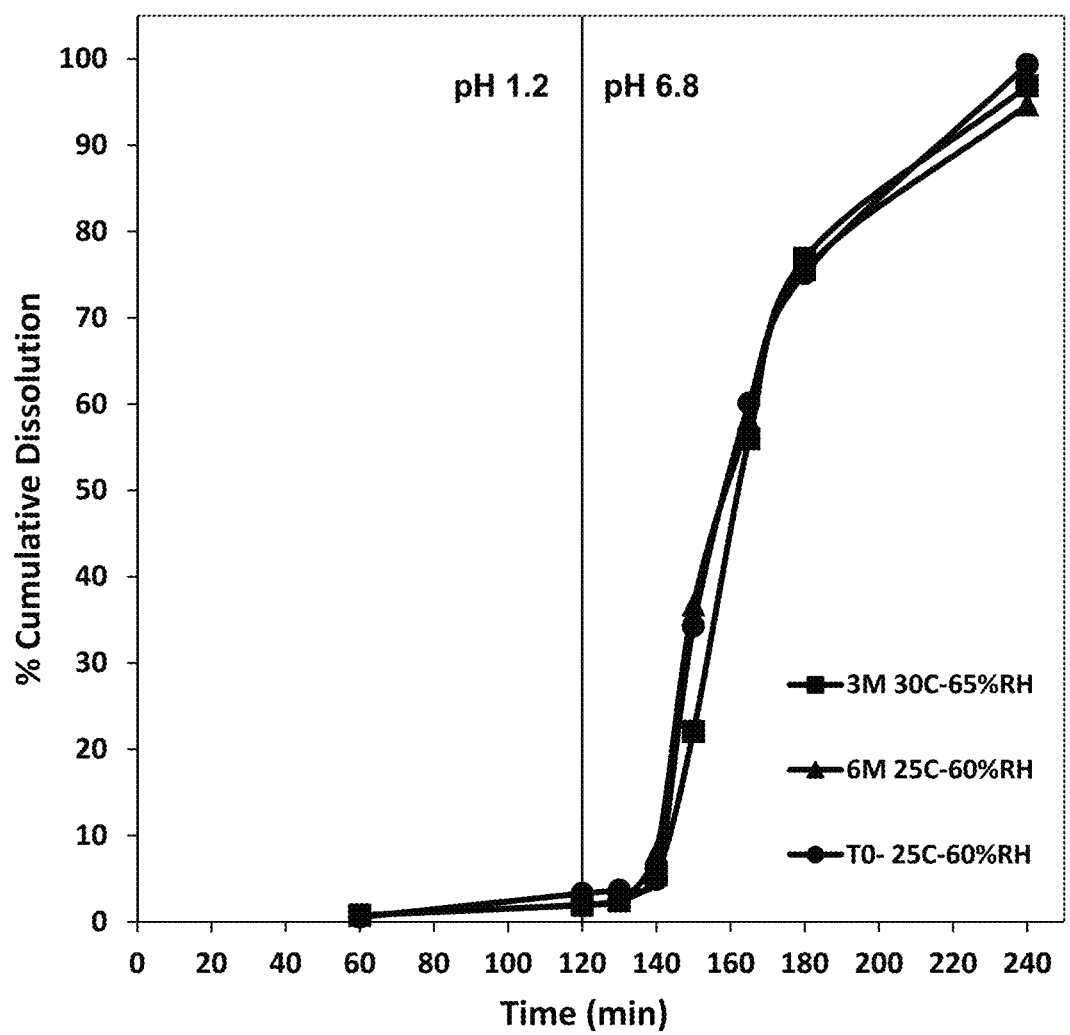
FIG. 13. DMF enteric soft capsule stability at $T_0$ and after 3- and 6-month conditions.

The temporal stability of the dimethyl fumarate enteric soft capsule pharmaceutical composition shown in Table 24 was assessed under three ICH conditions. A sample of DMF enteric soft capsules was subject to chemical analysis and two-stage dissolution shortly after manufacturing ($T_0$). Samples of DMF enteric soft capsules were subjected to Room Temperature Conditions (25° C. and 60% relative humidity) for 1 month, 2, months, 3 months, and 6 months. Other samples of DMF enteric soft capsules were subjected to Intermediate Conditions (30° C. and 65% relative humidity) for 1 month, 2 months, and 3 months. Additional samples of DMF enteric soft capsules were subjected to Accelerated Conditions (40° C. and 75% relative humidity) for 1 month and 2 months. After the designated incubation period, the capsules were chemically analyzed and evaluated in two-stage dissolution experiments at pH 1.2 and 6.8 as described herein if conditions permitted (i.e., non-leaking capsules). Two-stage dissolution results for DMS enteric soft capsules at $T_0$, and after 3- and 6-months at Room Temperature Conditions (25° C. and 60% RH) are shown in FIG. 13.

TABLE 24

GMP DMF Fill Composition

| Ingredient | mg/capsule | % weight |
|---|---|---|
| Dimethyl fumarate PSD: d90 ≤ 90 μm | 240 | 32.0 |

TABLE 24-continued

GMP DMF Fill Composition

| Ingredient | mg/capsule | % weight |
|---|---|---|
| Capmul ® MCM | 375 | 50.0 |
| Cremophor ® RH 40 | 75 | 10.0 |
| Povidone K 30 | 22.5 | 3.0 |
| Lactic acid | 37.5 | 5.0 |
| TOTAL | 750 mg | 100% |

TABLE 25

GMP DMF Stability

| | Initial | 25° C., 60% Relative Humidity | | | |
|---|---|---|---|---|---|
| | $T_0$ | 1 M | 2 M | 3 M | 6 M |
| Assay | 101.2% | 101.0% | 102.4% | 101.25 | 98.8% |
| Degradation Products | | | | | |
| Monomethyl Fumarate | 0.14% | 0.13% | 0.14% | 0.16% | 0.18% |
| RRT 0.74 | ND | ND | 0.07% | 0.09% | 0.18% |
| RRT 1.61 | 0.05% | ND | ND | ND | ND |
| RRT 2.18 | ND | ND | ND | <0.05% | 0.09% |
| Total Degradation Products | 0.19% | 0.13% | 0.21% | 0.25% | 0.45% |

| | 30° C., 65% Relative Humidity | | | 40° C., 75% Rel. Humid. | |
|---|---|---|---|---|---|
| | 1 M | 2 M | 3 M | 1 M | 2 M |
| Assay | 100.1% | 99.4% | 99.5% | 99.3% | 113.1%* |
| Degradation Products | | | | | |
| Monomethyl Fumarate | 0.14% | 0.17% | 0.22% | 0.22% | 0.26% |
| RRT 0.74 | 0.14% | 0.22% | 0.28% | 0.3% | 0.46% |
| RRT 1.61 | 0.06% | 0.11% | 0.14% | 0.15% | 0.35% |
| RRT 2.18 | 0.34% | 0.5% | 0.64% | 0.67% | 1.07% |
| Total Degradation Products | 0.14% | 0.17% | 0.22% | 0.22% | 0.26% |

*Data were collected on fill extracted from leaking capsules.

Note:
Leaking capsules were observed at the 2- and 3-month time points for the accelerated condition (40° C., 75% RH). This was expected for the enteric soft gelatin capsules. The intermediate condition (30° C., 65% RH) and long-term condition (25° C., 60% RH) will be assessed at the 12-month and 24-month time points to assess chemical stability.

Example 18

Fill compositions with increasing amounts of one or more fumarate esters (e.g., dimethyl fumarate, monomethyl fumarate, or a combination thereof ranging from about 0.5 mmol to about 4.0 mmol) having a particle size distribution of PSD: d90≤100 μm in a 750 mg fill are shown in Table 26. Millimole values for DMF or MMF (shaded rows) specify the millimoles of the respective species at the specified mass (mg). These fill compositions may be encapsulated by any of the capsule shell compositions (e.g., an enteric soft capsule shell) as described herein. In one embodiment, the one or more fumarate esters comprise about 0.5 mmol to about 3.7 mmol FAE. In one embodiment, the fumarate ester (FAE) comprises DMF. In another embodiment, the fumarate ester comprises MMF. In another embodiment, the fumarate ester comprises MMF, DMF, or a combination thereof.

TABLE 26

| Fumarate Ester 750 mg Fill Compositions | | | | | | |
|---|---|---|---|---|---|---|
| Ingredient | EX1 | EX2 | EX3 | EX4 | EX5 | EX6 |
| | mg/capsule | | | | | |
| Fumarate Ester PSD: d90 ≤ 100 μm | 80 | 85 | 90 | 95 | 97 | 100 |
| mmol DMF | 0.56 | 0.59 | 0.62 | 0.66 | 0.67 | 0.69 |
| mmol MMF | 0.61 | 0.65 | 0.69 | 0.73 | 0.75 | 0.77 |
| Capmul ® MCM | 535 | 530 | 525 | 520 | 518 | 515 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.12 | 0.13 | 0.14 | 0.15 | 0.15 | 0.15 |
| | Percent Weight (%) | | | | | |
| Fumarate Ester PSD: d90 ≤ 100 μm | 10.7 | 11.3 | 12 | 12.7 | 12.9 | 13.3 |
| Capmul ® MCM | 71.3 | 70.7 | 70 | 69.3 | 69.1 | 68.7 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |
| Ingredient | EX7 | EX8 | EX9 | EX10 | EX11 | EX12 |
| | mg/capsule | | | | | |
| Fumarate Ester PSD: d90 ≤ 100 μm | 105 | 107 | 108 | 110 | 115 | 120 |
| mmol DMF | 0.73 | 0.74 | 0.75 | 0.76 | 0.80 | 0.83 |
| mmol MMF | 0.81 | 0.82 | 0.83 | 0.85 | 0.88 | 0.92 |
| Capmul ® MCM | 510 | 508 | 507 | 505 | 500 | 495 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.16 | 0.17 | 0.17 | 0.17 | 0.18 | 0.19 |
| | Percent Weight (%) | | | | | |
| Fumarate Ester PSD: d90 ≤ 100 μm | 14 | 14.3 | 14.4 | 14.7 | 15.3 | 16 |
| Capmul ® MCM | 68 | 67.7 | 67.6 | 67.3 | 66.7 | 66 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |
| Ingredient | EX13 | EX14 | EX15 | EX16 | EX17 | EX18 |
| | mg/capsule | | | | | |
| Fumarate Ester PSD: d90 ≤ 100 μm | 160 | 170 | 180 | 190 | 194 | 200 |
| mmol DMF | 1.11 | 1.18 | 1.25 | 1.32 | 1.35 | 1.39 |
| mmol MMF | 1.23 | 1.31 | 1.38 | 1.46 | 1.49 | 1.54 |
| Capmul ® MCM | 455 | 445 | 435 | 425 | 421 | 415 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.27 | 0.29 | 0.32 | 0.34 | 0.35 | 0.36 |
| | Percent Weight (%) | | | | | |
| Fumarate Ester PSD: d90 ≤ 100 μm | 21.3 | 22.7 | 24 | 25.3 | 25.9 | 26.7 |
| Capmul ® MCM | 60.7 | 59.3 | 58 | 56.7 | 56.1 | 55.3 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |
| Ingredient | EX19 | EX20 | EX21 | EX22 | EX23 | EX24 |
| | mg/capsule | | | | | |
| Fumarate Ester PSD: d90 ≤ 100 μm | 210 | 214 | 216 | 220 | 230 | 240 |
| mmol DMF | 1.46 | 1.48 | 1.50 | 1.53 | 1.60 | 1.67 |

TABLE 26-continued

| Fumarate Ester 750 mg Fill Compositions | | | | | | |
|---|---|---|---|---|---|---|
| mmol MMF | 1.61 | 1.64 | 1.66 | 1.69 | 1.77 | 1.84 |
| Capmul ® MCM | 405 | 401 | 399 | 395 | 385 | 375 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.39 | 0.40 | 0.40 | 0.42 | 0.44 | 0.47 |
| Percent Weight (%) | | | | | | |
| Fumarate Ester PSD: d90 ≤ 100 μm | 28 | 28.5 | 28.8 | 29.3 | 30.7 | 32 |
| Capmul ® MCM | 54 | 53.5 | 53.2 | 52.7 | 51.3 | 50 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |

| Ingredient | EX25 | EX26 | EX27 | EX28 | EX29 | EX30 |
|---|---|---|---|---|---|---|
| mg/capsule | | | | | | |
| Fumarate Ester PSD: d90 ≤ 100 μm | 320 | 340 | 360 | 380 | 388 | 400 |
| mmol DMF | 2.22 | 2.36 | 2.50 | 2.64 | 2.69 | 2.78 |
| mmol MMF | 2.46 | 2.61 | 2.77 | 2.92 | 2.98 | 3.07 |
| Capmul ® MCM | 295 | 275 | 255 | 235 | 227 | 215 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.74 | 0.83 | 0.92 | 1.03 | 1.07 | 1.14 |
| Percent Weight (%) | | | | | | |
| Fumarate Ester PSD: d90 ≤ 100 μm | 42.7 | 45.3 | 48 | 50.7 | 51.7 | 53.3 |
| Capmul ® MCM | 39.3 | 36.7 | 34 | 31.3 | 30.3 | 28.7 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |

| Ingredient | EX31 | EX32 | EX33 | EX34 | EX35 | EX36 |
|---|---|---|---|---|---|---|
| mg/capsule | | | | | | |
| Fumarate Ester PSD: d90 ≤ 100 μm | 420 | 428 | 432 | 440 | 460 | 480 |
| mmol DMF | 2.91 | 2.97 | 3.00 | 3.05 | 3.19 | 3.33 |
| mmol MMF | 3.23 | 3.29 | 3.32 | 3.38 | 3.54 | 3.69 |
| Capmul ® MCM | 195 | 187 | 183 | 175 | 155 | 135 |
| Cremophor ® RH 40 | 75 | 75 | 75 | 75 | 75 | 75 |
| Povidone K 30 | 22.5 | 22.5 | 22.5 | 22.5 | 22.5 | 22.5 |
| Lactic acid | 37.5 | 37.5 | 37.5 | 37.5 | 37.5 | 37.5 |
| TOTAL | 750 | 750 | 750 | 750 | 750 | 750 |
| Ratio FAE to Fill | 0.74 | 0.83 | 0.92 | 1.03 | 1.07 | 1.14 |
| Percent Weight (%) | | | | | | |
| Fumarate Ester PSD: d90 ≤ 100 μm | 56 | 57.1 | 57.6 | 58.7 | 61.3 | 64 |
| Capmul ® MCM | 26 | 24.9 | 24.4 | 23.3 | 20.7 | 18 |
| Cremophor ® RH 40 | 10 | 10 | 10 | 10 | 10 | 10 |
| Povidone K 30 | 3 | 3 | 3 | 3 | 3 | 3 |
| Lactic acid | 5 | 5 | 5 | 5 | 5 | 5 |
| TOTAL | 100 | 100 | 100 | 100 | 100 | 100 |

Example 19

Fill compositions having one or more fumarate esters (e.g., dimethyl fumarate, monomethyl fumarate, or a combination thereof ranging from about 0.5 mmol to about 3.5 mmol) having a particle size distribution of PSD: d90≤100 μm with a constant weight ratio of fumarate ester to fill (e.g., about 0.40) are shown in Table 27. Millimole values for DMF or MMF (shaded rows) specify the millimoles of the respective species at the specified mass (mg). These fill compositions may be encapsulated by any of the capsule shell compositions (e.g., an enteric soft capsule shell) as described herein. In one embodiment, the fumarate ester comprises DMF. In another embodiment, the fumarate ester comprises MMF. In another embodiment, the fumarate ester comprises MMF, DMF, or a combination thereof.

TABLE 27

Fumarate Ester Fill Compositions

| Ingredient | Percent Weight (%) EX1-EX4 | mg/capsule EX1 | EX2 | EX3 | EX4 |
|---|---|---|---|---|---|
| Fumarate Ester PSD: d90 ≤ 100 μm | 28.5 | 80 | 85 | 160 | 170 |
| mmol DMF | N/A | 0.56 | 0.59 | 1.11 | 1.18 |
| mmol MMF | N/A | 0.61 | 0.65 | 1.23 | 1.31 |
| Capmul ® MCM | 53.5 | 150 | 159 | 300 | 318 |
| Cremophor ® RH 40 | 10 | 28 | 29.8 | 56 | 59.5 |
| Povidone K 30 | 3 | 8.4 | 8.9 | 16.8 | 17.9 |
| Lactic acid | 5 | 14 | 14.9 | 28 | 29.8 |
| TOTAL | 100 | 280 | 298 | 560 | 595 |

| Ingredient | Percent Weight (%) EX5-EX8 | mg/capsule EX5 | EX6 | EX7 | EX8 |
|---|---|---|---|---|---|
| Fumarate Ester PSD: d90 ≤ 100 μm | 28.5 | 90 | 95 | 180 | 190 |
| mmol DMF | N/A | 0.62 | 0.66 | 1.25 | 1.32 |
| mmol MMF | N/A | 0.69 | 0.73 | 1.38 | 1.46 |
| Capmul ® MCM | 53.5 | 169 | 178 | 337 | 356 |
| Cremophor ® RH 40 | 10 | 31.5 | 33.3 | 63 | 66.5 |
| Povidone K 30 | 3 | 9.5 | 10 | 18.9 | 20 |
| Lactic acid | 5 | 15.8 | 16.6 | 31.5 | 33.3 |
| TOTAL | 100 | 315 | 333 | 630 | 665 |

| Ingredient | Percent Weight (%) EX9-EX12 | mg/capsule EX9 | EX10 | EX11 | EX12 |
|---|---|---|---|---|---|
| Fumarate Ester PSD: d90 ≤ 100 μm | 28.5 | 100 | 107 | 200 | 214 |
| mmol DMF | N/A | 0.69 | 0.74 | 1.39 | 1.48 |
| mmol MMF | N/A | 0.77 | 0.82 | 1.54 | 1.64 |
| Capmul ® MCM | 53.5 | 187 | 201 | 375 | 401 |
| Cremophor ® RH 40 | 10 | 35 | 37.5 | 70.1 | 75 |
| Povidone K 30 | 3 | 10.5 | 11.3 | 21 | 22.5 |
| Lactic acid | 5 | 17.5 | 18.8 | 35.1 | 37.5 |
| TOTAL | 100 | 350 | 375 | 701 | 750 |

| Ingredient | Percent Weight (%) EX13-EX16 | mg/capsule EX17 | EX18 | EX19 | EX20 |
|---|---|---|---|---|---|
| Fumarate Ester PSD: d90 ≤ 100 μm | 28.5 | 105 | 110 | 210 | 220 |
| mmol DMF | N/A | 0.73 | 0.76 | 1.46 | 1.53 |
| mmol MMF | N/A | 0.81 | 0.85 | 1.61 | 1.69 |
| Capmul ® MCM | 53.5 | 197 | 206 | 393 | 412 |
| Cremophor ® RH 40 | 10 | 36.8 | 38.5 | 73.5 | 77.0 |
| Povidone K 30 | 3 | 11.0 | 11.6 | 22.1 | 23.1 |
| Lactic acid | 5 | 18.4 | 19.3 | 36.8 | 38.5 |
| TOTAL | 100 | 368 | 385 | 735 | 770 |

| Ingredient | Percent Weight (%) EX13-EX16 | mg/capsule EX17 | EX18 | EX19 | EX20 |
|---|---|---|---|---|---|
| Fumarate Ester PSD: d90 ≤ 100 μm | 28.5 | 115 | 120 | 230 | 240 |
| mmol DMF | N/A | 0.80 | 0.83 | 1.60 | 1.67 |
| mmol MMF | N/A | 0.88 | 0.92 | 1.77 | 1.84 |
| Capmul ® MCM | 53.5 | 215 | 225 | 431 | 449 |
| Cremophor ® RH 40 | 10 | 40.3 | 42.0 | 80.5 | 84.0 |
| Povidone K 30 | 3 | 12.1 | 12.6 | 24.2 | 25.2 |
| Lactic acid | 5 | 20.1 | 21.0 | 40.3 | 42.0 |
| TOTAL | 100 | 403 | 420 | 805 | 840 |

TABLE 27-continued

Fumarate Ester Fill Compositions

| Ingredient | Percent Weight (%) EX13-EX16 | mg/capsule EX13 | EX14 | EX15 | EX16 |
|---|---|---|---|---|---|
| Fumarate Ester PSD: d90 ≤ 100 μm | 28.5 | 350 | 375 | 400 | 428 |
| mmol DMF | N/A | 2.42 | 2.6 | 2.78 | 2.97 |
| mmol MMF | N/A | 2.68 | 2.88 | 3.07 | 3.29 |
| Capmul ® MCM | 53.5 | 655 | 702 | 750 | 802 |
| Cremophor ® RH 40 | 10 | 123 | 131 | 140 | 150 |
| Povidone K 30 | 3 | 36.8 | 39.4 | 42.1 | 45 |
| Lactic acid | 5 | 61.3 | 65.6 | 70.1 | 75 |
| TOTAL | 100 | 1225 | 1313 | 1402 | 1500 |

Example 20

A batch of enteric soft capsules (0.038-inch shell thickness) comprising BSL-11 particles having particle size distribution of PSD: d90≤90 μm were prepared with the matrix composition shown in Table 28.

TABLE 28

BLS-11 Fill Composition

| Fill Ingredients | Percent Weight (%) | Mass/capsule (mg) |
|---|---|---|
| BLS-11, PSD: d90 ≤ 90 μm | 28.50 | 214 |
| Capmul ® MCM | 53.50 | 401 |
| Cremophor ® RH 40 | 10.00 | 75 |
| Povidone K 30 | 3.00 | 23 |
| Lactic Acid | 5.00 | 38 |
| Total Fill Weight | 100.0% | 750 |
| Total Capsule Weight | | 1116 |

Figure 14:
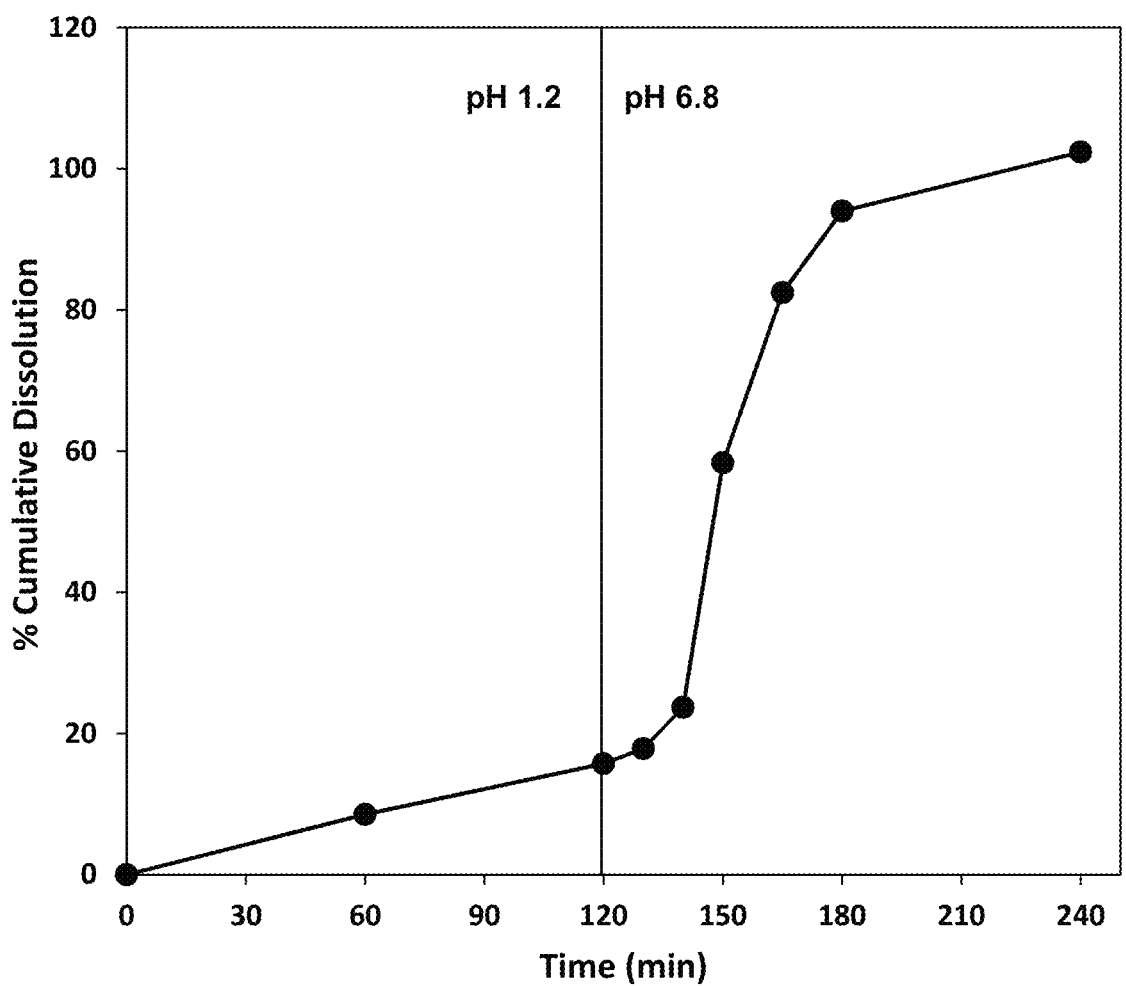
FIG. 14. Two-stage dissolution of BLS-11 (~215 mg) enteric soft capsule.

Samples from a batch of enteric soft capsules comprising the composition shown in Table 28 were subject to two-stage dissolution experiments in a USP Apparatus II with the parameters shown in Table 29. For these experiments, the capsule was introduced in to simulated gastric fluid, 0.1 N HCl, pH 1.2, for 2 hours. After 2 hours, the capsule was transferred to simulated intestinal fluid, phosphate buffer, pH 6.8. The results are shown in FIG. 14. The results show that the capsules retain their enteric properties for at least 2 hours in simulated gastric fluid at pH 1.2. The capsules began releasing BLS-11 within ~10 minutes after being transferred to simulated intestinal fluid, pH 6.8, and achieved 100% dissolution after 120 minutes at pH 6.8.

TABLE 29

Two-stage Dissolution Analysis Parameters

| | |
|---|---|
| USP Apparatus II | Agitation Rate 100 RPM |
| | Temperature 37.0 ± 0.5° C. |
| Media/Volume | 0.1N HCl, pH 1.2, 500 mL |
| | Phosphate buffer, pH 6.8, 500 mL |
| Sample Profile: | Samples obtained at 60 min and 120 min in 0.1N HCl |
| | Samples obtained at 10, 20, 30, 45, 60, 120 min in phosphate buffer pH 6.8 |

Example 21

Method for Measurement of Fumarate Ester Particles Size Distribution

Fumarate ester particles (dimethyl fumarate or mono methyl fumarate) in the form of a dry powder were measured using a Malvern Mastersizer 2000 instrument equipped with vacuum unit and air pressure following manufacturer instructions; see, e.g. The Mastersizer 2000 Operators Guide; MAN0247-2-0, Malvern Instruments Ltd. (1999), which is incorporated by reference herein for such teachings. Approximately 1.0 gram of the test sample was introduced into the dry powder feeder and measured under the parameters shown in Table 28, and the volume size distribution and the volume mean diameter were determined. In one aspect, described herein, the particle size distribution is expressed as a particle volume distribution and the mean particle size of the distribution is expressed as a volume mean diameter.

TABLE 30

Particle Size Distribution Measurement Parameters

| | |
|---|---|
| Analysis Model | General Purpose |
| Sensitivity | Normal |
| Particle RI | 1.468 |
| Vibration feed rate | 60% |
| Dispersive air pressure | 1.3 bars |
| Absorption | 0.1 |
| Measurement time | 6 seconds |
| Measurement snaps | 6,000 |
| Background time | 6 seconds |
| Background snaps | 6,000 |
| No. of measurements | 1 per cycle |
| Obscuration | 0.5% to 6.0% |

Example 22

Clinical Study of Test Pharmaceutical Compositions Comprising Fumarate Esters Patient Population Non-smoking male or females (n=24) within the age range of 18 to 65 years, having a Body Mass Index (BMI) greater than or equal to 18.5 kg/m² and less than or equal to 29.9 kg/m² and having given their written informed consent were at the Period-I check-in of the study. The patient demographics and number of patients dosed is provided in Table 31. They did not have any significant diseases or clinically significant abnormal findings during screening, medical history, physical and clinical examinations, laboratory evaluation, 12-lead ECG recording and vital sign measurement. Female volunteers had a negative pregnancy test. Volunteers who meet all the inclusion and exclusion criteria were enrolled into the study.

All the subjects willing to participate in the study were screened no more than 28 days before the first drug administration in order to assess their eligibility by satisfying all of the inclusion and exclusion criteria. During screening, the medical history of the subjects was elicited and they underwent a general clinical examination, measurement of blood pressure, heart rate, body temperature, respiratory rate, 12-Lead ECG, clinical laboratory evaluations, immunological tests for HIV (Human Immunodeficiency Virus), HBsAg (Hepatitis B Surface Antigen) and HCV (Hepatitis C Virus), Alcohol screen, Nicotine screen and Screen for drugs of abuse. Urine pregnancy test was performed for all female subjects. Subjects were selected for inclusion in the study no more than 28 days before the first drug administration.

TABLE 31

Study Population Inclusion Numbers and Parameter Information

| | | |
|---|---|---|
| No. Planned for Inclusion | | 24 |
| Enrolled and Checked-in | | 34 |
| | | (Subject Nos. 1001-1024 and 10 standby subjects) |
| Dosed | Period-I | 24 |
| | Period-II (7 days later) | 23 |
| Dismissed | | 01 |
| Analyzed | | 23 |
| Considered for statistical analysis | | 23 |

| Parameters | Dosed Subjects (24) | Completed Study (23) |
|---|---|---|
| Age (years) | 42.2 ± 12.81 | 42.2 ± 13.10 |
| Height (cm) | 171.14 ± 8.668 | 171.32 ± 8.817 |
| Weight (kg) | 75.05 ± 10.135 | 75.35 ± 10.258 |
| BMI (kg/m$^2$) | 25.55 ± 2.280 | 25.60 ± 2.320 |

Study Methodology

The performed study was a randomized, pilot, two-way crossover, open-label, single-dose, fasting study, with a screening period of 28-days prior to the first dose administration. In each study period, 19 blood samples, including one pre-dose blood sample, were collected from each subject except for the subject who did not complete the study to analyze the pharmacokinetic profile of the Test pharmaceutical composition as well as the Reference pharmaceutical product.

Based on the elimination half-life of dimethyl fumarate, a washout period of 7-days was kept in between the successive dosing days. Multiple blood samples were collected to assess the bioequivalence between the Test and the Reference product. For this study with a crossover design, each subject except for one dismissed subject received both the products (Test Product-T and Reference Product-R) during the study. Hence, every subject acted as his own control and no separate group of subjects was required to act as the control group. Subjects were dosed according to the treatment sequence provided in Table 32. The duration of the clinical part of the study was about 9 days (one day prior to the drug administration in Period-I until the last study procedure in Period-II).

TABLE 32

Treatment Sequence

| | Period-I | Period-II |
|---|---|---|
| Sequence 1 | Treatment-R (Reference) | Treatment-T (Test) |
| Sequence 2 | Treatment-T (Test) | Treatment-R (Reference) |

After an overnight fast of at least 10 hours, a single oral dose (240 mg) of a Test pharmaceutical composition comprising dimethyl fumarate or a Reference dimethyl fumarate composition was administered to the subjects in sitting posture with 240 mL of drinking water at ambient temperature. The administration was as per the randomization schedule and under open-label conditions.

Dosing water was measured and poured into individual containers before dosing. The containers were then covered and allowed to remain at ambient temperature until used. The drug was provided to the subjects in unit-dose containers. A visual inspection of each subject's mouth and hands was performed immediately after dosing to ensure drug ingestion.

During the first 4 hours post-dose, subjects were encouraged to stay awake, seated in an upright position, and allowed to rise under supervision only for brief periods of time, in order to comply with study-related activities and to use the washroom. Subjects were permitted to lie down for treatment of any adverse event.

No water ingestion was permitted from 1.0 hour pre-dose to 1.0 hour post-dose, with the exception of the 240 mL of dosing water.

No food was allowed for at least 4 hours post-dose. Standardized meals with beverages were provided to the subjects at the following times: between 4.5 and 5.5 hours post-dose; between 9.5 and 10.5 hours post-dose; and at 13.5 hours post-dose.

All meals and beverages were free of alcohol, grapefruit products, xanthine, and caffeine and were identical between the study periods.

Safety was assessed from the screening period to the end of the study. It was assessed through clinical examinations, vital signs assessment, 12-lead electrocardiogram (ECG), clinical laboratory parameters (e.g., biochemistry, hematology, immunology, and urine analysis), pregnancy test (for female subjects), subjective symptomatology, and monitoring of adverse events.

A total of 19 pharmacokinetic blood samples (6 mL each) were drawn in each period according to the following schedule: 0 (pre-dose), and at intervals of 0.33, 0.67, 1, 1.25, 1.5, 1.75, 2, 2.25, 2.5, 2.75, 3, 3.33, 3.68, 4, 4.5, 5, 6, and 8 hours post-dose.

The plasma samples of subjects were analyzed using a validated LC-MS/MS method for monomethyl fumarate. Calibration curve using an 8-point calibration curve standards, with concentrations ranging from 21.35 ng/mL to 4967.75 ng/mL were used to determine the concentrations of monomethyl fumarate in the samples of various subjects.

Pharmacokinetic Parameter Calculations

The pharmacokinetic parameters were calculated from the drug concentration versus time point by non-compartmental model using WinNonlin Professional Software Version 5.3 (Pharsight Corporation, USA) for monomethyl fumarate. Statistical comparison of the pharmacokinetic parameters of the two products (Test, Reference) was performed using PROC MIXED of SAS® Version 9.3 (SAS Institute Inc., USA).

The maximum measured plasma concentration ($C_{max}$) and the time of observing the peak concentration ($T_{max}$) was taken directly from the plasma concentration versus time profile of the individual subjects.

Area under plasma concentration versus time curve ($AUC_{0\to\tau}$) in h·ng/mL from time zero to the last measurable concentration as calculated by the linear trapezoidal rule.

Area under the plasma concentration versus time curve ($AUC_{0\to\infty}$) in h·ng/mL from time zero to infinity; where $AUC_{0\to\infty}=AUC_{0\to\tau}+C_t/\lambda_z$; $C_t$ is the last measurable concentration and $\lambda_z$ is the terminal rate constant. The $AUC_{0\to\infty}$ was the sum of measurable and extrapolated parts.

First order rate constants associated with the terminal (log-linear) portion of the curve were estimated via linear regression of time versus log concentration. This parameter was calculated by linear least squares regression analysis using last three or more non-zero plasma concentration values. The units of $\lambda_z$ were hours$^{-1}$ (1/h).

The terminal half-life was calculated using the formula: $0.693/\lambda_z$. The unit of $t_{1/2}$ was hour (h).

The residual area in percentage was determined by the formula:

$$[(AUC_{0\to\infty}-AUC_{0\to\tau})/AUC_{0\to\infty}]\times 100.$$

Figure 15:
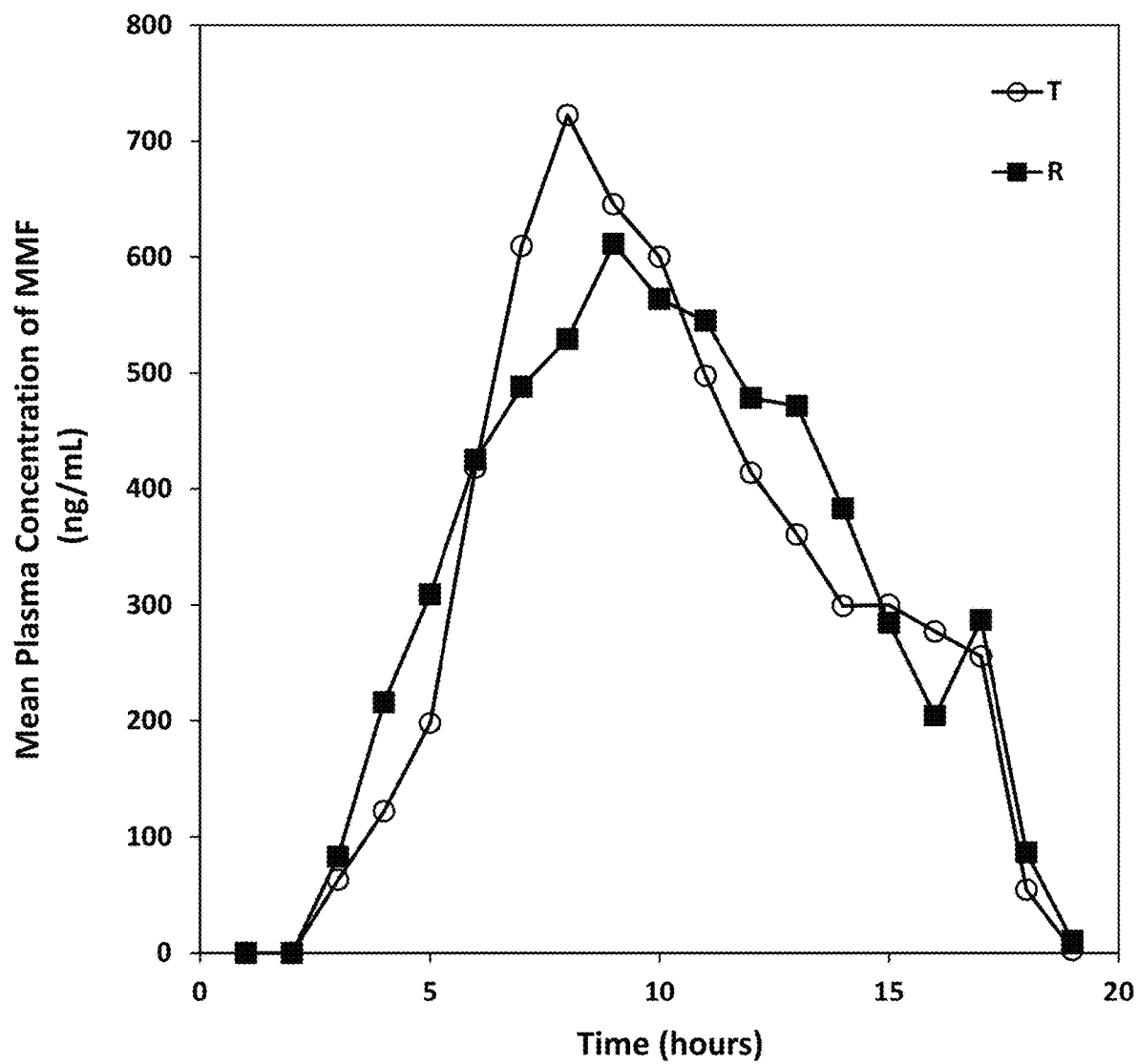
FIG. 15. Mean plasma concentration of MMF over time following dose administration.

The pharmacokinetic parameters of monomethyl fumarate for Test Product-T and Reference Product-R are summarized in Table 33. The mean plasma concentration versus time curve over eight hours is shown in FIG. 15.

TABLE 33

Pharmacokinetic Parameters of Monomethyl Fumarate;
Test Product-T and Reference Product-R

| Pharmacokinetic Parameters | Mean ± SD (Un-transformed data) | |
| --- | --- | --- |
| | Test Product-T | Reference Product-R |
| $T_{max}$ (h) | 2.5 (1-5) | 2.5 (1-5) |
| $C_{max}$ (ng/mL) | 1321.3 ± 618.9 | 1174.7 ± 433.9 |
| $AUC_{0\to\tau}$ h · ng/mL | 1818.415 ± 532.5886 | 1907.405 ± 525.7948 |
| $AUC_{0\to\infty}$ | 1919.247 ± 533.8147* | 2119.693 ± 688.1376^ |
| $\lambda_z$ (1/h) | 1.323 ± 0.3573* | 1.103 ± 0.3930^ |
| $t_{1/2}$ (h) | 0.563 ± 0.1586* | 0.864 ± 0.8508^ |
| Residual Area in Percentage | 1.799 ± 1.0276* | 6.481 ± 14.0612^ |

*n = 20
^n = 22

Statistical Methods

Descriptive statistics were calculated and reported for all pharmacokinetic parameters of monomethyl fumarate. ANOVA, power, and ratio analysis for ln-transformed pharmacokinetic parameters $C_{max}$, $AUC_{0\to\tau}$, and $AUC_{0\to\infty}$ were calculated and reported for monomethyl fumarate. The 90% confidence interval for the ratio of the geometric least-squares means were calculated for the ln-transformed pharmacokinetic parameters, $C_{max}$, $AUC_{0\to\tau}$, and $AUC_{0\to\infty}$ for monomethyl fumarate. All statistical analyses for Monomethyl Fumarate were performed using PROC MIXED of SAS® Version 9.3 (SAS Institute Inc., USA).

The relative bioavailability analysis (e.g., geometric least squares means, ratios, 90% confidence interval, intra subject CV, and power) of Test Product-T versus Reference Product-R for monomethyl fumarate is summarized in Table 34.

TABLE 34

Relative Bioavailability Results for Monomethyl Fumarate (n = 23)

| Parameters | Geometric Least Squares Means | | | 90% Confidence Interval | Intra Subject CV (%) | Power (%) |
| --- | --- | --- | --- | --- | --- | --- |
| | Test Product-T | Reference Product-R | Ratio (T/R)% | | | |
| $C_{max}$ | 1189.160 | 1102.137 | 107.9 | 92.04-126.49 | 32.1 | 75.3 |
| $AUC_{0\to\tau}$ | 1747.744 | 1847.786 | 94.6 | 87.59-102.14 | 15.2 | 99.8 |
| $AUC_{0\to\infty}$ | 1875.657* | 2034.147^ | 92.2 | 85.17-99.82 | 14.3 | 99.7 |

*n = 20
^n = 22

What is claimed is:

1. A method of treating or reducing symptoms of a multiple sclerosis or psoriasis in a subject, the method comprising administering an oral pharmaceutical composition comprising an immediate releasing single phase non-aqueous liquid vehicle comprising a suspension of a fumarate ester or a salt thereof having the formula:

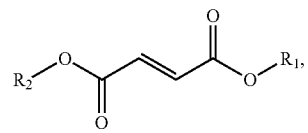

wherein $R_1$ and $R_2$, may be the same or different, and independently represent hydrogen or methyl.

2. The composition of claim 1, wherein $R_1$ is hydrogen.
3. The composition of claim 1, wherein $R_1$ is methyl.
4. The composition of claim 1, wherein $R_2$ is methyl.
5. The composition of claim 1, wherein $R_1$ is hydrogen and $R_2$ is methyl.
6. The composition of claim 1, wherein $R_1$ is methyl and $R_2$ is methyl.
7. The method of claim 1, wherein the fumarate ester is:

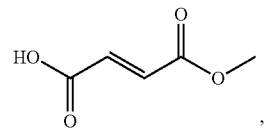

or a salt thereof.

8. The method of claim 1, wherein the fumarate ester is:

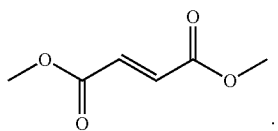

9. The method of claim 1, wherein the composition comprises about 60 mg to about 200 mg of the fumarate ester or salt thereof.

10. The method of claim 1, wherein the composition comprises about 90 mg to about 100 mg or about 100 mg to about 200 mg of the fumarate ester or salt thereof.

11. The method of claim 1, wherein the liquid vehicle comprises mono- and di-glycerides, polyvinylpyrrolidone, and polyoxyl 40 hydrogenated castor oil.

12. The method of claim 1, wherein the composition comprises:
about 30% to about 40% of the fumarate ester or salt thereof by weight of the composition; and
about 55% to about 65% of the liquid vehicle by weight of the composition.

13. The method of claim 1, wherein the liquid vehicle comprises about 5% of lactic acid by weight of the composition.

14. The method of claim 1, wherein the composition is encapsulated in a capsule.

15. The method of claim 14, wherein the capsule provides delayed release of the fumarate ester or salt thereof.

16. The method of claim 1, wherein upon administration to a subject, the composition activates a nuclear factor erythroid-derived 2-like (Nrf2) dependent pathway.

* * * * *